US011497756B2

(12) United States Patent
Bearss et al.

(10) Patent No.: US 11,497,756 B2
(45) Date of Patent: Nov. 15, 2022

(54) TREATMENT REGIMEN FOR CANCERS THAT ARE INSENSITIVE TO BCL-2 INHIBITORS USING THE MCL-1 INHIBITOR ALVOCIDIB

(71) Applicant: Sumitomo Pharma Oncology, Inc., Cambridge, MA (US)

(72) Inventors: David J. Bearss, Alpine, UT (US); Adam Siddiqui-Jain, South Jordan, UT (US); Clifford J. Whatcott, West Jordan, UT (US); Steven L. Warner, Sandy, UT (US)

(73) Assignee: Sumitomo Pharma Oncology, Inc., Cambridge, MA (US)

( * ) Notice: Subject to any disclaimer, the term of this patent is extended or adjusted under 35 U.S.C. 154(b) by 0 days.

(21) Appl. No.: 16/646,853

(22) PCT Filed: Sep. 12, 2018

(86) PCT No.: PCT/US2018/050767
§ 371 (c)(1),
(2) Date: Mar. 12, 2020

(87) PCT Pub. No.: WO2019/055579
PCT Pub. Date: Mar. 21, 2019

(65) Prior Publication Data
US 2020/0276215 A1 Sep. 3, 2020

Related U.S. Application Data

(60) Provisional application No. 62/577,635, filed on Sep. 12, 2017.

(51) Int. Cl.
*A61K 31/675* (2006.01)
*A61K 31/136* (2006.01)
*A61K 31/7068* (2006.01)
*A61P 35/02* (2006.01)

(52) U.S. Cl.
CPC .......... *A61K 31/675* (2013.01); *A61K 31/136* (2013.01); *A61K 31/7068* (2013.01); *A61P 35/02* (2018.01)

(58) Field of Classification Search
CPC ................ A61K 31/675; A61K 31/136; A61K 31/7068; A61P 35/02
USPC ........................................................ 514/49
See application file for complete search history.

(56) References Cited

U.S. PATENT DOCUMENTS

| 4,132,710 A | 1/1979 | Gauthier et al. |
|---|---|---|
| 4,146,629 A | 3/1979 | Kubela et al. |
| 4,522,811 A | 6/1985 | Eppstein et al. |
| 4,676,980 A | 6/1987 | Segal et al. |
| 4,816,567 A | 3/1989 | Cabilly et al. |
| 4,900,727 A | 2/1990 | Kattige et al. |
| 4,946,778 A | 8/1990 | Ladner et al. |
| 4,971,909 A | 11/1990 | Kaneoya et al. |
| 5,225,539 A | 7/1993 | Winter |
| 5,284,856 A | 2/1994 | Naik et al. |
| 5,310,763 A | 5/1994 | Campion et al. |
| 5,545,806 A | 8/1996 | Lonberg et al. |
| 5,545,807 A | 8/1996 | Surani et al. |
| 5,569,825 A | 10/1996 | Lonberg et al. |
| 5,587,458 A | 12/1996 | King et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,674,980 A | 10/1997 | Frankel et al. |
| 5,747,498 A | 5/1998 | Schnur et al. |
| 5,792,783 A | 8/1998 | Tang et al. |
| 5,804,604 A | 9/1998 | Frankel et al. |
| 5,834,504 A | 11/1998 | Tang et al. |
| 5,849,733 A | 12/1998 | Kim |
| 5,861,510 A | 1/1999 | Piscopio et al. |
| 5,863,949 A | 1/1999 | Robinson et al. |
| 5,877,305 A | 3/1999 | Huston et al. |
| 5,883,113 A | 3/1999 | Tang et al. |
| 5,886,020 A | 3/1999 | Tang et al. |
| 5,908,934 A | 6/1999 | Kim |
| 5,916,771 A | 6/1999 | Hori et al. |
| 5,932,595 A | 8/1999 | Bender et al. |
| 5,939,598 A | 8/1999 | Kucherlapati et al. |
| 5,965,703 A | 10/1999 | Horne et al. |
| 6,077,864 A | 6/2000 | Burgess et al. |
| 6,087,366 A | 7/2000 | Park et al. |
| 6,087,392 A | 7/2000 | Reiter |
| 6,090,852 A | 7/2000 | Dack et al. |
| 6,110,964 A | 8/2000 | Robinson |
| 6,136,981 A | 10/2000 | Brion et al. |
| 6,147,061 A | 11/2000 | Reiter |
| 6,153,609 A | 11/2000 | Robinson et al. |
| 6,177,401 B1 | 1/2001 | Ullrich et al. |
| 6,207,669 B1 | 3/2001 | Cockerill et al. |
| 6,214,872 B1 | 4/2001 | Robinson |
| 6,225,473 B1 | 5/2001 | Breipohl et al. |
| 6,258,540 B1 | 7/2001 | Lo et al. |
| 6,284,764 B1 | 9/2001 | Kath et al. |
| 6,291,455 B1 | 9/2001 | Thomas et al. |
| 6,294,532 B1 | 9/2001 | Thomas et al. |
| 6,303,636 B1 | 10/2001 | Robinson, Jr. et al. |
| 6,362,336 B1 | 3/2002 | Lohmann et al. |

(Continued)

FOREIGN PATENT DOCUMENTS

| CA | 2929652 A1 | 5/2015 |
|---|---|---|
| CN | 1583776 A | 2/2005 |

(Continued)

OTHER PUBLICATIONS

Glossary of medical education terms, Institute of International Medical Education. http://www.iime.org/glossary.htm Accessed in Mar. 2013. (Year: 2013).*

(Continued)

*Primary Examiner* — Yih-Horng Shiao
(74) *Attorney, Agent, or Firm* — Hamilton, Brook, Smith & Reynolds, P.C.

(57) ABSTRACT

Methods for treating BCL-2 inhibitor-resistant cancer in subjects using an MCL-1 inhibitor as well as compositions associated with the same are disclosed.

18 Claims, 5 Drawing Sheets

Specification includes a Sequence Listing.

(56) References Cited

U.S. PATENT DOCUMENTS

| | | |
|---|---|---|
| 6,399,633 B1 | 6/2002 | Dumont et al. |
| 6,406,912 B1 | 6/2002 | Holla |
| 6,437,136 B2 | 8/2002 | Breipohl et al. |
| 6,492,383 B1 | 12/2002 | Munchhof et al. |
| 6,495,568 B1 | 12/2002 | Dack et al. |
| 6,511,993 B1 | 1/2003 | Dack et al. |
| 6,576,647 B2 | 6/2003 | Bafus et al. |
| 6,596,726 B1 | 7/2003 | Bridges et al. |
| 6,599,890 B1 | 7/2003 | McClure et al. |
| 6,723,726 B1 | 4/2004 | Cockerill et al. |
| 6,821,990 B2 | 11/2004 | Kesseler |
| 6,828,320 B2 | 12/2004 | Cockerill et al. |
| 6,849,631 B2 | 2/2005 | Carini |
| 7,064,193 B1 | 6/2006 | Cory et al. |
| 7,119,090 B2 | 10/2006 | Tang et al. |
| 7,332,582 B2 | 2/2008 | Hardy et al. |
| 7,417,055 B2 | 8/2008 | Cannizzaro et al. |
| 7,452,901 B2 | 11/2008 | Boojamra et al. |
| 7,488,802 B2 | 2/2009 | Collins et al. |
| 7,572,924 B2 | 8/2009 | Tang et al. |
| 7,695,715 B2 | 4/2010 | Hardy et al. |
| 7,714,005 B2 | 5/2010 | Chen et al. |
| 7,790,902 B2 | 9/2010 | Larson et al. |
| 7,816,398 B2 | 10/2010 | Swindell et al. |
| 7,829,662 B2 | 11/2010 | Korsmeyer et al. |
| 7,868,133 B2 | 1/2011 | Korsmeyer et al. |
| 7,884,127 B2 | 2/2011 | Lal et al. |
| 7,943,743 B2 | 5/2011 | Korman et al. |
| 8,008,449 B2 | 8/2011 | Korman et al. |
| 8,168,179 B2 | 5/2012 | Honjo et al. |
| 8,168,755 B2 | 5/2012 | Cardone et al. |
| 8,217,149 B2 | 7/2012 | Irving et al. |
| 8,221,966 B2 | 7/2012 | Letai |
| 8,304,449 B2 | 11/2012 | Lal et al. |
| 8,354,509 B2 | 1/2013 | Carven et al. |
| 8,372,819 B2 | 2/2013 | Jones et al. |
| 8,460,927 B2 | 6/2013 | Chen |
| 8,552,154 B2 | 10/2013 | Freeman et al. |
| 8,552,156 B2 | 10/2013 | Takayanagi et al. |
| 8,686,119 B2 | 4/2014 | Rotem-Yehudar et al. |
| 8,735,553 B1 | 5/2014 | Li et al. |
| 8,758,752 B2 | 6/2014 | Govindan et al. |
| 8,779,108 B2 | 7/2014 | Queva et al. |
| 8,822,526 B2 | 9/2014 | Rathos et al. |
| 8,841,418 B2 | 9/2014 | Karsunky et al. |
| 8,907,053 B2 | 12/2014 | Sasikumar et al. |
| 8,927,697 B2 | 1/2015 | Davis et al. |
| 8,975,239 B2 | 3/2015 | Green et al. |
| 8,993,731 B2 | 3/2015 | Tyson |
| 9,102,727 B2 | 8/2015 | Freeman et al. |
| 9,138,485 B2 | 9/2015 | Govindan et al. |
| 9,163,087 B2 | 10/2015 | Kuchroo et al. |
| 9,175,082 B2 | 11/2015 | Zhou et al. |
| 9,199,973 B2 | 12/2015 | Carter et al. |
| 9,205,148 B2 | 12/2015 | Langermann et al. |
| 9,241,941 B2 | 1/2016 | Wendel et al. |
| 9,244,059 B2 | 1/2016 | Triebel et al. |
| 9,340,524 B2 | 5/2016 | Chen et al. |
| 9,360,473 B2 | 6/2016 | Cardone |
| 9,493,454 B2 | 11/2016 | Zeng et al. |
| 9,505,839 B2 | 11/2016 | Lonberg et al. |
| 9,540,674 B2 | 1/2017 | Letai |
| 9,605,070 B2 | 3/2017 | Sabatos-Peyton et al. |
| 9,683,048 B2 | 6/2017 | Freeman et al. |
| 9,758,539 B2 | 9/2017 | Siddiqui-Jain et al. |
| 9,856,303 B2 | 1/2018 | Korsmeyer et al. |
| 9,901,574 B2 | 2/2018 | Warner et al. |
| 9,902,759 B2 | 2/2018 | Korsmeyer et al. |
| 9,925,192 B2 | 3/2018 | Strack et al. |
| 9,988,452 B2 | 6/2018 | Freeman et al. |
| 10,132,797 B2 | 11/2018 | Bearss et al. |
| 10,259,835 B2 | 4/2019 | Siddiqui-Jain et al. |
| 10,267,787 B2 | 4/2019 | Bearss et al. |
| 10,357,488 B2 | 7/2019 | Warner et al. |
| 10,422,788 B2 | 9/2019 | Bearss et al. |
| 10,562,925 B2 | 2/2020 | Siddiqui-Jain et al. |
| 10,568,887 B2 | 2/2020 | Bearss et al. |
| 10,624,880 B2 | 4/2020 | Warner et al. |
| 10,682,356 B2 | 6/2020 | Bearss et al. |
| 10,835,537 B2 | 11/2020 | Bearss et al. |
| 11,279,694 B2 | 3/2022 | Siddiqui-Jain et al. |
| 2001/0021704 A1 | 9/2001 | Ghyczy et al. |
| 2002/0016293 A1 | 2/2002 | Ratain et al. |
| 2002/0115613 A1 | 8/2002 | Kumar |
| 2002/0177609 A1 | 11/2002 | Swindell et al. |
| 2003/0065023 A1 | 4/2003 | Swindell et al. |
| 2003/0073661 A1 | 4/2003 | Matsuyama et al. |
| 2003/0119816 A1 | 6/2003 | Haesslein et al. |
| 2004/0106647 A1 | 6/2004 | Schneider et al. |
| 2004/0171809 A1 | 9/2004 | Korsmeyer et al. |
| 2004/0235783 A1 | 11/2004 | Ghyczy et al. |
| 2005/0026959 A1 | 2/2005 | Kesseler |
| 2005/0153991 A1 | 7/2005 | Gianella-Borradori et al. |
| 2007/0093490 A1 | 4/2007 | Prien et al. |
| 2008/0027105 A1 | 1/2008 | Suarez et al. |
| 2008/0108657 A1 | 5/2008 | Kesseler |
| 2009/0030005 A1 | 1/2009 | Kamb et al. |
| 2009/0142337 A1 | 6/2009 | Squires |
| 2010/0143350 A1 | 6/2010 | Green et al. |
| 2010/0286057 A1 | 11/2010 | Walensky et al. |
| 2011/0008371 A1 | 1/2011 | Michelson |
| 2011/0251240 A1 | 10/2011 | Suarez et al. |
| 2012/0225851 A1 | 9/2012 | Cardone et al. |
| 2013/0079424 A1 | 3/2013 | Gerber et al. |
| 2013/0122492 A1 | 5/2013 | Khosravi et al. |
| 2013/0210024 A1 | 8/2013 | Yu et al. |
| 2014/0140956 A1 | 5/2014 | Fairfax et al. |
| 2014/0286861 A1 | 9/2014 | Govindan et al. |
| 2014/0303167 A1 | 10/2014 | Choidas et al. |
| 2015/0051249 A1 | 2/2015 | Walensky |
| 2015/0150869 A1 | 6/2015 | Cardone et al. |
| 2015/0259420 A1 | 9/2015 | Triebel et al. |
| 2015/0301053 A1 | 10/2015 | Pierceall et al. |
| 2015/0352097 A1 | 12/2015 | Cardone et al. |
| 2015/0362479 A1 | 12/2015 | Letai et al. |
| 2016/0178612 A1 | 6/2016 | Cardone |
| 2016/0231314 A1 | 8/2016 | Ryan et al. |
| 2016/0235779 A1 | 8/2016 | Marcus |
| 2016/0258933 A1 | 9/2016 | Letai |
| 2016/0273020 A1 | 9/2016 | Pierceall et al. |
| 2016/0279106 A1 | 9/2016 | Ueda et al. |
| 2016/0303101 A1* | 10/2016 | Warner ............ A61K 31/7068 |
| 2017/0184567 A1 | 6/2017 | Letai |
| 2017/0260268 A1 | 9/2017 | Beatty et al. |
| 2018/0172673 A1* | 6/2018 | Bearss ............ G01N 33/5079 |
| 2018/0280407 A1 | 10/2018 | Warner et al. |
| 2019/0314357 A1 | 10/2019 | Bearss et al. |
| 2020/0048228 A1 | 2/2020 | Siddiqui-Jain et al. |
| 2020/0131210 A1 | 4/2020 | Siddiqui-Jain et al. |
| 2020/0200737 A1 | 6/2020 | Bearss et al. |
| 2020/0215071 A1 | 7/2020 | Bearss et al. |
| 2020/0255462 A1 | 8/2020 | Siddiqui-Jain et al. |
| 2020/0276174 A1 | 9/2020 | Bearss et al. |
| 2020/0281949 A1 | 9/2020 | Warner et al. |
| 2020/0316084 A1 | 10/2020 | Warner et al. |
| 2021/0052568 A1 | 2/2021 | Warner et al. |
| 2021/0228582 A1 | 7/2021 | Bearss et al. |
| 2021/0261585 A1 | 8/2021 | Siddiqui-Jain et al. |
| 2021/0277037 A1 | 9/2021 | Siddiqui-Jain |
| 2021/0332071 A1 | 10/2021 | Siddiqui-Jain et al. |
| 2021/0379402 A1 | 12/2021 | Smith et al. |
| 2022/0125776 A1 | 4/2022 | Bearss et al. |

FOREIGN PATENT DOCUMENTS

| | | |
|---|---|---|
| EP | 0137193 A2 | 4/1985 |
| EP | 0253739 B1 | 10/1989 |
| EP | 0253738 B1 | 1/1990 |
| EP | 0 507 278 A2 | 10/1992 |
| EP | 0 241 003 B1 | 10/1993 |
| EP | 0 321 918 B1 | 3/1994 |
| EP | 0 606 046 A1 | 7/1994 |
| EP | 0 366 061 B1 | 1/1996 |
| EP | 0 474 129 B1 | 12/1996 |

(56) References Cited

FOREIGN PATENT DOCUMENTS

| | | |
|---|---|---|
| EP | 0 780 386 A1 | 6/1997 |
| EP | 0 818 442 A2 | 1/1998 |
| EP | 0 931 788 A2 | 7/1999 |
| EP | 1 004 578 A2 | 5/2000 |
| EP | 0 979 824 B1 | 10/2004 |
| EP | 3049443 A4 | 4/2017 |
| FR | 2 338 043 A1 | 8/1977 |
| GB | 9912961.1 | 6/1999 |
| IN | CHENP-2007-03645 A | 8/2007 |
| JP | 2004-529125 A | 9/2004 |
| JP | 2007-291111 A | 11/2007 |
| JP | 2008-513494 A | 5/2008 |
| JP | 2009-507820 A | 2/2009 |
| JP | 2011-511803 A | 4/2011 |
| JP | 2013-533213 A | 8/2013 |
| RU | 2 438 664 C2 | 1/2012 |
| RU | 2 474 582 C2 | 2/2013 |
| RU | 2 552 642 C2 | 6/2015 |
| WO | 1990/005719 A1 | 5/1990 |
| WO | 1991/000360 A1 | 1/1991 |
| WO | WO 9209589 A1 | 6/1992 |
| WO | 1992/020373 A1 | 11/1992 |
| WO | 1993/008829 A1 | 5/1993 |
| WO | 1994/002602 A1 | 2/1994 |
| WO | 1994/011026 A2 | 5/1994 |
| WO | 1995/019970 A1 | 7/1995 |
| WO | 1995/021613 A1 | 8/1995 |
| WO | 1996/015263 A1 | 5/1996 |
| WO | 1996/027011 A1 | 9/1996 |
| WO | 1996/027583 A1 | 9/1996 |
| WO | 1996/033172 A1 | 10/1996 |
| WO | 1996/033735 A1 | 10/1996 |
| WO | 1996/034096 A1 | 10/1996 |
| WO | 1997/005265 A1 | 2/1997 |
| WO | 1997/013760 A1 | 4/1997 |
| WO | 1997/016447 A1 | 5/1997 |
| WO | 1997/022596 A1 | 6/1997 |
| WO | 1997/030174 A1 | 8/1997 |
| WO | 1997/032856 A1 | 9/1997 |
| WO | 1997/042949 A1 | 11/1997 |
| WO | 1998/002434 A1 | 1/1998 |
| WO | 1998/002437 A1 | 1/1998 |
| WO | 1998/002438 A1 | 1/1998 |
| WO | 1998/003516 A1 | 1/1998 |
| WO | 1998/007697 A1 | 2/1998 |
| WO | 1998/013344 A1 | 4/1998 |
| WO | 1998/014451 A1 | 4/1998 |
| WO | 1998/030566 A1 | 7/1998 |
| WO | 1998/033768 A1 | 8/1998 |
| WO | 1998/033798 A2 | 8/1998 |
| WO | 1998/034915 A1 | 8/1998 |
| WO | 1998/034918 A1 | 8/1998 |
| WO | 1998/050356 A1 | 11/1998 |
| WO | 1998/054093 A1 | 12/1998 |
| WO | 1999/007675 A1 | 2/1999 |
| WO | 1999/010349 A1 | 3/1999 |
| WO | 1999/016755 A1 | 4/1999 |
| WO | 1999/016787 A1 | 4/1999 |
| WO | 1999/024440 A1 | 5/1999 |
| WO | 1999/029667 A1 | 6/1999 |
| WO | 1999/035132 A1 | 7/1999 |
| WO | 1999/035146 A1 | 7/1999 |
| WO | 1999/052889 A1 | 10/1999 |
| WO | 1999/052910 A1 | 10/1999 |
| WO | 1999/053049 A1 | 10/1999 |
| WO | 1999/061422 A1 | 12/1999 |
| WO | 1999/062890 A1 | 12/1999 |
| WO | 2000/006134 A2 | 2/2000 |
| WO | 2000/012071 A2 | 3/2000 |
| WO | 2000/044362 A2 | 8/2000 |
| WO | 2000/059526 A1 | 10/2000 |
| WO | 2001/012661 A2 | 2/2001 |
| WO | 2001/060814 A2 | 8/2001 |
| WO | 2002/020568 A2 | 3/2002 |
| WO | 2003/028001 A1 | 4/2003 |
| WO | 2003/040168 A2 | 5/2003 |
| WO | 2004/022580 A2 | 3/2004 |
| WO | 2004/058804 A1 | 7/2004 |
| WO | 2005/017107 A2 | 2/2005 |
| WO | 2005/044839 A2 | 5/2005 |
| WO | 2006/099667 A1 | 9/2006 |
| WO | 2006/101846 A1 | 9/2006 |
| WO | WO 2006121168 A1 | 11/2006 |
| WO | 2007/123791 A2 | 11/2007 |
| WO | 2008/021484 A2 | 2/2008 |
| WO | 2008/106635 A1 | 9/2008 |
| WO | WO 2008132601 A1 | 11/2008 |
| WO | WO 2009044273 A2 | 4/2009 |
| WO | WO 2010019570 A2 | 2/2010 |
| WO | 2010/030727 A1 | 3/2010 |
| WO | WO 2010027827 A2 | 3/2010 |
| WO | 2010/093742 A1 | 8/2010 |
| WO | 2010/147961 A1 | 12/2010 |
| WO | WO 2011/054553 A1 | 5/2011 |
| WO | WO 2011066342 A2 | 6/2011 |
| WO | 2011/088137 A2 | 7/2011 |
| WO | 2011/143660 A2 | 11/2011 |
| WO | WO 2011153374 A1 | 12/2011 |
| WO | WO 2012/075383 A2 | 6/2012 |
| WO | 2012/122370 A2 | 9/2012 |
| WO | WO 2012145493 A1 | 10/2012 |
| WO | 2013/082660 A1 | 6/2013 |
| WO | WO 2013079174 A1 | 6/2013 |
| WO | 2013/138702 A2 | 9/2013 |
| WO | 2013/170176 A2 | 11/2013 |
| WO | 2013/182519 A1 | 12/2013 |
| WO | 2013/188355 A1 | 12/2013 |
| WO | 2013/188978 A1 | 12/2013 |
| WO | WO 2014022758 A2 | 2/2014 |
| WO | 2014/047342 A1 | 3/2014 |
| WO | 2014/059028 A1 | 4/2014 |
| WO | WO 2014055897 A2 | 4/2014 |
| WO | 2014/066848 A1 | 5/2014 |
| WO | WO 2014100079 A1 | 6/2014 |
| WO | WO 2014140180 A1 | 9/2014 |
| WO | WO 2014179664 A2 | 11/2014 |
| WO | WO 2014194302 A2 | 12/2014 |
| WO | WO 2014209804 A1 | 12/2014 |
| WO | 2013/170176 A3 | 1/2015 |
| WO | 2015/010094 A1 | 1/2015 |
| WO | 2015/017788 A1 | 2/2015 |
| WO | 2015/042249 A1 | 3/2015 |
| WO | 2015/047510 A1 | 4/2015 |
| WO | WO 2015061668 A1 | 4/2015 |
| WO | 2015/066305 A1 | 5/2015 |
| WO | 2015/070020 A2 | 5/2015 |
| WO | WO 2015081158 A1 | 6/2015 |
| WO | WO 2015085847 A1 | 6/2015 |
| WO | WO 2015109124 A2 | 7/2015 |
| WO | WO 2015112800 A1 | 7/2015 |
| WO | WO 2015112805 A1 | 7/2015 |
| WO | WO 2015116539 A1 | 8/2015 |
| WO | 2015/130585 A1 | 9/2015 |
| WO | 2015/161247 A1 | 10/2015 |
| WO | WO 2015181342 A1 | 12/2015 |
| WO | WO 2015195163 A1 | 12/2015 |
| WO | WO 2015200119 A1 | 12/2015 |
| WO | WO 2016000619 A1 | 1/2016 |
| WO | WO 2016/019096 A1 | 2/2016 |
| WO | WO 2016028672 A1 | 2/2016 |
| WO | WO 2016/033114 A1 | 3/2016 |
| WO | 2016/061144 A1 | 4/2016 |
| WO | 2016/073913 A1 | 5/2016 |
| WO | WO 2016071448 A1 | 5/2016 |
| WO | WO 2016092419 A1 | 6/2016 |
| WO | 2016/115105 A1 | 7/2016 |
| WO | WO 2016111947 A2 | 7/2016 |
| WO | 2016/149613 A2 | 9/2016 |
| WO | 2016/154380 A1 | 9/2016 |
| WO | WO 2016144803 A2 | 9/2016 |
| WO | 2016/161248 A1 | 10/2016 |
| WO | 2016/172214 A1 | 10/2016 |
| WO | WO 2016161270 A1 | 10/2016 |
| WO | 2016/176288 A1 | 11/2016 |

(56) References Cited

FOREIGN PATENT DOCUMENTS

| WO | 2016/176299 A1 | 11/2016 |
| --- | --- | --- |
| WO | 2016/187316 A1 | 11/2016 |
| WO | WO 2016/187316 | * 11/2016 |
| WO | 2017/024073 A1 | 2/2017 |
| WO | 2017/075349 A2 | 5/2017 |
| WO | 2018/013918 A2 | 1/2018 |
| WO | 2018/094275 A1 | 5/2018 |
| WO | 2018/119000 A1 | 6/2018 |
| WO | 2019/055579 A1 | 3/2019 |
| WO | 2019/200243 A1 | 10/2019 |
| WO | 2019/246421 A1 | 12/2019 |
| WO | 2020/077300 A1 | 4/2020 |
| WO | WO 2020092615 A1 | 5/2020 |
| WO | 2020/117988 A1 | 6/2020 |
| WO | 2020/118252 A1 | 6/2020 |
| WO | WO 2020191326 A1 | 9/2020 |
| WO | WO 2021007314 A1 | 1/2021 |
| WO | WO 2021007316 A1 | 1/2021 |

OTHER PUBLICATIONS

Bogenberger et al. Combined venetoclax and alvocidib in acute myeloid leukemia. Oncotarget, 2017, vol. 8, (No. 63), pp. 107206-107222. (Year: 2017).*

Whatcott et al. Alvocidib Potentiates the Activity of Venetoclax in Preclinical Models of Acute Myeloid Leukemia. Blood (2016) 128 (22) : 1652. (Year: 2016).*

Adams et al., "The Bcl-2 Protein Family: Arbiters of Cell Survival," *Science* 257(5381):1322-1326, 1998.

Adlard et al., "Prediction of the response of colorectal cancer to systemic therapy," *The Lancet Oncology* 3:75-82, 2002.

Aït-Ikhlef et al., "The motoneuron degeneration in the wobbler mouse is independent of the overexpression of a Bcl2 transgene in neurons," *Neurosci Lett* 199:163-166, 1995.

Almarzooqi et al., "Comparison of Peripheral Blood versus Bone Marrow Blasts Immunophenotype in Pediatric Acute Leukemias," *Ibnosina Journal of Medicine and Biomedical Sciences*, pp. 195-204, 2011. (10 pages).

Altschul et al., "Gapped BLAST and PSI-BLAST: a new generation of protein database search programs," *Nucleic Acids Res.* 25:3389-3402, 1997.

Arguello et al., "Flavopiridol induces apoptosis of normal lymphoid cells, causes immunosuppression, and has potent antitumor activity in vivo against human leukemia and lymphoma xenografts," *Blood* 97(7):2482-2490, 1998.

Bae et al., "Underphosphorylated BAD interacts with diverse antiapoptotic Bcl-2 family proteins to regulate apoptosis," *Apoptosis* 6:319-330, 2001.

Barretina et al., "The Cancer Cell Line Encyclopedia enables predictive modelling of anticancer drug sensitivity," *Nature* 483(7391):603-601, 2012; Erratum in: *Nature* 492(7428):290, 2012.

Bearss, "Targeting MCL1 dependent cancers by CDK9 inhibition," Abstract for Keynote Address, 9th International Conference on Leukemia and Hematologic Oncology, Oct. 5-6, 2017 London, UK, *J Hematol Thrombo Dis* 5(5 Suppl), 2017. (1 page).

Bearss, "NOXA Priming—Predictive Biomarker For Patients With Acute Myeloid Leukemia To Improve Treatment Outcomes," 2016, retrieved from https://openforum.hbs.org/challenge/precision-medicine/submit-ideas/noxa-priming-predic . . . , 7 pages.

Belikov, "Pharmaceutical chemistry," *High School*, 1:43-47, Moscow, 1993 (English translation attached) (14 pages).

Besbes et al. "First MCL-1-selective BH3 mimetics as potential therapeutics for targeted treatment of cancer," *Cell Death and Disease* 6(7), 2015. (2 pages).

Bible et al., "Cytotoxic Synergy Between Flavopiridol (NSC 649890, L86-8275) and Various Antineoplastic Agents: The Importance of Sequence of Administration," *Cancer Research* 57:3375-3380, 1997.

Blachly et al., "Emerging Drug Profile: Cyclin-Dependent Kinase Inhibitors," *Leuk Lymphoma* 54:2133-2143, 2013. (22 pages).

Bodet et al., "BH3-only protein Bik is involved in both apoptosis induction and sensitivity to oxidative stress in multiple myeloma," *Br. J. Cancer* 705:1808-1814, 2010.

Bogenberger et al., "BCL-2 family proteins as 5-Azacytidine-sensitizing targets and determinants of response in myeloid malignancies," *Leukemia* 28(8):1657-1665, 2014.

Bogenberger et al., "Combined venetoclax and alvocidib in acute myeloid leukemia," *Oncotarget* 8(63):107206-107222, 2017.

Bose et al., "Mcl-1 as a therapeutic target in acute myelogenous leukemia (AML)," *Leukemia Research Reports* 2:12-14, 2013.

Bouillet et al., "Proapoptotic Bcl-2 Relative Bim Required for Certain Apoptotic Responses, Leukocyte Homeostasis, and to Preclude Autoimmunity," *Science* 286:1735-1738, 1999.

Boyd et al., "Bik, a novel death-inducing protein shares a distinct sequence motif with Bcl-2 family proteins and interacts with viral and cellular survival-promoting proteins," *Oncogene* 11(9):1921-1928, 1995.

Brady et al., "Reflections on a peptide," *Nature* 368:692-693, 1994.

Braun et al., "Preclinical Study Of The Bromodomain Inhibitor OTX015 In Acute Myeloid (AML) and Lymphoid (ALL) Leukemias," *Blood* 722:4218, 2013, (5 pages) (Abstract Only).

Brennan et al., "Preparation of Bispecific Antibodies by Chemical Recombination of Monoclonal Immunoglobulin $G_1$ Fragments," *Science* 229:81, 1985, 4 pages.

Brooks et al., "CVT-313, a specific and potent inhibitor of CDK2 that prevents neointimal proliferation," *J. Biol. Chem.* 272(46):29207-29211, 1997.

Brunelle et al., "MCL-1-dependent leukemia cells are more sensitive to chemotherapy than BCL-2-dependent counterparts," *J. Cell. Biol.* 187(3):429-442, 2009.

Brunetto et al., "First-in-human, Pharmacokinetic and Pharmacodynamic Phase I Study of Resminostat, an Oral Histone Deacetylase Inhibitor, in Patients with Advanced Solid Tumors," *Clinical Cancer Research* 19:5494-5504, 2013.

Buccisano et al., "Prognostic and therapeutic implications of minimal residual disease detection in acute myeloid leukemia," *Blood* 119(2):332-341, 2012.

Buggy et al., "CRA-024781: a novel synthetic inhibitor of histone deacetylase enzymes with antitumor activity in vitro and in vivo," *Mol Cancer Ther* 5:1309-1317, 2006.

Buijs et al., "A novel CBFA2 single-nucleotide Mutation in Familial Platelet Disorder with Propensity to Develop Myeloid Malignancies," *Blood* 98(9):2856-2858, 2001.

Buron et al., "Use of human cancer cell lines mitochondria to explore the mechanisms of BH3 peptides and ABT-737-induced mitochondrial membrane permeabilization," *PLoS One* 5(3):e9924, 2010, 13 pages.

Byrd et al., "Chronic Lymphocytic Leukemia," *Hematology*, pp. 163-183, 2004. (21 pages).

Byrd et al., "Flavopiridol Administered as a Pharmacologically-Derived Schedule Demonstrates Marked Clinical Activity in Refractory, Genetically High Risk, Chronic Lymphocytic Leukemia (CLL)," *Blood* 104:341, 2004. (2 pages).

Byrd et al., "Flavopiridol administered using a pharmacologically derived schedule is associated with marked clinical efficacy in refractory, genetically high-risk chronic lymphocytic leukemia," *Blood* 109:399-494, 2007.

Byrd et al., "Flavopiridol Induces Apoptosis in Chronic Lymphocytic Leukemia Cells Via Activation of Caspase-3 Without Evidence of bcl-2 Modulation or Dependence on Functional p53," *Blood* 92:3804-3816, 1998.

Byrd et al., "Sequential Phase II Studies of Flavopiridol by 72-Hour Continuous Infusion and 1-Hour Intravenous Bolus for the Treatment of Relapsed B-Cell Chronic Lymphocytic Leukemia: Results from CALGB Study 19805," *Blood* 104:3485, 2004. (2 pages).

Byrd et al., "Treatment of Relapsed Chronic Lymphocytic Leukemia by 72-Hour Continuous Infusion or 1-Hour Bolus Infusion of Flavopiridol: Results from Cancer and Leukemia Group B Study 19805," *Clin Cancer Res* 11:4176-4181, 2005.

Calin et al., "A MicroRNA Signature Associated with Prognosis and Progression in Chronic Lymphocytic Leukemia," *N. Engl. J. Med.* 353:1793-1801, 2005.

(56) References Cited

OTHER PUBLICATIONS

Carlson et al., "Flavopiridol Induces $G_1$ Arrest with Inhibition of Cyclin-dependent Kinase (CDK) 2 and CDK4 in Human Breast Carcinoma Cells," *Cancer Research* 56:2973-2978, 1996.

Caron et al., "Engineered Humanized Dimeric Forms of IgG Are More Effective Antibodies," *J. Exp. Med.* 176:1191-1195, 1992.

Cartron et al., "The first α Helix of Bax Plays a Necessary Role in Its Ligand-Induced Activation by the BH3-Only Proteins Bid and PUMA," *Mol. Cell.* 16:807-818, 2004.

CAS Registry No. 146426-40-6—Flavopiridol, 1993.

Certo et al., "Mitochondria Primed by Death Signals Determine Cellular Addiction to Antiapoptotic BCL-2 Family Members," *Cancer Cell* 9:351-365, 2006.

Chan et al., "Belinostat and panobinostat (HDACI): in vitro and in vivo studies in thyroid cancer," *J Cancer Res Clin Oncol* 139:1507-1514, 2013.

Chang et al., "Adenovirus-mediated over-expression of the cyclin/cyclin-dependent kinase inhibitor, p21 inhibits vascular smooth muscle cell proliferation and neointima formation in the rat carotid artery model of balloon angioplasty," *J. Clin. Invest.* 96:2260-2268, 1995.

Chao et al., "Flavopiridol Inactivates P-TEFb and Blocks Most RNA Polymerase II Transcription in Vivo," *The Journal of Biological Chemistry* 276:31793-31799, 2001.

Chao et al., "Flavopiridol Inhibits P-TEFb and Blocks HIV-1 Replication," *The Journal of Biological Chemistry* 275:28345-28348, 2000.

Chen et al., "Caspase cleavage of $BIM_{EL}$ triggers a positive feedback amplification of apoptotic signaling," *Proc. Natl. Acad. Sci. USA* 101(5):1235-1240, 2004.

Chen et al., "Downregulation of cyclin-dependent kinase 2 activity and cyclin A promoter activity in vascular smooth muscle cells by p27(KIP1), an inhibitor of neointima formation in the rat carotid artery," *J. Clin. Invest.* 99:2334-2341, 1997.

Chen et al., "Mcl-1 Down-regulation Potentiates ABT-737 Lethality by Cooperatively Inducing Bak Activation and Bax Translocation," *Cancer Res* 67(2):782-791, 2007.

Chen et al., "Differential Targeting of Prosurvival Bcl-2 Proteins by Their BH3-Only Ligands Allows Complementary Apoptotic Function," *Molecular Cell* 17:393-403, 2005.

Chen et al., "Mechanism of action of SNS-032, a novel cyclin-dependent kinase inhibitor in chronic lymphocytic leukemia," *Blood* 113:4637-4645, 2009.

Chen et al., "Transcription inhibition by flavopiridol: mechanism of chronic lymphocytic leukemia cell death," *Blood* 106:2513-2519, 2005.

Cheng et al., "Bax-independent inhibition of apoptosis by $Bcl-x_L$," *Nature* 379:554-556, 1996.

Cheng et al., "BCL-2, $BCL-X_L$ Sequester BH3 Domain-Only Molecules Preventing BAX- and BAK-Mediated Mitochondrial Apoptosis," *Mol. Cell.* 8(3):705-711, 2001.

Cheronis, "Semimicro Experimental Organic Chemistry," deGratt, pp. 67-69 (1958).

Cheson et al., "National Cancer Institute-Sponsored Working Group Guidelines for Chronic Lymphocytic Leukemia: Revised Guidelines for Diagnosis and Treatment," *Blood* 87:4990-4997, 1996.

Chipuk et al., "Direct Activation of Bax by p53 Mediates Mitochondrial Membrane Permeabilization and Apoptosis," *Science* 303:1010-1014, 2004.

Chittenden et al., "A conserved domain in Bak, distinct from BH1 and BH2, mediates cell death and protein binding functions," *EMBO J* 14(22):5589-5596, 1995.

Chittenden et al., "Induction of apoptosis by the Bcl-2 homologue Bak," *Nature* 374(6524):733-736, 1995.

Chonghaile et al., "Mitochondrial Apoptotic Priming Measured by BH3 Profiling Regulates Clinical Response to Chemotherapy in Myeloma and Acute Lymphoblastic Leukemia and Explains Therapeutic Index," Abstract 1442, 53rd ASH Annual Meeting and Exposition, Dec. 10-13, 2011, American Society of Hematology, 6 pages.

Chonghaile et al., "Mimicking the BH3 domain to kill cancer cells," *Oncogene* 27:S149-S157, 2009.

Chonghaile et al., "Pretreatment mitochondrial priming correlates with clinical response to cytotoxic chemotherapy," *Science* 334(6059):1129-1133, 2011.

Chonghaile et al., "Pretreatment mitochondrial priming correlates with clinical response to cytotoxic chemotherapy," *Science* 334(6059):1129-1133, 2011. Supporting Online Material, 36 pages.

Chou et al., "Quantitative Analysis of Dose-Effect Relationships: The Combined Effects of Multiple Drugs or Enzyme Inhibitors," *Advances in Enzyme Regulation* 22:27-40, 1984.

Choudhary et al., "MCL-1 and BCL-xL-dependent resistance to the BCL-2 inhibitor ABT-199 can be overcome by preventing PI3K/AKT/mTOR activation in lymphoid malignancies," *Cell Death and Disease* 6:e1593, 2015. (12 pages).

Clinical Study, "Alvocidib, followed by cytarabine + mitoxantrone, makes impact in AML", *Inpharma Wkly* 1606:8, 2007. (Abstract).

Clowes et al., "Significance of quiescent smooth muscle migration in the injured rat carotid artery," *Circ. Res.* 56(1):139-145, 1985.

Cole et al., "The EBV-Hybridoma technique and its application to human lung cancer," *Monoclonal Antibodies and Cancer Therapy*:77-96, 1985.

Conaway et al., "The Mediator Complex and Transcription Elongation," *Biochim Biophys Acta* 1829:69-75, 2013. (16 pages).

Cory et al., "The Bcl2 Family: Regulators of the Cellular Life-Or-Death Switch," *Nat. Rev. Cancer* 2(9):647-656, 2002.

Cosulich et al., "Regulation of apoptosis by BH3 domains in a cell-free system," *Curr. Biol* 7(12):913-920, 1997.

Cote et al., "Generation of human monoclonal antibiotics reactive with cellular antigens," *Proc. Natl. Acad. Sci. USA* 80:2026-2030, 1983.

Czabotar et al., "Bax Activation by Bim?," *Cell Death and Differentiation* 16:1187-1191, 2009.

Czabotar et al., "Structural insights into the degradation of Mcl-1 induced by BH3 domains," *PNAS* 104:6217-6222, 2007.

Czech et al., "Antitumoral activity of flavone L 86-8275," *International Journal of Oncology* 6:31-36, 1995.

Daigle et al., "Potent Inhibition of DOT1L as Treatment of MLL-fusion Leukemia," *Blood* 122:1017-1025, 2013.

Danial et al., "Cell Death: Critical Control Points," *Cell* 116:205-219, 2004.

Davids et al., "BH3 profiling demonstrates that restoration of apoptotic priming contributes to increased sensitivity to PI3K inhibition in stroma-exposed chronic lymphocytic leukemia cells," *Blood* 118(21): Nov. 18, 2011, Abstract.

Davids et al., "Targeting the B-cell lymphoma/leukemia 2 family in cancer," *J Clin Oncol* 30(25):3127-3135, 2012.

Dawson, et al. "Inhibition of BET recruitment to chromatin as an effective treatment for MLL-fusion leukaemia" *Nature* 478:529-533, 2011.

de Azevedo Jr. et al., "Structural basis for inhibition of cyclin-dependent kinase 9 by flavopiridol," *Biochemical and Biophysical Research Communications* 293:566-571, 2002.

Debrincat et al., "BCL-2 is dispensable for thrombopoiesis and platelet survival," *Cell Death & Disease* 6:e1721, 2015. (8 pages).

Degrado, "Design of peptides and proteins," *Adv. Protein Chem* 39:51-124, 1988.

Deng et al., "BH3 Profiling Identifies Three Distinct Classes of Apoptotic Blocks to Predict Response to ABT-737 and Conventional Chemotherapeutic Agents," *Cancer Cell* 12:171-185, 2007.

Derenne et al., "Antisense strategy shows that Mcl-1 rather than Bcl-2 or $Bcl-x_L$ is an essential survival protein of human myeloma cells," *Blood* 100:194-199, 2002.

Desagher et al., "Bid-induced Conformational Change of Bax Is Responsible for Mitochondrial Cytochrome c Release during Apoptosis," *J. Cell Biol* 144(5):891-901, 1999.

Dettman et al., "Abstract 3400: Mitochondrial profiling in AML patients treated with an Alvocidib containing regimen reveals MCL1 dependency in responder bone marrow," *Cancer Res* 75:3400, 2015. (2 pages).

DeYoung et al., "Gene therapy for restenosis, Are We Ready?" *Circ. Res.* 82:306-313, 1998.

(56) References Cited

OTHER PUBLICATIONS

Di Lisa et al., "Mitochondrial Function and Cell Injury in Single Cardiac Myocytes Exposed to Anoxia and Reoxygenation," *Transplant. Proc.* 27(5):2829-2830, 1995.
Di Lisa et al., "Mitochondrial membrane potential in single living adult rat cardiac myocytes exposed to anoxia or metabolic inhibition," *J. Physiol* 486(1):1-13, 1995.
Diamandis et al., *Immunoassay*, Academic Press, Inc., NY, 1996.
Dinnen et al., "Redirecting Apoptosis to Aponecrosis Induces Selective Cytotoxicity to Pancreatic Cancer Cells through Increased ROS, Decline in ATP Levels, and VDAC," *Molecular Cancer Therapeutics* 12:2792-2803, 2013.
Dohner et al., "Genomic Aberrations and Survival in Chronic Lymphocytic Leukemia," *N. Engl. J. Med.* 343:1910-1916, 2000.
Drees et al., "Flavopiridol (L86-8275): Selective antitumor activity in vitro and activity in vivo for prostate carcinoma cells," *Clin. Cancer Res.* 3:273-279, 1997.
Egle et al., "Bim is a suppressor of Myc-induced mouse B cell leukemia," *Proc. Natl. Acad. Sci USA* 101(16):6164-6169, 2004.
Ellerby et al., "Anti-cancer activity of targeted pro-apoptotic peptides," *Nat. Med.* 5(9):1032-1038, 1999.
Elliott et al., "Intercellular Trafficking and Protein Delivery by a Herpesvirus Structural Protein," *Cell* 88:223-233, 1997.
Elston et al., "Pathological prognostic factors in breast cancer. I. The value of histological grade in breast cancer: experience from a large study with long-term follow-up," *Histopathology* 19:403-410, 1991.
Ember et al., "Acetyl-lysine Binding Site of Bromodomain-Containing Protein 4 (BRD4) Interacts with Diverse Kinase Inhibitors," *ACS Chemical Biology* 9:1160-1171, 2014.
Eskes et al., "Bid Induces the Oligomerization and Insertion of Bax into the Outer Mitochondrial Membrane," *Mol. Cell. Biol.* 20(3):929-935, 2000.
Falkenberg et al., "Histone deacetylases and their inhibitors in cancer, neurological diseases and immune disorders," *Nature Reviews Drug Discovery* 13:673-691, 2014.
Fanidi et al., "Cooperative interaction between c-myc and bcl-2 proto-oncogenes," *Nature* 359:554-556, 1992.
Fernandez et al., "Anthracycline Dose Intensification in Acute Myeloid Leukemia," *New England Journal of Medicine* 361(13):1249-1259, 2009.
Filippakopoulos et al., "Selective inhibition of BET bromodomains," *Nature* 468:1067-1073, 2010.
Filippakopoulos et al., "Targeting bromodomains: epigenetic readers of lysine acetylation," *Nature Reviews Drug Discovery* 13:337-356, 2014.
Fish et al., "Identification of a Chemical Probe for Bromo and Extra C-Terminal Bromodomain Inhibition through Optimization of a Fragment-Derived Hit," *Journal of Medicinal Chemistry* 55:9831-9837, 2012.
Fiskum et al., "Apoptosis-Related Activities Measured with Isolated Mitochondria and Digitonin-Permeabilized Cells," *Methods in Enzymology* 322:222-234, 2000.
Fiskus et al., "Highly Active Combination of BRD4 Antagonist and Histone Deacetylase Inhibitor against Human Acute Myelogenous Leukemia Cells," *Molecular Cancer Therapeutics* 13:1142-1154, 2014.
Flinn et al., "Flavopiridol Administered as a 24-Hour Continuous Infusion in Chronic Lymphocytic Leukemia lacks Clinical Activity," *Leukemia Res* 29:1253-1257, 2005.
Foight et al., "Designed BH3 Peptides with High Affinity and Specificity for Targeting Mcl-1 in Cells," *ACS Chem. Biol.* 9:1962-1968, 2014.
Frankel et al., "Activity of synthetic peptides from the Tat protein of human immunodeficiency virus type 1," *Proc. Natl. Acad. Sci. USA* 86:7397-7401, 1989.
Friedman et al., "Precision medicine for cancer with next-generation functional diagnostics," *Nat Rev Cancer* 15(12):747-756, 2015.
Fuchs et al., "Pathway for Polyarginine Entry into Mammalian Cells," *Biochemistry* 43(9):2438-2444, 2004.

Fukui et al., "The Analysis of the Effect of JQ1 and Flavopiridol on Chondrocytes under Inflammatory Stimuli," ORS 2014 Annual Meeting, 4 pages.
Futaki et al., "Arginine-rich Peptides: An Abundant Source of Membrane-Permeable Peptides Having Potential as Carriers for Intracellular Protein Delivery," *J. Biol. Chem* 276(8):5836-5840, 2001.
Geng et al., "Apoptosis of vascular smooth muscle cells induced by in vitro stimulation with interferon-γ, tumor necrosis factor-α, and interleukin-1β," *Arterioscler. Thromb. Biol* 16:19-27, 1996.
Gerber et al., "Association of acute myeloid leukemia's most immature phenotype with risk groups and outcomes," *Haematologica* 101(5):607-616, 2016. (18 pages).
Geserick et al., "The ratio of Mcl-1 and Noxa determines ABT737 resistance in squamous cell carcinoma of the skin," *Cell Death and Disease* 5:e1412, 2014. (14 pages).
Ghyczy et al., "Electrophilic Methyl Groups Present in the Diet Ameliorate Pathological States Induced by Reductive and Oxidative Stress: A Hypothesis," *British Journal of Nutrition* 85(4):409-414, 2001.
Giles et al., "A Phase I Study of Intravenous LBH589, a Novel Cinnamic Hydroxamic Acid Analogue Histone Deacetylase Inhibitor in Patients with Refractory Hematologic Malignancies," *Clin Cancer Res* 12:4628-4635, 2006.
Gojo et al., "The Cyclin-dependent Kinase Inhibitor Flavopiridol Induces Apoptosis in Multiple Myeloma Cells through Transcriptional Repression and Down-Regulation of Mcl-1," *Clinical Cancer Research* 8:3527-3538, 2002.
Goldsmith et al., "BH3 peptidomimetics potently activate apoptosis and demonstrate single agent efficacy in neuroblastoma," *Oncogene* 25:4525-4533, 2006.
Gores et al., "Selectively targeting Mcl-1 for the treatment of acute myelogenous leukemia and solid tumors," *Genes & Development* 26:305-311, 2012.
Göttlicher et al., "Valproic acid defines a novel class of HDAC inhibitors inducing differentiation of transformed cells," *The EMBO Journal* 20:6969-6978, 2001.
Green et al., "A matter of life and death," *Cancer Cell* 1:19-30, 2002.
Green et al., "The Pathophysiology of Mitochondrial Cell Death," *Science* 305:626-629, 2004.
Green, "Life, Death, BH3 Profiles, and the Salmon Mousse," *Cancer Cell* 12:97-99, 2007.
Griffiths et al., "Cell Damage-induced Conformational Changes of the Pro-Apoptotic Protein Bak In Vivo Precede the Onset of Apoptosis," *J. Cell. B+G186iol.* 144(5):903-914, 1999.
Gross et al., "Enforced dimerization of BAX results in its translocation, mitochondrial dysfunction and apoptosis," *EMBO J* 17(14):3878-3885, 1998.
Gruber et al., "Efficient Tumor Cell Lysis Mediated by a Bispecific Single Chain Antibody Expressed in *Escherichia coli*," *J. Immunol* 152:5368-5374, 1994.
Guha, "Cyclin-dependent kinase inhibitors move into Phase III," *Nature Reviews Drug Discovery* 11:892-894, 2012.
Gul et al., "Apoptotic blocks and chemotherapy resistance: strategies to identify Bcl-2 protein signatures," *Briefings in Functional Genomics and Proteomics* 7(1):27-34, 2008.
Hanahan et al., "Heritable formation of pancreatic β-cell tumours in transgenic mice expressing recombinant insulin/simian virus 40 oncogenes," *Nature* 315:115-122, 1985.
Hanahan et al., "The Hallmarks of Cancer," *Cell* 100:57-70, 2000.
Hans et al., "β-Carbolines induce apoptosis in cultured cerebellar granule neurons via the mitochondrial pathway," *Neuropharmacology* 48:105-117, 2005.
Harada et al., "Survival factor-induced extracellular signal-regulated kinase phosphorylates BIM, inhibiting its association with BAX and proapoptotic activity," *Proc. Natl. Acad. Sci. USA* 101(43):15313-15317, 2004.
Harada et al., "Discovery of potent and orally bioavailable 17β-hydroxysteroid dehydrogenase type 3 inhibitors," *Bioorganic & Medicinal Chemistry* 20:3242-3254, 2012.
Harkevich, "Pharmacology," *Medicine, Third Edition*:51-55, Moscow, 1987 (English translation attached) (10 pages).

(56) References Cited

OTHER PUBLICATIONS

Haws et al., "E1204: Alvocidib Synergizes with Venetoclax in Preclinical Models of Multiple Myeloma," *Hematologica* 102(Suppl. 2):495, 2017. (1 page).
Haws et al., "E881: By an MCL-1-Dependent Mechanism, Alvocidib Potentiates the Activity of Cytarabine and Mitoxantrone when Administered in a Time Sequential Regimen in AML," Hematologica 102(Suppl. 2):362, 2017. (1 page).
Hemann et al., "Evasion of the p53 tumour surveillance network by tumour-derived MYC mutants," *Nature* 436:807-811, 2005.
Hemann et al., "Suppression of tumorigenesis by the p53 target PUMA," *Proc. Natl. Acad. Sci. USA* 101(25):9333-9338, 2004.
Hengartner et al., "C. elegans Cell Survival Gene ced-9 Encodes a functional Homolog of the Mammalian Proto-Oncogene bcl-2," *Cell* 76:665-676, 1994.
Hewings et al., "Optimization of 3,5-Dimethylisoxazole Derivatives as Potent Bromodomain Ligands" *J. Med. Chem.*, 56:3217-3227, 2013.
Hirst et al., "Application of Non-Parametric Regression to Quantitative Structure-Activity Relationships," *Bioorganic & Medicinal Chemistry* 10:1037-1041, 2002.
Hnisz et al., "Super-Enhancers in the Control of Cell Identity and Disease," *Cell* 155:934-947, 2013.
Holinger et al., "Bak BH3 Peptides Antagonize Bcl-$x_L$ Function and Induce Apoptosis through Cytochrome c-independent Activation of Caspases," *J. Biol. Chem.* 274(19):13298-13304, 1999.
Hollenbach et al., "A Comparison of Azacitidine and Decitabine Activities in Acute Myeloid Leukemia Cell Lines," *PLoS One* 5(2):e9001, 2010.
Holliger et al., "Diabodies: Small bivalent and bispecific antibody fragments," *Proc. Natl. Acad. Sci. USA* 90:6444-6448, 1993.
Hoogenboom et al., "By-passing Immunisation. Human Antibodies from Synthetic Repertoires of Germline $V_H$ Gene Segments rearranged in Vitro," *J. Mol. Biol.* 227:381-388, 1992.
Hopp et al., "Prediction of protein antigenic determinants from amino acid sequences," *Proc. Natl. Acad. Sci. USA* 78:3824-3828, 1981.
Hoppel et al., "The action of digitonin on rat liver mitochondria. The effects on enzyme content," *Biochem J.* 107(3):367-375, 1968.
Hourigan et al., "Development of therapeutic agents for elderly patients with acute myelogenous leukemia," *Curr Opin Investig Drugs*, 11(6): 669-677, 2010.
Hsu et al., "Nonionic Detergents Induce Dimerization among Members of the Bcl-2 Family," *J. Biol. Chem* 272(21):13829-13834, 1997.
Huang et al., "BH3-Only Proteins—Essential Initiators of Apoptotic Cell Death," *Cell* 103:839-842, 2000.
Huber et al., "Profile of venetoclax and its potential in the context of treatment of relapsed or refractory chronic lymphocytic leukemia," *Onco. Targets Ther*. 10:645-656, 2017.
Hunter, T., "Braking the cycle," *Cell* 75:839-841, 1993.
Hunter, T., "Protein kinases and phosphatases: The yin and yang of protein phosphorylation and signaling," *Cell* 80:225-236, 1995.
Huse et al., "Generation of a large Combinatorial Library of the Immunoglobulin Repertoire in Phage Lambda," *Science* 246:1275-1281, 1989.
Innocenti et al., "Flavopiridol Metabolism in Cancer Patients Is Associated with the Occurrence of Diarrhea," *Clinical Cancer Research* 6:3400-3405, 2000.
Inohara et al., "*harakiri*, a novel regulator of cell death, encodes a protein that activates apoptosis and interacts selectively with survival-promoting proteins Bcl-2 and Bcl-$X_L$," *EMBO J* 16(7):1686-1694, 1997.
Ishizawa et al., "Mitochondrial Profding of Acute Myeloid Leukemia in the Assessment of Response to Apoptosis Modulating Drugs," *PLoS One* 10:e0138377, 2015, 16 pages.
Itzykson et al., "Predicting the outcome of patients with higher-risk myelodysplastic syndrome treated with hypomethylating agents," *Leukemia & Lymphoma* 53(5):760-762, 2012.

Jackson et al., "Heat shock induces the release of fibroblast growth factor 1 from NIH 3T3 cells," *Proc. Natl. Acad. Sci. USA* 89:10691-10695, 1992.
Jameson et al., "A rationally designed CD4 analogue inhibits experimental allergic encephalomyelitis," *Nature* 368:744-746, 1994.
Ji et al., "A Pharmacokinetic/Pharmacodynamic Model of Tumor Lysis Syndrome in Chronic Lymphocytic Leukemia Patients Treated with Flavopiridol," *Clinical Cancer Resarch* 19(5): 1269-1280, 2013.
Jones et al., "Replacing the complementarity-determining regions in a human antibody with those from a mouse," *Nature* 321:522-525, 1986.
Jonkers et al., "Oncogene addiction: Sometimes a temporary slavery," *Cancer Cell* 6:535-538, 2004.
Kantarjian et al., "Decitabine Improves Patient Outcomes in Myelodysplastic Syndromes," Cancer 106(8): 1794-1803, 2006.
Karp et al., "Phase I and pharmacokinetic study of flavopiridol followed by 1-β-D-arabinofuranosylcytosine and mitoxantrone in relapsed and refractory adult acute leukemias," *Clin. Cancer Res.* 11(23):8403-8412, 2005.
Karp et al., "Randomized phase II study of two schedules of flavopiridol given as timed sequential therapy with cytosine arabinoside and mitoxantrone for adults with newly diagnosed, poor-risk acute myelogenous leukemia," *Haematologica* 97(11):1736-1742, 2012.
Karp et al., "Sequential flavopiridol, cytosine arabinoside, and mitoxantrone: a phase II trial in adults with poor-risk acute myelogenous leukemia," *Clin. Cancer Res.* 13(15 Pt. 1):4467-4473, 2007.
Karp et al., "Timed Sequential Therapy of Acute Leukemia with Flavopiridol: In Vitro Model for a Phase I Clinical Trial," *Clin. Cancer Res.* 9: 307-315, 2003.
Kasper et al., "Targeting MCL-1 sensitizes FLT3-HD-positive leukemias to cytotoxic therapies," *Blood Cancer J* 2,10 pages, 2012.
Kearney et al., "Histopathology of in-stent restenosis in patients with peripheral artery disease," *Circulation* 95:1998-2002, 1997.
Keating et al., "Results of First Salvage Therapy for Patients Refractory to a Fludarabine Regimen in Chronic Lymphocytic Leukemia," *Leuk. Lymph*. 43:1755-1762, 2002.
Keating et al., "Therapeutic role of alemtuzumab (Campath-1H) in patients who have failed fludarabine: results of a large international study," *Blood* 99:3554-3561, 2002.
Kelekar et al., "Bad is a BH3 Domain-Containing Protein that Forms an Inactivating Dimer with Bcl-$x_L$," *Mol. Cell. Biol.* 17(12):7040-7046, 1997.
Kelekar et al., "Bcl-2-family proteins: the role of the BH3 domain in apoptosis," *Trends in Cell Biol* 8:324-330, 1998.
KG-1a, ATCC® CCC-246.1™ ATCC Product Sheet, 3 pages, May 31, 2013.
Kim et al., "Alvocidib Synergizes with Cytarabine and Daunorubicin (7+3) in Preclinical Models of Acute Myeloid Leukemia," EHA Learning Center, May 18, 2017, retrieved from https://learningcenter.ehaweb.org/eha/2017/22nd/180678, 3 pages.
Kim et al., "The CDK9 Inhibitor, Alvocidib, Potentiates the Non-Clinical Activity of Azacytidine or Decitabine in an MCL-1-Dependent Fashion, Supporting Clinical Exploration of a Decitabine and Alvocidib Combination," *Blood* 132(Suppl. 1):4355, 2018, 6 pages.
Kim et al., "TP-1287, an oral prodrug of the cyclin-dependent kinase-9 inhibitor alvocidib", EHA Learning Center, Jun. 9, 2016, retrieved from https://library.ehaweb.org/eha/2016/21st/132440/clifford.whatcott.tp-1287.an.oral.prodrug.of.the.103cyclin-dependent.kinase-9.html, 2 pages.
Kimura, et al. "Antiproliferative and Antitumor Effects of Azacitidine Against Human Myelodysplastic Syndrome Cell Line SKM-1", Anticancer Research, 32:795-798 (2012).
Kitada et al., "Protein kinase inhibitors flavopiridol and 7-hydroxy-staurosporine down-regulate antiapoptosis proteins in B-cell chronic lymphocytic leukemia," *Blood* 96:393-397, 2000.
Kohler et al., "Continuous cultures of fused cells secreting antibody of predefined specificity," *Nature* 256:495-497, 1975.
König et al., "The Novel Cyclin-Dependent Kinase Inhibitor Flavopiridol Downregulates Bcl-2 and Induces Growth Arrest and Apoptosis in Chronic B-Cell Leukemia Lines," *Blood* 90:4307-4312, 1997.

(56) References Cited

OTHER PUBLICATIONS

Korsmeyer et al., "Pro-apoptotic cascade activates BID, which oligomerizes BAK or BAX into pores that result in the release of cytochrome c," *Cell Death Differ* 7(12):1166-1173, 2000.
Kozbor et al., "The production of monoclonal antibodies from human lymphocytes," *Immunol Today* 4:72-79, 1983.
Kryštof et al., "Cyclin-Dependent Kinase Inhibitors as Anticancer Drugs," *Current Drug Targets* 11:291-302, 2010.
Kuwana et al., "BH3 Domains of BH3-Only Proteins Differentially Regulate Bax-Mediated Mitochondrial Membrane Permeabilization Both Directly and Indirectly," *Mol. Cell.* 17:525-535, 2005.
Kuwana et al., "Bid, Bax, and Lipids Cooperate to Form Supramolecular Openings in the Outer Mitochondrial Membrane," *Cell* 111:331-342, 2002.
Kyte et al., "A Simple Method for displaying the Hydropathic Character of a protein," *J. Mol. Biol.* 157:105-132, 1982.
La Vieira et al., "Cell permeable BH3-peptides overcome the cytoprotective effect of Bcl-2 and Bcl-$X_L$," *Oncogene* 21:1963-1977, 2002.
Labi et al., "Targeting the Bcl-2-regulated apoptosis pathway by BH3 mimetics: a breakthrough in anticancer therapy?" *Cell Death and Differentiation* 15:977-987, 2008.
Lazarus et al., "High-Dose Cytosine Arabinoside and Daunorubicin as Primary Therapy in Elderly Patients With Acute Myelogenous Leukemia," *Cancer* 63:1055-1059, 1989.
Lemke et al., "Immunobiology of the TAM Receptors," *Nature Reviews Immunology* 8:327-336, 2008.
Leo et al., "Characterization of the Antiapoptotic Bcl-2 Family Member Myeloid Cell Leukemia-1 (Mcl-1) and the Stimulation of Its Message by Gonadotropins in the Rat Ovary," *Endocrinol* 140:5469-5477, 1999.
Letai et al., "Antiapoptotic BCL-2 is required for maintenance of a model leukemia," *Cancer Cell* 6:241-249, 2004.
Letai et al., "Distinct BH3 domains either sensitize or activate mitochondrial apoptosis, serving as prototype cancer therapeutics," *Cancer Cell* 2:183-192, 2002.
Letai, "Perturbing cancer cell mitochondria to learn how to kill cancer with BH3 profiling," Broad Institute, Seminar Series on Cell Circuits and Epigenomics, Jul. 28, 2014, Presentation, 47 pages.
Letai, "The BCL-2 network: Mechanistic insights and therapeutic potential," *Drug Disc. Today: Disease Mechanisms* 2(2):145-151, 2005.
Letai, "BH3 domains as BCL-2 inhibitors: prototype cancer therapeutics," *Expert Opin. Biol. Ther.* 3:293-304, 2003.
Li et al., "Cleavage of BID by Caspase 8 Mediates the Mitochondrial Damage in the Fas Pathway of Apoptosis," *Cell* 94(4):491-501, 1998.
Li et al., "Endonuclease G is an apoptotic DNase when released from mitochondria," *Nature* 412:95-99, 2001.
Li et al., "tsg101: A Novel tumor susceptibility gene isolated by controlled Homozygous functional knockout of Allelic Loci in Mammalian Cells," *Cell* 85:319-329, 1996.
Lin et al., "Targeting MCL-1/BCL-$X_L$ Forestalls the Acquisition of Resistance to ABT-199 in Acute Myeloid Leukemia," *Scientific Reports* 6(1): 1-10, 2016.
Lin et al., "Flavopiridol given as a 30-min intravenous (IV) bolus followed by 4-hr continuous IV infusion (CIVI) results in clinical activity and tumor lysis in refractory chronic lymphocytic leukemia (CLL)," *Journal of Clinical Oncology, 2004 ASCO Annual Meeting Proceedings (Post-Meeting Edition)* 22(14S):6564, 2004. (1 page).
Lin et al., "Seventy-Two Hour Continuous Infusion Flavopiridol in Relapsed and Refractory Mantle Cell Lymphoma," *Leukemia & Lymphoma* 43:793-797, 2002.
Liu et al., "Bax conformational change is a crucial step for PUMA-mediated apoptosis in human leukemia," *BioChem. Biophys. Res. Commun.* 310(3):956-962, 2003.
Liu et al., "BH3-based Fusion Artificial Peptide Induces Apoptosis and Targets Human Colon Cancer," *Molecular Therapy* 17:1509-1516, 2009.
Liu et al., "CDKI-71, a novel CDK9 inhibitor, is preferentially cytotoxic to cancer cells compared to flavopiridol," *Int. J. Cancer* 130:1216-1226, 2012.
Lonberg et al., "Antigen-specific human antibodies from mice comprising four distinct genetic modifications," *Nature* 368:856-859, 1994.
Long et al., "Optimization and validation of mitochondria-based functional assay as a useful tool to identify BH3-like molecules selectively targeting anti-apoptotic Bcl-2 proteins," *BMC Biotechnol* 13:45, 2013, 10 pages.
Lovén et al., "Selective Inhibition of Tumor Oncogenes by Disruption of Super-Enhancers," *Cell* 153:320-334, 2013. (27 pages).
Lozanski et al., "Alemtuzumab is an effective therapy for chronic lymphocytic leukemia with p53 mutations and deletions," *Blood* 103:3278-3281, 2004.
Lu et al., "Compensatory Induction of MYC Expression by Sustained CDK9 Inhibition via a BRD4-dependent Mechanism," *eLife*, 2015. (26 pages).
Luo et al., "Bid, a Bcl2 interacting protein, mediates cytochrome c release from mitochondria in response to activation of cell surface death receptors," *Cell* 94(4):481-490, 1998.
Lutter et al., "The pro-apoptotic Bcl-2 family member tBid localizes to mitochondrial contact sites," *BMC Cell Biology* 2:22, 2001, 9 pages.
Mann et al., "Cell cycle inhibition preserves endothelial function in genetically engineered rabbit vein grafts," *J. Clin. Invest.* 99(6):1295-1301, 1997.
Marani et al., "Identification of Novel Isoforms of the BH3 Domain Protein Bim which Directly Activate Bax to Trigger Apoptosis," *Mol. Cell. Biol.* 22(11):3577-3589, 2002.
Marks et al., "By-passing Immunization. Human Antibodies from v-gene libraries displayed on phage," *J. Mol. Biol.* 222:581-597, 1991.
Marks et al., "By-passing Immunization: building high affinity human antibodies by chain shuffling," *Bio/Technology* 10:779-783, 1992.
Martin, "Opening the Cellular Poison Cabinet," *Science* 330:1330-1331, 2010.
Mason et al., "The Hypogonadal mouse: reproductive functions restored by gene therapy," *Science* 234:1372-1378, 1986.
Matsushita et al., "A high-efficiency protein transduction system demonstrating the role of PKA in long-lasting long-term potentiation," *J. Neuroscience* 21:6000-6001, 2001.
Matsuzaki, "Why and how are peptide-lipid interactions utilized for self-defence?" *Biochem. Soc. Transactions* 29:598-601, 2001.
McDonnell et al., "bcl-2-Immunoglobulin Transgenic Mice Demonstrate Extended B Cell Survival and Follicular Lymphoproliferation," *Cell* 57:79-88, 1989.
Miller et al., "Therapeutic Strategies to Enhance the Anticancer Efficacy of Histone Deacetylase Inhibitors," *J. Biomed. Biotechnol.* 2011:17 pages, 2011.
Milstein et al., "Hybrid hybridomas and their use in immunohistochemistry," *Nature* 305:537-539, 1983.
Molassiotis et al., "Use of complementary and alternative medicine in cancer patients: A European survey," *Annals of Oncology* 16:655-663, 2005.
Montero et al., "Drug-induced death signaling strategy rapidly predicts cancer response to chemotherapy," *Cell* 160(5):977-989, 2015.
Moore et al., "Chronic lymphocytic leukemia requires BCL2 to sequester prodeath BIM, explaining sensitivity to BCL2 antagonist ABT-737," *J. Clin. Invest.* 117(1):112-121, 2007.
Moore et al., "BH3 profiling—measuring integrated function of the mitochondrial apoptotic pathway to predict cell fate decisions," *Cancer Lett* 332:202-205, 2013. (10 pages).
Morishita et al., "A gene therapy strategy using a transcription factor decoy of the E2F binding site inhibits smooth muscle proliferation in vivo," *Proc. Natl. Acad. Sci. USA* 92:5855-5859, 1995.
Morrison et al., "Success in specification," *Nature* 368:812-813, 1994.

(56) References Cited

OTHER PUBLICATIONS

Motwani et al., "Sequential Dependent Enhancement of Caspase Activation and Apoptosis by Flavopiridol on Paclitaxel-Treated Human Gastric and Breast Cancer Cells," *Clinical Cancer Research* 5(7):1876-1883, 1999.

Muchmore et al., "X-ray and NMR structure of human Bcl-$x_L$, an inhibitor of programmed cell death," *Nature* 381:335-341, 1996.

Munson et al., "Ligand: A Versatile Computerized Approach for Characterization of Ligand-Binding Systems," *Analytical Biochemistry* 107:229-239, 1980.

Murthi et al., "Structure-Activity Relationship Studies of Flavopiridol Analogues," *Bioorganic & Medicinal Chemistry Letters* 10:1037-1041, 2000.

Nagai et al., "Studies on Psychotropic Agents. VI. Synthesis of 1'-Methylspiro[6-fluoroindan-1, 3'-pyrrolidine]-3-one and Related Compounds," *Chem. Pharm. Bull.* 28(5):1387-1393, 1980.

Naik et al., "An Antiinflammatory Cum Immunomodulatory Piperidinylbenzopyranone From *Dysoxylum binectariferum*: Isolation, Structure and Total Synthesis," *Tetrahedron* 44:2081-2086, 1988.

Nakano et al., "PUMA, a Novel Proapoptotic Gene, Is Induced By p53," *Molecular Cell* 7:683-694, 2001.

Narita et al., "Bax interacts with the permeability transition pore to induce permeability transition and cytochrome c release in isolated mitochondria," *Proc. Natl. Acad. Sci. USA* 95:14681-14686, 1998.

Neuberger et al., "Generating high-avidity human Mabs in mice," *Nature Biotechnology* 14:826, 1996.

Nguyen et al., "Azacitidine and decitabine have different mechanisms of action in non-small cell lung cancer cell lines," *Lung Cancer: Targets and Therapy* 1:119-140, 2010.

Noel et al., "Abstract C244: Development of the BET bromodomain inhibitor OTX015," *Molecular Cancer Therapeutics* 12(11): Supplement, 2013.

O'Brien et al., "Phase I to II Multicenter Study of Oblimersen Sodium, a Bcl-2 Antisense Oligonucleotide, in Patients With Advanced Chronic Lymphocytic Leukemia," *J. Clin. Oncol.* 23(30):7697-7702, 2005.

O'Brien et al., "Proliferation in primary and restenotic coronary atherectomy tissue: implications for antiproliferative therapy," *Circ. Res.* 73(2):223-231, 1993.

O'Connor et al., "Bim: a novel member of the Bcl-2 family that promotes apoptosis," *EMBO J* 17(2):384-395, 1998.

Oda et al., "Noxa, a BH3-Only Member of the Bcl-2 Family and Candidate Mediator of p53-Induced Apoptosis," *Science* 288:1053-1058, 2000.

Odore et al., "Abstract LB-231: A phase I pharmacokinetic study of OTX015 for the treatment of patients with hematologic malignancies," *Cancer Research* 74(Supplement 19), 2014. (4 pages) (Abstract Only).

Oh et al., "Conformational Changes in BID, a Pro-apoptotic BCL-2 Family Member, upon Membrane Binding," *J. Biol. Chem.* 280(1):753-767, 2005.

Okamoto et al., "Increased antitumor potential of the raloxifene prodrug, raloxifene diphosphate," *Int. J. Cancer* 122:2142-2147, 2008.

Oltersdorf et al., "An inhibitor of Bcl-2 family proteins induces regression of solid tumours," *Nature* 435:677-681, 2005.

Opferman et al., "Development and maintenance of B and T lymphocytes requires antiapoptotic MCL-1," *Nature* 426:671-676, 2003.

Oppermann et al., "High-content screening identifies kinase inhibitors that overcome venetoclax resistance in activated CLL cells," *Blood* 128(7):934-947, 2016.

Oscier et al., "Multivariate analysis of prognostic factors in CLL: clinical stage, *IGVH* gene mutational status, and loss or mutation of the p53 gene are independent prognostic factors," *Blood* 100:1177-1184, 2002.

Otsuka et al., "Effect of Polymorphic Forms of Bulk Powders on Pharmaceutical Properties of Carbamazepine Granules," *Chem. Pharm. Bull.* 47(6):852-856, 1999.

Paoluzzi et al., "The BH3-only mimetic ABT-737 synergizes the antineoplastic activity of proteasome inhibitors in lymphoid malignancies," *Blood* 112:2906-2916, 2008.

Paquin et al., "Design and synthesis of 4-[(s-triazin-2-ylamino)methyl]-N-(2-aminophenyl)-benzamides and their analogues as a novel class of histone deacetylase inhibitors," *Bioorganic & Medicinal Chemistry Letters* 18:1067-1071, 2008.

Park et al., "Inhibitors of cyclin-dependent kinases promote survival of post-mitotic neuronally differentiated PC12 cells and sympathetic neurons," *J. Biol. Chem.* 271(14):8161-8169, 1996.

Parker et al., "Early Induction of Apoptosis in Hematopoietic Cell Lines After Exposure to Flavopiridol," *Blood* 91:458-465, 1998.

Parry et al., "Dinaciclib (SCH 727965), a Novel and Potent Cyclin-Dependent Kinase Inhibitor," *Molecular Cell Therapy* 9:2344-2353, 2010.

Paruch et al., "Discovery of Dinaciclib (SCH 727965): A Potent and Selective Inhibitor of Cyclin-Dependent Kinases," *ACS Medicinal Chemistry Letters* 1:204-208, 2010.

Payne et al., "Identification of the regulatory phosphorylation sites in pp42/mitogen-activated protein kinase (MAP kinase)," *The EMBO Journal* 10(4):885-892, 1991.

Pepper et al., "Flavopiridol circumvents Bcl-2 family mediated inhibition of apoptosis and drug resistance in B-cell chronic lymphocytic leukaemia," *Br. J. Haematol* 114(1):70-77, 2001.

Perkins et al., "Frequency and Type of Serious Infections in Fludarabine-Refractory B-Cell Chronic Lymphocytic Leukemia and Small Lymphocytic Lymphoma," *Cancer* 94:2033-2039, 2002.

Phillips et al., "Loss in MCL-1 function sensitizes non-Hodgkin's lymphoma cell lines to the BCL-2-selective inhibitor venetoclax (ABT-199)," *Blood Cancer J.* 5:e368, 2015, (8 pages).

Picaud et al., "PFI-1, a Highly Selective Protein Interaction Inhibitor Targeting BET Bromodomains," *Cancer Research* 73:3336-3346, 2013.

Piekarz et al., "Inhibitor of histone deacetylation, depsipeptide (FR901228), in the treatment of peripheral and cutaneous T-cell lymphoma: a case report," *Blood* 98:2865-2868, 2001.

Pierceall et al., "BH3 Profiling Discriminates Response to Cytarabine-Based Treatment of Acute Myelogenous Leukemia," *Mol. Cancer. Ther.* 12(12):2940-2949, 2013.

Pierceall et al., "Mcl-1 Dependence Predicts Response to Vorinostat and Gemtuzumab Ozogamicin in Acute Myeloid Leukemia," *Leuk Res* 38:564-568, 2014, (13 pages).

Pierceall et al., "Mitochondrial Priming of Chronic Lymphocytic Leukemia Patients Associates Bcl-$x_L$ Dependence with Alvocidib Response," *Leukemia* 28:2251-2254, 2014. (7 pages).

Pinckert et al., "An albumin enhancer located 10 kb upstream functions along with its promoter to direct efficient, liver-specific expression in transgenic mice," *Genes and Dev* 1:268-216, 1987.

Plumb et al., "Pharmacodynamic Response and Inhibition of Growth of Human Tumor Xenografts by the Novel Histone Deacetylase Inhibitor PXD101," *Molecular Cancer Therapeutics* 2:721-728, 2003.

Pode-Shakked et al., "Developmental tumourigenesis: NCAM as a putative marker for the malignant renal stem/progenitor cell population," *J. Cell. Mol. Med.* 13(8b):1792-1808, 2009.

Polster et al., "BH3 Death Domain Peptide Induces Cell Type-selective Mitochondrial Outer Membrane Permeability," *The Journal of Biological Chemistry* 276:37887-37894, 2001.

Presta, "Antibody engineering," *Curr. Op. Struct. Biol.* 2:593-596, 1992.

Pritzker, "Cancer Biomarkers: Easier Said Than Done," *Clinical Chemistry* 48:1147-1150, 2002.

Putcha et al., "Induction of BIM, a Proapoptotic BH3-Only BCL-2 Family Member, is Critical for Neuronal Apoptosis," *Neuron* 29(3):615-628, 2001.

Puthalakath et al., "Bmf: A Proapoptotic BH3-Only Protein Regulated by Interaction with the Myosin V Actin Motor Complex, Activated by Anoikis," *Science* 293:1829-1832, 2001.

Puthalakath et al., "Keeping killers on a tight leash: transcriptional and post-translational control of the pro-apoptotic activity of BH3-only proteins," *Cell Death Differ.* 9:505-512, 2002.

(56) References Cited

OTHER PUBLICATIONS

Puthalakath et al., "The Proapoptotic Activity of the Bcl-2 Family Member Bim is Regulated by Interaction with the Dynein Motor Complex," *Mol. Cell.* 3:287-296, 1999.

Qi et al., "Abstract 2016: A subset of small cell lung cancer (SCLC) cell lines is Mcl-1-dependent and responds to cyclin-dependent kinase (cdk)9 inhibition in vitro and in vivo", *Cancer Research* 72:8 Suppl. 1, Abstract 2016, 2012. (4 pages).

Quinsay et al., "Abstract 1783: Proapoptotic Bnip3 Mediates Permeabilization of Mitochondria and Release of Cytochrome c via a Novel Mechanism," *Circulation* 118(18): Supply 2, S388, 2008—Abstract.

Raff, "Social controls on cell survival and cell death," *Nature* 356:397-499, 1992.

Rassenti et al., "ZAP-70 Compared with Immunoglobulin Heavy-Chain Gene Mutation Status as a Predictor of Disease Progression in Chronic Lymphocytic Leukemia," *N. Engl. J. Med.* 351:893-901, 2004.

Ravandi et al., "Evaluating measurable residual disease in acute myeloid leukemia," *Blood Adv.* 2(11):1356-1366, 2018. (23 pages).

Ray et al., "BNIP3 Heterodimerizes with Bcl-2/Bcl-$x_L$ and Induces Cell Death Independent of a Bcl-2 Homology 3 (BH3) Domain at Both Mitochondrial and Nonmitochondrial Sites," *J. Biol. Chem.* 275(2):1439-1448, 2000.

Raychaudhuri, "Low probability Bid-Bax reaction generates heterogeneity in apoptosis resistance of cancer and cancer stem cells," arXiv:1108.2091 [q-bio.MN], 2011.

Ren et al., "BID, BIM, and PUMA Are Essential for Activation of the BAX- and BAK-Dependent Cell Death Program," *Science* 330:1390-1393, 2010.

Rezaei et al., "Leukemia markers expression of peripheral blood vs. bone marrow blasts using flow cytometry," *Med Sci. Monit* 9:CR359-CR362, 2003.

Richon et al., "A class of hybrid polar inducers of transformed cell differentiation inhibits histone deacetylases," *Proc. Natl. Acad. Sci. USA* 95:3003-3007, 1998.

Riechmann et al., "Reshaping human antibodies for therapy," *Nature* 332:323-327, 1988.

Rollins-Raval et al., "The value of immunohistochemistry for CD14, CD123, CD33, myeloperoxidase and CD68R in the diagnosis of acute and chronic myelomonocytic leukaemias," *Histopathology* 60:933-942, 2012.

Rothbard et al., "Conjugation of arginine oligomers to cyclosporine A facilitates topical delivery and inhibition of inflammation," *Nat. Med.* 6(11):1253-1257, 2000.

Rudek et al., "Clinical Pharmacology of Flavopiridol Following a 72-Hour Continuous Infusion," *Ann Pharmacother* 37:1369-1374, 2003.

Ruef et al., "Flavopiridol Inhibits Smooth Muscle Cell Proliferation In Vitro and Neointimal Formation In Vivo After Carotid Injury in the Rat," *Circulation* 100(6):659-665, 1999.

Ruef et al., "Induction of rat aortic smooth muscle cell growth by the lipid peroxidation product 4-hydroxy-2-nonenal," *Circulation* 97:1071-1078, 1998.

Ruef et al., "Induction of vascular endothelial growth factor in balloon-injured baboon arteries," *Circ. Res.* 81:24-33, 1997.

Ryan et al., "Heightened mitochondrial priming is the basis for apoptotic hypersensitivity of CD4+ CD8+ thymocytes," *Proc. Natl. Acad. Sci USA* 107(29):12895-12900, 2010.

Ryan et al., "BH3 Profiling in Whole Cells by Fluorimeter or FACS," *Methods* 61:156-164, 2013. (22 pages).

Saito et al., "A synthetic inhibitor of histone deacetylase, MS-27-275, with marked in vivo antitumor activity against human tumors," *Proc. Natl. Acad. Sci. USA* 96:4592-4597, 1999.

Samson et al., "A 35 amino acid fragment of leptin inhibits feeding in the rat," *Endocrinology* 137:5182-5185, 1996.

Sata et al., "Fas ligand gene transfer to the vessel wall inhibits neointima formation and overrides the adenovirus-mediated T cell response," *Proc. Natl. Acad. Sci. USA* 95:1213-1217, 1998.

Sattler et al., "Structure of Bcl-$x_L$-Bak Peptide Complex: Recognition Between Regulators of Apoptosis," *Science* 275:983-986, 1997.

Sausville et al., "Inhibition of CDKs as a Therapeutic Modality," *Ann NY Acad of Sci* 910:207-222, 2000.

Schimmer et al., "The BH3 domain of BAD fused to the Antennapedia peptide induces apoptosis via its alpha helical structure and independent of Bcl-2," *Cell Death and Differentiation* 8:725-733, 2001.

Schwartz et al., "Phase II Study of the Cyclin-Dependent Kinase Inhibitor Flavopiridol Administered to Patients With Advanced Gastric Carcinoma," *J. Clin. Onc.* 19:1985-1992, 2001.

Schwartz et al., "The intima: soil for atherosclerosis and restenosis," *Circ. Res.* 77:445-465, 1995.

Score, "Search Results Details for U.S. Appl. No. 11/789,557 and Search Result 20091106_104627_ . . . ," Nov. 24, 2009, URL= http://es/ScoreAccessWeb/GetItem.action?AppId=11789557&seqId=09323b6780cf451a&ItemN . . . , 4 pages.

Seal et al., "Identification of a novel series of BET family bromodomain inhibitors: binding mode and profile of I-BET151 (GSK1210151A)," *Bioorg. Med. Chem. Lett* 22:2968-2972, 2012.

Sedlacek et al., "Flavopiridol (L86 8275; NSC 649890), a new kinase inhibitor for tumor therapy," *International Journal of Oncology* 9:1143-1168, 1996.

Sen et al., "Artemisinin triggers induction of cell-cycle arrest and apoptosis in *Leishmania donovani* promastigotes," *J Med Microbiol* 56(Pt. 9):1213-1218, 2007.

Senderowicz et al., "Phase I Trial of Continuous Infusion Flavopiridol, a Novel Cyclin-Dependent Kinase Inhibitor, in Patients with Refractory Neoplasms," *J. Clin Onc* 16:2986-2999, 1998.

Senderowicz et al., "Preclinical and Clinical Development of Cyclin-Dependent Kinase Modulators," *J Natl Cancer Inst* 92:376-387, 2000.

Senderowicz, "Flavopiridol: the first cyclin-dependent kinase inhibitor in human clinical trials," *Investigational New Drugs* 17:313-320, 1999.

Shalaby et al., "Development of humanized bispecific antibodies reactive with cytotoxic lymphocytes and tumor cells overexpressing the HER2 protooncogene," *J Exp. Med.* 175:217-225, 1992.

Shangary et al., "Peptides derived from BH3 domains of Bcl-2 family members: a comparative analysis of inhibition of Bcl-2, Bcl-$x_L$ and Bax oligomerization, induction of cytochrome c release, and activation of cell death," *Biochemistry* 41:9485-9495, 2002.

Shapiro et al., "A Phase II Trial of the Cyclin-dependent Kinase Inhibitor Flavopiridol in Patients with Previously Untreated Stage IV Non-Small Cell Lung Cancer," *Clinical Cancer Research* 7:1590-1599, 2001.

Shibue et al., "Differential contribution of Puma and Noxa in dual regulation of p53-mediated apoptotic pathways," *The EMBO Journal* 25:4952-4962, 2006.

Shimizu et al., "Proapoptotic BH3-only Bcl-2 family members induce cytochrome c release, but not mitochondrial membrane potential loss, and do not directly modulate voltage-dependent anion channel activity," *PNAS* 97:577-582, 2000.

Shopes, "A genetically engineered human IgG mutant with enhanced cytolytic activity," *J. Immunol* 148:2918-2922, 1992.

Sinicrope et al., "Proapoptotic Bad and Bid Protein Expression Predict Survival in Stages II and III Colon Cancers," *Clin. Canc. Res.* 14(13):4128-4133, 2008.

Sinicrope et al., "Prognostic Impact of Bim, Puma, and Noxa Expression in Human Colon Carcinomas," *Clin. Canc. Res.* 14(18):5810-5818, 2008.

Sirois et al., "Antisense oligonucleotide inhibition of PDGFR-beta receptor subunit expression directs suppression of intimal thickening," *Circulation* 95:669-616, 1997.

Smith et al., "Abstract P047: Real-World Outcomes Among AML Patients Treated With Decitabine or Azacitidine," *Haematologica* 98(Suppl 1):19, 2013.

Smith et al., "An alvocidib-containing regimen is highly effective in AML patients through a mechanism dependent on MCL1 expression and function," *Journal of Clinical Oncology* 33(15 Suppl.): Abstract No. 7062, 2015 (3 pages).

Smith et al., "Enhancer biology and enhanceropathies," *Nature Structural & Molecular Biology* 21:210-219, 2014.

(56) References Cited

OTHER PUBLICATIONS

Soltow et al., "Overexpression of CuZnSOD or MnSOD protects satellite cells from doxorubicin-induced apoptosis," *FASEB J* 21:A449, 2007—Abstract.

Song et al., "Application of Flavopiridol, Novel Small Molecule Cyclin-Dependent Kinase Inhibitor, in Tumor Therapy" *National Medical Journal of China* 85(12): 862-864, 2005. (With English Translation) (10 Pages).

Song et al., "Carbon Monoxide Promotes Fas/CD95-Induced Apoptosis in Jurkat Cells," *J. Biol Chem* 279(43):44327-44334, 2004—"Additions and Corrections," *J. Biol Chem* 280(23):22555-22556, 2005.

Song et al., "Carbon monoxide promotes Fas/CD95-induced apoptosis in Jurkat cells," *J. Biol Chem* 279(43):44327-44334, 2004. Erratum in: *J Biol Chem* 280(23):22555-22556, 2005.

Stephens et al., "Cyclophosphamide, alvocidib (flavopiridol), and rituximab, a novel feasible chemoimmunotherapy regimen for patients with high-risk chronic lymphocytic leukemia", *Leukemia Research* 37:1195-1199, 2013.

Stevenson et al., "A chimeric antibody with dual Fc regions (bisFabFc) prepared by manipulations at IgG hinge," *Anti-Cancer Drug Design* 3:219-230, 1989.

Stewart et al., "The MCL-1 BH3 Helix is an Exclusive MCL-1 inhibitor and Apoptosis Sensitizer," *Nat. Chem. Biol.* 6(8):595-601, 2010.

Sturm et al., "Mutation of p53 and consecutive selective drug resistance in B-CLL occurs as a consequence of prior DNA-damaging chemotherapy," *Cell Death and Differentiation* 10:477-484, 2003.

Sugiyama et al., "Activation of mitochondrial voltage-dependent anion channel by a pro-apoptotic BH3-only protein Bim," *Oncogene* 21(32):4944-4956, 2002.

Suzuki et al., "Possible Existence of Common Internalization Mechanisms among Arginine-rich Peptides," *J. Biol Chem* 277:2437-2443, 2002.

Tahir et al., "Potential mechanisms of resistance to venetoclax and strategies to circumvent it," *BMC Cancer* 17:399, 2017. (10 pages).

Tan et al., "Phase I Clinical and Pharmacokinetic Study of Flavopiridol Administered as a Daily 1-Hour Infusion in Patients with Advanced Neoplasms," *J Clin Oncol* 20:4074-4082, 2002.

Tan et al., "The DNA methyltransferase inhibitor zebularine induces mitochondria-mediated apoptosis in gastric cancer cells in vitro and in vivo," *Biochemical and Biophysical Research Communications* 430:250-255, 2013.

Taussig et al., "Anti-CD38 antibody-mediated clearance of human repopulating cells masks the heterogeneity of leukemia-initiating cells," *Blood* 112(3):568-575, 2008.

Terradillos et al., "Direct addition of BimL to mitochondria does not lead to cytochrome c release," *FEBS Lett* 522(1-3):29-34, 2002.

Theisen et al., "Reversible inhibition of lysine specific demethylase 1 is a novel anti-tumor strategy for poorly differentiated endometrial carcinoma," *BMC Cancer* 14:752, 2014, 12 pages.

Thomas et al., "Phase I Clinical and Pharmacokinetic Trial of the Cyclin-Dependent Kinase Inhibitor Flavopiridol," *Cancer Chemother Pharmacol* 50:465-472, 2002.

Thomas et al., "Phase I Clinical and Pharmocokinetic Trial of Flavopiridol," *Proc of Annual Meeting of Amer Assoc* 38:Abstract 1496, 222, 1997.

Thomenius et al., "Using BH3 Profiling As a Predictive Indicater for Myeloma Patient Response to Bortezomib," *Blood* 118(21): Abstract No. 3952, 2011.

Thornton et al., "Characterisation of TP53 abnormalities in chronic lymphocytic leukaemia," *The Hematology Journal* 5:47-54, 2004.

Thornton et al., "High dose methylprednisolone can induce remissions in CLL patients with p53 abnormalities," *Ann Hematol* 82:759-765, 2003.

Tolero Pharmaceuticals, "Jefferies 2016 Heathcare Conference," 2016, 31 pages.

Toogood et al., "Discovery of a Potent and Selective Inhibitor of Cyclin-Dependent Kinase 4/6," *J. Med. Chem.* 48:2388-2406, 2005.

Touzeau et al., "BH3-profiling identifies heterogeneous dependency on Bcl-2 family members in multiple myeloma and predicts sensitivity to BH3 mimetics," *Leukemia* 30:761-764, 2016.

Traunecker et al., "Bispecific single chain molecules (Janusins) target cytotoxic lymphocytes on HIV infected cells," *EMBO J* 10:3655-3659, 1991.

Tsao et al., "Concomitant inhibition of DNA methyltransferase and BCL-2 protein function synergistically induce mitochondrial apoptosis in acute myelogenous leukemia cells," *Ann Hematol* 91(12):1861-1870, 2012.

Tutt et al., "Trispecific F(ab')$_3$ derivatives that use cooperative signaling via the TCR/CD3 complex and CD2 to activate and redirect resting cytotoxic T cells," *J. Immunol* 147:60-69, 1991.

U.S. National Library of Medicine, "Alvocidib, Cytarabine, and Mitoxantrone in Treating Patients With Newly Diagnosed Acute Myeloid Leukemia" Nov. 21, 2008, URL=https://clinicaltrials.gov/ct2/show/NCT00795002, retrieved Jan. 28, 2020, 11 pages.

U.S. National Library of Medicine, "Flavopiridol in Treating Patients With Previously Treated Chronic Lymphocytic Leukemia or Lymphocytic Lymphoma," Apr. 9, 2003, URL=https://www.clinicaltrials.gov/ct2/show/NCT00058240?term=alvocidib&rank=16, retrieved Dec. 11, 2018, 8 pages.

U.S. National Library of Medicine, "Flavopiridol in Treating Patients With Relapsed or Refractory Lymphoma or Multiple Myeloma," Jun. 3, 2005, URL=https://www.clinicaltrials.gov/ct2/show/record/NCT00112723?term=alvocidib&rank=8, retrieved Dec. 11, 2018, 13 pages.

U.S. National Library of Medicine, "History of Changes for Study: NCT01949883 A Phase 1 Study Evaluating CP1-0610 in Patients With Progressive Lymphoma" ClinicalTrials.gov Identifier: NCT01949883, First Posted Sep. 13, 2013, Last Update Posted Sep. 25, 2019, retrieved from https://clinicaltrials.gov/ct2/history/NCT01949883?A=2&B=2&C=merged#StudyPageTop, 7 pages.

U.S. National Library of Medicine, "Ph I Study of Alvocidib and Cytarabine/Daunorubicin (7+3) in Patients With Newly Diagnosed Acute Myeloid Leukemia (AML)," ClinicalTrials.gov Identifier: NCT03298984, First Posted Oct. 2, 2017, Last Update Posted Mar. 14, 2019, retrieved from https://clinicaltrials.gov/ct2/show/study/NCT03298984, 9 pages.

Valencia et al., "A new reliable fluorescence in situ hybridization method for identifying multiple specific cytogenetic abnormalities in acute myeloid leukemia," *Leukemia & Lymphoma* 51(4):680-685, 2010.

Vaquero et al., "Extracellular matrix proteins protect pancreatic cancer cells from death via mitochondrial and nonmitochondrial pathways," *Gastroenterology* 125(4):1188-1202, 2003.

Vaux et al., "Bcl-2 gene promotes haemopoietic cell survival and cooperates with c-myc to immortalize pre-B cells," *Nature* 335(6189):440-442, 1988.

Venkat, "Flavopiridol: A Drug that May Save Lives," 2004, retrieved from https://web.archive.org/web/20060615112217/http://clltopics.org/Chemo/flavopiridol.htm, 7 pages.

Venugopal et al., "A Phase I Study of Quisinostat (JNJ-26481585), an Oral Hydroxamate Histone Deacetylase Inhibitor with Evidence of Target Modulation and Antitumor Activity, in Patients with Advanced Solid Tumors," *Clinical Cancer Research* 19:4262-4272, 2013.

Verhoeyen et al., "Reshaping Human Antibodies: Grafting an Antilysozyme Activity," *Science* 239:1534-1536, 1988.

Ververis et al., "Histone deacetylase inhibitors (HDACIs): multitargeted anticancer agents," *Biologies: Targets and Therapy* 7:47-60, 2013.

Villela et al., "Acute Myeloid Leukaemia: Optimal Management and Recent Developments," *Drugs* 71(12):1537-1550, 2011.

Vitetta et al., "Redesigning Nature's Poisons to Create Anti-Tumor Reagents," *Science* 238:1098-1104, 1987.

Vives et al., "A Truncated HIV-1 Tat Protein Basic Domain Rapidly Translocates through the Plasma Membrane and Accumulates in the Cell Nucleus," *J. Biol. Chem.* 272(25):16010-16017, 1997.

Vo et al., "Relative Mitochondrial Priming of Myeloblasts and Normal HSCs Determines Chemotherapeutic Success in AML," *Cell* 151:344-355, 2012.

(56) References Cited

OTHER PUBLICATIONS

Vo, "Mitochondrial Priming Determines Chemotherapeutic Response in Acute Myeloid Leukemia," Dissertation, Harvard University, 119 pages, Apr. 5, 2012.
Wang et al., "Bid: A Novel BH3 Domain-Only Death Agonist," *Genes & Development* 10(22):2859-2869, 1996.
Wang et al., "Cell Permeable Bcl-2 binding peptides: A Chemical Approach to Apoptosis Induction in Tumor Cells," *Cancer Res.* 60:1498-1502, 2000.
Wang et al., "Structure based discovery of an organic compound that binds Bcl-2 protein and induces apoptosis of tumor cells," *PNAS* 97:7124-7129, 2000.
Wang et al., "Synthesis of pochoxime prodrugs as potent HSP90 inhibitors," *Bioorganic & Medicinal Chemistry Letters* 19:3836-3840, 2009.
Wang, "The Expanding Role of Mitochondria in Apoptosis," *Genes Dev* 15:2922-2933, 2001.
Wei et al., "Proapoptotic BAX and BAK: A Requisite Gateway to Mitochondrial Dysfunction and Death," *Science* 292(5517):727-730, 2001.
Wei et al., "tBID, a membrane-targeted death ligand, oligomerizes BAK to release cytochrome c," *Genes & Development* 14:2060-2071, 2000.
Wei et al., "Temporally and spatially coordinated expression of cell cycle regulatory factors after angioplasty," *Circ. Res.* 80:418-426, 1997.
Weinstein et al., "Addiction to Oncogenes—the Achilles Heal to Cancer," *Science* 297:63-64, 2002.
Weniger et al., "Treatment-Induced Oxidative Stress and Cellular Antioxidant Capacity Determine Response to Bortezomib in Mantle Cell Lymphoma," *Clin. Cancer Res.* 17(15):5101-5112, 2011.
Werner et al., "Bcl-2 Family Member Bfl-1/A1 Sequesters Truncated Bid to Inhibit its Collaboration With Pro-Apoptotic Bak or Bax," *J. Biol. Chem* 277(25):22781-22788, 2002.
Westerhoff et al., "Magainins and the disruption of membrane-linked free-energy transduction," *Proc. Natl. Acad. Sci USA* 86(17):6597-6601, 1989.
Whatcott et al., "Alvocidib Potentiates the Activity of Venetoclax in Preclinical Models of Acute Myeloid Leukemia," *Blood* 128(22):1652, 2016.
Wilkinson, "Immunochemical techniques inspire development of new antibody purification methods," *The Scientist* 14(8):25-28, 2000.
Willis et al., "Apoptosis Initiated When BH3 Ligands Engage Multiple Bcl-2 Homologs, not Bax or Bak," *Science* 315:856-859, 2007.
Willis et al., "Proapoptotic Bak is sequestered by Mcl-1 and Bcl-xL, but not Bcl-2, until displaced by BH3-only proteins," *Genes Dev.* 19:1294-1305, 2005.
Wolff et al., "Monoclonal antibody homodimers: Enhanced antitumor activity in Nude Mice," *Cancer Research* 53:2560-2565, 1993.
Wolter et al., "Movement of Bax from the Cytosol to Mitochondria during Apoptosis," *J. Cell. Biol* 139(5):1281-1292, 1997.
Worland et al., "Alteration of the Phosphorylation State of p34cdc2 Kinase by the Flavone L86-8275 in Breast Carcinoma Cells: Correlation with Decreased H1 Kinase Activity," *Biochem. Pharmacol* 46:1831-1840, 1993.
Woyach et al., "Targeted therapies in CLL: mechanisms of resistance and strategies for management," *Blood* 126:471-477, 2015.
Wyatt et al., "Identification of N-(4-Piperidinyl)-4-(2,6-dichlorobenzoylamino)-1H-pyrazole-3-carboxamide (AT7519), a Novel Cyclin Dependent Kinase Inhibitor Using Fragment-Based X-Ray Crystallography and Structure Based Drug Design," *J. Med. Chem.* 51:4986-4999, 2008.
Yamaguchi et al., "Bcl-XL Protects BimEL-induced Bax Conformational Change and Cytochrome c Release Independent of Interacting with Bax or BimEL," *J. Biol. Chem* 277(44):41604-41612, 2002.
Yamauchi, "Incorporation of novel agents into the treatment for acute myeloid leukemia," *Rinsho Ketsueki* 59(10):1988-1996, 2018. (1 page) (English Abstract Only).
Yang et al., "Bad, a Heterodimeric Partner for Bcl-XL and Bcl-2, Displaces Bax Promotes Cell Death," *Cell* 80:285-291, 1995.
Yang et al., "Calculation of Protein Conformation from Circular Dichroism," *Methods Enzymol* 130:208-269, 1986.
Yang et al., "A novel liposomal formulation of flavopiridol," *International Journal of Pharmaceutics* 365:170-174, 2009.
Yang et al., "Bone marrow stroma-mediated resistance to FLT3 inhibitors in FLT3-ITD AML is mediated by persistent activation of extracellular regulated kinase," *British Journal of Haematology* 164:61-72, 2014.
Yasuda et al., "BNIP3α: a Human Homolog of Mitochondrial Proapoptotic protein BNIP3," *Cancer Res.* 59:533-537, 1999.
Yeh et al., "Up-regulation of CDK9 kinase activity and Mcl-1 stability contributes to the acquired resistance to cyclin-dependent kinase inhibitors in leukemia," *Oncotarget* 6(5):2667-2679, 2014.
Yi et al., "Inhibition of Bid-induced apoptosis by Bcl-2. tBid insertion, Bax translocation, and Bax/Bak oligomerization suppressed," *J. Biol. Chem.* 278(19):16992-16999, 2003.
Yu et al., "Catalytic Site Remodelling of the DOT1L Methyltransferase by Selective Inhibitors," *Nat Commun* 3:1288, 2012.
Zeidner et al., "Randomized multicenter phase II study of flavopiridol (alvocidib), cytarabine, and mitoxantrone (FLAM) versus cytarabine/daunorubicin (7+3) in newly diagnosed acute myeloid leukemia," *Haematologica* 100(9):1172-1179, 2015.
Zeidner, et al., "Randomized Phase II Trial of Timed-Sequential Therapy (TST) with Flavopiridol (Alvocidib), Ara-C and Mitoxantrone (FLAM) Versus "7+3" for Adults Ages 70 Years and Under with Newly Diagnosed Acute Myeloid Leukemia (AML)," *Blood* 120:21, Abstract 47, 5 pages, 2012.
Zeng et al., "Targeting the leukemia microenvironment by CXCR4 inhibition overcomes resistance to kinase inhibitors and chemotherapy in AML," *Blood* 113:6215-6224, 2009.
Zha et al., "BH3 Domain of BAD is Required for Heterodimerization with Bcl-XL and Pro-apoptotic Activity," *J. Biol. Chem.* 272(39):24101-24104, 1997.
Zha et al., "Posttranslational N-Myristoylation of BID as a Molecular Switch for targeting Mitochondria and Apoptosis," *Science* 290(5497):1761-1765, 2000.
Zha et al., "Serine Phosphorylation of Death Agonist BAD in Response to Survival Factor Results in Binding to 14-3-3 Not BCL-XL," *Cell* 87:619-628, 1996.
Zhai et al., "Clinical pharmacology and pharmacogenetics of flavopiridol 1-h i.v. infusion in patients with refractory neoplasms," *Anti-Cancer Drugs* 14:125-135, 2003.
Zhang et al., "Bcl-2 family proteins are essential for platelet survival," *Cell Death Differ.* 14(5):943-951, 2007.
Zhao et al., "The Making of I-BET762, a BET Bromodomain Inhibitor Now in Clinical Development," *Journal of Medicinal Chemistry* 56:7498-7500, 2013.
Zhou et al., "Flavopiridol enhances ABT-199 sensitivity in unfavourable-risk multiple myeloma cells in vitro and in vivo," *Br. J. Cancer* 118(3):388-397, 2018.
Zhou et al., "Novel mutant-selective EGFR kinase inhibitors against EGFR T790M," *Nature* 462(7276):1070-1074, 2009.
Zhu et al., "Development of venetoclax for therapy of lymphoid malignancies," *Drug Des. Devel. Ther.* 11:685-694, 2017.
Zong et al., "BH3-only proteins that bind pro-survival Bcl-2 family members fail to induce apoptosis in the absence of Bax and Bak," *Genes & Development* 15:1481-1486, 2001.
"Alvocidib Biomarker-driven Phase 2 AML Study" Sumitomo Dainippon Pharma Oncology, ClinicalTrials.gov identifier: NTC02520011, URL:https://www.clinicaltrials.gov/ct2/show/NCT02520011, Accessed: Dec. 31, 2020, 8 pages.
"Common Terminology Criteria for Adverse Events, Version 5.0" National Cancer Institute, National Institutes of Health, U.S. Department of Health and Human Services, Published: Nov. 27, 2017, URL=https://ctep.cancer.gov/protocoldevelopment/electronic_applications/docs/CTCAE_v5_Quick_Reference_8.5x11.pdf, Accessed: Dec. 31, 2020, 147 pages.
"Hematologic Malignancies: Regulatory Considerations for Use of Minimal Residual Disease in Development of Drug and Biological Products for Treatment, Guidance For Industry," U.S. Department of Health and Human Services, Food and Drug Administration,

(56) References Cited

OTHER PUBLICATIONS

Oncology Center of Excellence (OCE), Center for Drug Evaluation and Research (CDER), Center for Biologies Evaluation and Research (CBER), Jan. 2020, available from https://www.fda.gov/media/134605/download. 21 pages.
Akgul, "Mcl-1 is a potential therapeutic target in multiple types of cancer," *Cell. Mol. Life Sci.* 66:1326-1336, 2009.
Al-Mawali, "Leukemic Stem Cells Shows the Way for Novel Target of Acute Myeloid Leukemia Therapy," *J. Stem Cell Res. Ther.* 3(4):1-8, 2013.
Alvocidib, definition of alvocidib, NCI Dictionary of Cancer Terms, National Cancer Institute, retrieved from URL: https://www.cancer.gov/publications/dictionaries/cancer-terms/def/alvocidib, on Jan. 7, 2021, 1 page.
Araki et al., "Allogeneic Hematopoietic Cell Transplantation for Acute Myeloid Leukemia: Time to Move Toward a Minimal Residual Disease-Based Definition of Complete Remission?" *J Clin Oncol* 34(4):329-336, 2016.
Attal et al., "Lenalidomide Maintenance after Stem-Cell Transplantation for Multiple Myeloma," The New England Journal of Medicine 366:1782-1791, 2012.
Awan et al., "A Phase 1 Clinical Trial of Flavopiridol Consolidation in Chronic Lymphocytic Leukemia Patients Following Chemoimmunotherapy," *Ann. Hematol.* 95:1137-1143, 2016.
Beauchamp et al., "Amino Acid Ester Prodrugs of Acyclovir," *Antiviral Chemistry & Chemotherapy* 3(3): 157-164, 1992.
Belmar et al., "Small molecule Mcl-1 inhibitors for the treatment of cancer," *Pharmacol. Ther.* 145:76-84, 2015 (NIH Public Access Author Manuscript, available in PMC Jan. 1, 2016)(27 pages).
Benyon, "FDA Grants Venclexta an Accelerated Approval for AML Treatment," *Curetoday*:1-2, 2018.
Berge et al., "Pharmaceutical Salts," *Journal of Pharmaceutical Sciences* 66(1):1-19, 1977.
Billard, "BH3 Mimetics: Status of the Field and New Developments," *Mol. Cancer Ther.* 12(9):1691-1700, 2013.
Blum et al., "Phase I clinical and pharmacokinetic study of a novel schedule of flavopiridol in relapsed or refractory acute leukemias," *Haematologica* 95(7):1098-1105, 2010.
Boffo et al., "CDK9 Inhibitors in Acute Myeloid Leukemia," *Journal of Experimental & Clinical Cancer Research*, 37(36):1-10, 2018.
Bradbury et al., "Optimisation of a series of bivalent triazolopyridazine based bromodomain and extraterminal inhibitors: the discovery of (3R)-4-[2-[4-[1-(3-methoxy-[1,2,4]triazolo[4,3-b]pyridazin-6-yl)-4-piperidyl]phenoxy]ethyl]-1,3-dimethyl-piperazin-2-one (AZD5153)," Journal of Medicinal Chemistry 59(17):7801-7817, 2016. [journal accepted manuscript].
Brüsselbach et al., "Cell cycle-independent induction of apoptosis by the anti-tumor drug; Flavopiridol in endothelial cells," *Int. J. Cancer* 77(1):146-152, 1998.
Bundgaard, "Design of Prodrugs" Elsevier, Amsterdam: pp. 7-9 and 21-24, 1985. (7 pages).
Burrer et al., "Selective Peptide Inhibitors of Antiapoptotic Cellular and Viral Bcl-2 Proteins Lead to Cytochrome C Release During Latent Kaposi's Sarcoma-Associated Herpesvirus Infection," *Virus Res.* 211:86-88, 2016. (Author's manuscript).
Cannon, "Chapter Nineteen: Analog Design," Burger's Medicinal Chemistry and Drug Discovery, Fifth Edition, vol. 1: Principles and Practice, Wiley-Interscience, 1995, pp. 783-802, 784.
CAS Registry No. 951209-71-5, "IRX 2" Entered STN Oct. 23, 2007, 1 page.
CAS RN 1380087-89-7, Jun. 25, 2012, "4H-Isoxazolo[5,4-d][2]benzazepine-4-acetamide, 6-(4-chlorophenyl)-1-methyl-, (4S)-," 4 pages.
Chen et al., "Androgen Receptor Serine 81 Phosphorylation Mediates Chromatin Binding and Transcriptional Activation," Journal of Biological Chemistry 287(11):8571-8583, 2012.
Chen et al., "Lenalidomide in Multiple Myeloma—a Practice Guideline," *Curr. Oncol.* 20(2):e136-e149, 2013.

Chou et al., "Quantitative Analysis of Dose-Effect Relationships: The Combined Effects of Multiple Drugs or Enzyme Inhibitors," *Advances in Enzyme Regulation* 22:27-55, 1984.
Christian et al., "Flavopiridol in Chronic Lymphocytic Leukemia: A Concise Review," *Clinical Lymphoma & Myeloma* 9(Suppl 3):S179-S185, 2009.
Corbett et al., "Evaluation of Single Agents and Combinations of Chemotherapeutic Agents in Mouse Colon Carcinomas," Cancer 40:2660-2680, 1977.
Corbett et al., "Response of Transplantable Tumors of Mice to Anthracenedione Derivatives Alone and in Combination With Clinically Useful Agents," Cancer Treatment Reports 66:1187-1200, 1982.
Dang, "MYC on the Path to Cancer," *Cell* 149(1):22-35, 2012. (28 pages).
de Azevedo Jr. et al., "Structural basis for specificity and potency of a flavanoid inhibitor of human CDK2, a cell cycle kinase," *Proc. Natl. Acad. Sci. USA* 93:2735-2740, 1996.
de Haas et al., "Initial Diagnostic Work-Up of Acute Leukemia: ASCO Clinical Practice Guideline Endorsement of the College of American Pathologists and American Society of Hematology Guideline," *J Clin Oncol* 37(3):239-253, 2018.
Dehm et al., "Alternatively spliced androgen receptor variants," *Endocrine-Related Cancer* 18(5):R183-R196, 2011.
Dillman et al., "A comparative study of two different doses of cytarabine for acute myeloid leukemia: a phase III trial of Cancer and Leukemia Group B," Blood 78(10):2520-2526, 1991.
Dimopoulos et al., "Multiple Myeloma: EAH-ESMO Clinical Practice Guidelines for Diagnosis, Treatment and Follow-Up," *Annals of Oncology* 32(3):309-322, 2021.
DiNardo et al., "Venetoclax combined with decitabine or azacitidine in treatment-naive, elderly patients with acute myeloid leukemia," *Blood* 133(1):7-17, 2019.
Dittmann et al., "The Commonly Used PI3-Kinase Probe LY294002 Is an Inhibitor of BET Bromodomains," ACS Chem. Biol. 9(2):495-502, 2014.
Döhner et al., "Acute Myeloid Leukemia," *N. Engl. J. Med.* 373:1136-1152, 2015.
Döhner et al., "Diagnosis and Management of AML in Adults: 2017 ELN Recommendations From an International Expert Panel," *Blood* 129(4):424-447, 2017.
Eichhorst et al., "Chronic Lymphocytic Leukaemia: ESMO Clinical Practice Guidelines for diagnosis, treatment and follow up," *Annals of Oncology* 32(1):23-33, 2020.
Fenaux et al., "Myelodysplastic syndromes: ESMO Clinical Practice Guidelines for diagnosis, treatment and follow-up," *Annals of Oncology* 25(Supplement 3):iii57-iii69, 2014.
Ferrara et al., "Consensus-based definition of unfitness to intensive and nonintensive chemotherapy in acute myeloid leukemia: a project of SIE, SIES and GITMO group on a new tool for therapy decision making," *Leukemia* 27:997-999, 2013.
Ferriz et al., "Prodrug design of phenolic drugs," Current Pharmaceutical Design 16(18):2033-2052, 2010.
Freeman et al., "Measurable Residual Disease at Induction Redefines Partial Response in Acute Myeloid Leukemia and Stratifies Outcomes in Patients at Standard Risk Without NPM1 Mutations," *J Clin Oncol* 36(15):1486-1497, 2018. (24 pages).
Freeman et al., "Prognostic Relevance of Treatment Response Measured by Flow Cytometric Residual Disease Detection in Older Patients with Acute Myeloid Leukemia," *J Clin Oncol* 31(32):4123-4131, 2013.
Gambella et al., "Minimal Residual Disease by Flow Cytometry and Allelic-Specific Oligonucleotide Real-Time Quantitative Polymerase Chain Reaction in Patients With Myeloma Receiving Lenalidomide Maintenance: A Pooled Analysis," Cancer 125:750-760, 2019.
Gao et al., "Multiple Myeloma Cancer Stem Cells," *Oncotarget* 7(23):35466-35477, 2016.
George et al., "A Phase I, First-In-Human, Open-Label, Dose-Escalation, Safety, Pharmacokinetic, and Pharmacodynamic Study of Oral TP-1287 Administered Daily to Patients with Advanced Solid Tumors," *Journal of Clinical Oncology*, 38(15) Abstract 3611, 2020. (5 pages).

(56) References Cited

OTHER PUBLICATIONS

Gerber et al., "A clinically relevant population of leukemic CD34+ CD38− cells in acute myeloid leukemia," Blood 119(15):3671-3577, 2012.
Hamid et al., "Safety and Tumor Responses with Lambrolizumab (Anti-PD-1) in Melanoma," the New England Journal of Medicine 369(2):134-144, 2013.
Heuser et al., "Acute Myeloid Leukaemia in Adult Patients: ESMO Clinical Practice Guidelines for diagnosis, treatment and follow-up," Annals of Oncology 31(6):697-712, 2020.
Higuchi et al., "Pro-drugs as Novel Drug Delivery Systems," ACS Symposium Series: American Chemical Society, Washington, DC, vol. 14: 1-115, 1975. (118 pages).
Hillengass et al., "Minimal Residual Disease in Multiple Myeloma: Use of Magnetic Resonance Imaging," Seminars in Hematology 55(1):19-21, 2018. (Abstract Only).
Hoelzer et al., "Acute Lymphoblastic Leukaemia in adult patients: ESMO Clinical Practice Guidelines for diagnosis, treatment, and follow-up" Annals of Oncology 27(Supplement 5):v69-v82, 2016.
Hourigan et al., "Minimal residual disease in acute myeloid leukaemia," Nat. Rev. Clin. Oncol. 10(8):460-471, 2013.
Ivey et al., "Assessment of Minimal Residual Disease in Standard-Risk AML," The New England Journal of Medicine, 374(5):422-433, 2016.
Jongen-Lavrencic et al., "Molecular Minimal Residual Disease in Acute Myeloid Leukemia," The New England Journal of Medicine, 378(13):1189-1199, 2018.
Jornada et al., "The Prodrug Approach: A Successful Tool for Improving Drug Solubility," Molecules 21(42): 1-31, 2016.
Karp et al., "Phase 1 and pharmacokinetic study of bolus-infusion flavopiridol followed by cytosine arabinoside and mitoxantrone for acute leukemias," Blood 117(12):3302-3310, 2011.
Kelland, "Flavopiridol, The First Cyclin-Dependent Kinase Inhibitor to Enter the Clinic: Current Status," Expert Opinion on Investigational Drugs 9(12):2903-2911, 2000.
Kern et al., "Determination of Relapse Risk Based on Assessment of Minimal Residual Disease during Complete Remission by Multiparameter Flow Cytometry in Unselected Patients with Acute Myeloid Leukemia," Blood 104(10):3078-3085, 2004.
Kim et al., "Alvocidib Potentiates the Activity of Azacytidine in a MCL-1-Dependent Fashion" Blood 126:1343, 3 pages, 2015.
Kim et al., "Alvocidib Potentiates the Activity of Cytarabine and Mitoxantrone through the Targeting of MCL-1 When Administered in a Time Sequential Regimen in AML," Blood 126(23), 3799, 2015. (Abstract Only).
Klaeger et al., "The target landscape of clinical kinase drugs," Science 358:1148-1164, 2017.
Knutson et al., "Synergistic Anti-Tumor Activity of EZH2 Inhibitors and Glucocorticoid Receptor Agonists in Models of Germinal Center Non-Hodgkin Lymphomas," PLoS One 9(12):e111840, 2014.
Konopleva et al., "BCL-2 Inhibition in AML: An Unexpected Bonus?" Blood 132(10):1007-1012, 2018.
Kumar et al., "International Myeloma Working Group Consensus Criteria for Response and Minimal Residual Disease Assessment in Multiple Myeloma," Lancet Oncology 17:e328-e346, 2016.
Landgren et al., "MRD Testing in Multiple Myeloma: The Main Future Driver for Modem Tailored Treatment," Seminars in Hematology 55(1):44-50, 2018. (Abstract Only).
Landgren, "MRD Testing in Multiple Myeloma: From a Surrogate Marker of Clinical Outcomes to an Every-Day Clinical Tool," Seminars in Hematology 55(1):1-3, 2018. (Abstract Only).
Lin et al., "Phase II Study of Flavopiridol in Relapsed Chronic Lymphocytic Leukemia Demonstrating High Response Rates in Genetically High-Risk Disease," J. Clin. Oncol. 27(35):6012-6018, 2009.
Lindsley et al., "Acute myeloid leukemia ontogeny is defined by distinct somatic mutations," Blood 125(9):1367-1376, 2015.
Linenberger et al., "Biochemistry Students' Ideas About Shape and Charge in Enzyme-Substrate Interactions," Biochemistry and Molecular Biology Education 42(3):203-212, 2014.

Londono et al., "A reliable method for quantification of splice variants using RT-qPCR," BMC Mol. Biol. 17(8):1-12, 2016.
Malcovati et al., "Diagnosis and Treatment of Primary Myelodysplastic Syndromes in Adults: Recommendations From the European LeukemiaNet," Blood 122(17):2943-2964, 2013.
Malumbres, "Cyclin-dependent kinases," Genome Biol. 15(122):1-10, 2014.
Mayer, "Induction of apoptosis by flavopiridol unrelated to cell cycle arrest in germ cell tumour derived cell lines," Invest New Drugs 23(3):205-211, 2005.
Means et al., "Modifications to change properties," in Chemical Modification of Protein, Chapter 3, pp. 35-54, Holden-Day (1971).
Mian et al., "Spliceosome mutations exhibit specific associations with epigenetic modifiers and proto-oncogenes mutated in myelodysplastic syndrome," Haematologica 98(7):1058-1066, 2013.
Mikhael et al., "Treatment of Multiple Myeloma: ASCO and CCO Joint Clinical Practice Guideline," J Clin Oncol 37(14):1228-1264, 2019. (40 pages).
Mirguet, et al., "Discovery of Epigenetic Regulator I-BET762: Lead Optimization to Afford a Clinical Candidate Inhibitor of the BET Bromodomains," J. Med. Chem. 56(19):7501-7515, 2013.
Montesinos et al., "Tumor lysis syndrome in patients with acute myeloid leukemia: identification of risk factors and development of a predictive model," Haematologica 93(1):67-74, 2008.
Moros et al., "Synergistic antitumor activity of lenalidomide with the BET bromodomain inhibitor CPI203 in bortezomib-resistant mantle cell lymphoma," Leukemia 28(10):2049-2059, 2014.
NICE guidelines, "Myeloma: Diagnosis and Management," National Institute for Health and Care Excellence: 1-27, 2016.
Oken et al., "Toxicity and response criteria of the Eastern Cooperative Oncology Group," Am. J. Clin. Oncol. 5(6):649-655, 1982.
Opferman et al., "Obligate Role of Anti-Apoptotic MCL-1 in the Survival of Hematopoietic Stem Cells," Science 307:1101-1104, 2005.
Pandit-Taskar, "Functional Imaging Methods for Assessment of Minimal Residual Disease in Multiple Myeloma: Current Status and Novel ImmunoPET Based Methods," Seminars in Hematology, 55(1):22-32, 2018. (Abstract Only).
Papaemmanuil et al., "Genomic Classification and Prognosis in Acute Myeloid Leukemia," The New England Journal of Medicine 374(23):2209-2221, 2016.
Parovichnikova et al., "The MRD-Negativity Rate Measured By Flow Cytometry after the $1^{st}$ and the $2^{nd}$ Induction Course Among CR AML Patients from Different Cytogenetic Subgroups Does Not Differ Though the Morphological CR Achievement Does," Blood 132(Supplement 1): 1495, 2018.
Perrot et al., "Minimal Residual Disease Negativity Using Deep Sequencing is a Major Prognostic Factor in Multiple Myeloma," Blood 132(23):2456-2464, 2018.
Phelps et al., "Clinical response and pharmacokinetics from a phase 1 study of an active dosing schedule of flavopiridol in relapsed chronic lymphocytic leukemia," Blood 113(12):2637-2645, 2009.
Picaud et al., "RVX-208, an inhibitor of BET transcriptional regulators with selectivity for the second bromodomain," PNAS 110(49):19754-19759, 2013.
Pugh, "Circulating Tumour DNA for Detecting Minimal Residual Disease in Multiple Myeloma," Seminars in Hematology 55:38-40, 2018.
Quinn et al., "Targeting Mcl-1 for the therapy of cancer," Expert Opin Investig Drugs 20(10): 1397-1411, 2011. (24 pages).
Ramsey et al., "A Novel MCL1 Inhibitor Combined with Venetoclax Rescues Venetoclax-Resistant Acute Myelogenous Leukemia," Cancer Discov. 8(12):1566-1581, 2018.
Richard et al., "Hydroxyquinoline-derived compounds and analoguing of selective Mcl-1 inhibitors using afunctional biomarker," Bioorg Med Chem. 21(21):6642-9, 2013.
Rosenblatt et al., "PD-1 blockade by CT-011, anti PD-1 antibody, enhances ex-vivo T cell responses to autologous dendritic/myeloma fusion vaccine," J. Immunother. 34(5):409-418, 2011.
Roshal, "Minimal Residual Disease Detection by Flow Cytometry in Multiple Myeloma: Why and How?" Seminars in Hematology 55(1):4-12, 2018. (Abstract Only).

(56) References Cited

OTHER PUBLICATIONS

Salomon et al., "Recent developments in chemical deprotection of ester functional groups," Tetrahedron 49(18):3691-3748, 1993.
San Miguel et al., "Early Immunophenotypical Evaluation of Minimal Residual Disease in Acute Myeloid Leukemia Identifies Different Patient Risk Groups and May Contribute to Postinduction Treatment Stratification," Blood 98(6):1746-1751, 2001.
Schuurhuis et al., "Minimal/measureable residual disease in AML: a consensus document from the European LeukemiaNet MRP Working Party," Blood 131(12):1275-1291, 2018.
Soucek et al., "Modelling Myc inhibition as a cancer therapy," Nature 455(7213):679-683, 2008. (16 pages).
Szabo, "Understanding What Causes Relapse in Patients with Acute Myeloid Leukemia," Sep. 8, 2015, retrieved from https://www.pharmacytimes.com/news/understanding-what-causes-relapse-in-patients-with-acute-myeloid-leukemia, 3 pages.
Tanaka et al., "Design and Characterization of Bivalent BET Inhibitors," Nat. Chem. Biol. 12(12):1089-1096, 2016.
Terwijn et al., "High Prognostic Impact of Flow Cytometric Minimal Residual Disease Detection in Acute Myeloid Leukemia: Data From the HOVON/SAKK AML 42A Study," J Clin Oncol 31(31):3889-3897, 2013.
Thoren, "Mass Spectrometry Methods for Detecting Monoclonal Immunoglobulins in Multiple Myeloma Minimal Residual Disease," Seminars in Hematology 55(1):41-43, 2018. (Abstract Only).
Venkatesh et al., "MiniReview: Role of the development scientist in compound lead selection and optimization," Journal of Pharmaceutical Sciences 89(2):145-154, 2000.
Waldschmidt et al., "Comprehensive Characterization of Circulating and Bone Marrow-Derived Multiple Myeloma Cells at Minimal Residual Disease," Seminars in Hematology 55(1):33-37, 2018. (Abstract Only).
Wolff (ed.), Burger's Medicinal Chemistry and Drug Discovery, vol. 1: Principles and Practice, John Wiley & Sons, New York, 1997, pp. 975-977.
Xiang et al., "Mc11 haploinsufficiency protects mice from Myc-induced Acute Myeloid Leukemia," J Clin Invest., 120(6):2109-2118, 2010.
Yanagisawa et al., "Translating leukemia stem cells into the clinical setting: Harmonizing the heterogeneity," Experimental Hematology 44(12):1130-1137, 2016.
Yoshimoto et al., "FLT3-ITD up-regulates MCL-1 to promote survival of stem cells in acute myeloid leukemia via FLT3-ITD-specific STAT5 activation," Blood 114(24):5034-5043, 2009.
Zeidner et al., "Abstract PF243: Phase II Study Incorporating a Novel BH3-Profiling Biomarker Approach of Alvocidib Followed by Cytarabine and Mitoxantrone in Relapsed/Refractory Acute Myeloid Leukemia (AML)," Jun. 15, 2018, EHA Library, retrieved from https://library.ehaweb.org/eha/2018/stockholm/214729/joshua.f.zeidner.phase.ii.study.incorporating.a.novel.bh3-profiling.biomarker.html?f=topic=1574*media=3, 3 pages.
Zeidner et al., "Clinical activity of alvocidib (flavopiridol) in acute myeloid leukemia," Leuk. Res. 39(12):1312-1318, 2015.
Zeidner et al., "Final results of a randomized multicenter phase II study of alvocidib, cytarabine, and mitoxantrone versus cytarabine and daunorubicin (7+3) in newly diagnosed high-risk acute myeloid leukemia (AML)," Leuk. Res. 72:92-95, 2018.
Zeidner et al., "Phase I Study of Alvocidib Followed by 7+3 (Cytarabine + Daunorubicin) in Newly Diagnosed Acute Myeloid Leukemia," Clin Cancer Res 27(1):60-69, 2021.
Zeidner et al., "Zella 201: A Biomarker-Guided Phase II Study of Alvocidib Followed By Cytarabine and Mitoxantrone in MCL-1 Dependent Relapsed/Refractory Acute Myeloid Leukemia (AML)," Blood 132(Supplement 1):30, 2018, 6 pages.
Zhao et al., "BCL2 Amplicon Loss and Transcriptional Remodeling Drives ABT-199 Resistance in B Cell Lymphoma Models," Cancer Cell 35(5):752-766, 2019.
U.S. Appl. No. 16/814,398, filed Mar. 10, 2020.
U.S. Appl. No. 17/061,821, filed Oct. 2, 2020.
Byrd, J.C., et al., "Pretreatment Cytogenetic Abnormalities are Predictive of Induction Success, Cumulative Incidence of Relapse, and Overall Survival in Adult Patients with de novo Acute Myeloid Leukemia: Results from Cancer and Leukemia Group B (CALGB8461)", Blood, 100:4325-4336 (2002).
DiNardo, C.D. and Cortes, J.E., "New Treatment for Acute Myelogenous Leukemai", Expert Opin. Pharmacother, 16(1):95-106 (2015).
Evans, "Clathrate Compounds" in An Introduction to Crystal Chemistry, (London:Cambridge University Press), pp. 393-397 (1964).
Forostyan, T.V., et al.,"Abstract C081: Targeting CDK9 and MCL1 in Castration-Sensitive and Resistant Prostate Cancer Models", as present at AACR-NCI-EORTC International Conference on Moleular Targets and Cancer Therapeutiics, Oct. 26-30, 2019, Boston , MA, Molecular Cancer Therapeutic, 18(12):Supplement, 4 pages (2019).
George B, et al., "A Phase I, First-in-human, Open-label, Dose escalation, Safety, Pharmacokinetic, and Pharmacodynamic Study of Oral TP-1287 Administered Daily to Patients with Advanced Solid Tumors," American Society of Clinical Oncology—56th Annual Meeting; Poster; 2020.
Kaur, et al., "Growth Inhibition with Reversible Cell Cycle Arrest of Carcinome Cells by Falvone L86-8275,", JNCI, 22(84):1736-1740 (1992).
Kim, et al, "Abstract 3728: Targeting MCL-1 Expression Through the Inhibition of CDK9 and Super Enhancer Driven Transcription, Offers Multiple Opportunities for Rational Drug Combinations", Cancer Research, 76(14 Suppl.):3728 (2016).
Lee DJ et al., "Zella 101: Phase 1 Study of Alvocidib Followed by 7+3 Induction in Newly Diagnosed AML Patients," European Hematology Association—24th Congress; Abstract: PF285; 1 page; 2019.
Lee DJ, et al., "Zella-101: Phase 1 Study of Alvocidib Followed by 7+3 Induction in Newly Diagnosed AML Patients," European Hematology Association—24th Congress; Poster; Abstract PF285; 2019.
Lin, C.Y., et al., "Transcriptional Amplification in Turmor Cells with Elevated c-Myc", Cell, 151:56-67 (2012).
Litzow, M.R., et al., "A Randomized Trial of Three Novel Regimens for Recurrent Acute Myeloid Leukemia Demonstrates the Continuing Challenge of Treating this Difficult Disease", Am. J. of Hematol, 94(1):111-117 (2019).
Matsumura, Y., et al., "1959-CDK9 Inhibition Combined with Hypomethylating Agents Target MCL-1 Dependency in MDS and AML", AACR Annual Meeting 2021—Virtual-Poster to be presented during Session PO.MCB06.01-Cell Cycle on Apr. 10, 2021, downloaded from AACR website, URL: https://www.abstractsonline.com/pp8/#!/9325/presentation/3238 on Mar. 30, 2021, 2 pages.
Matsumura Y et al., Pharmacodynamic biomarker strategies for CDK9 inhibition . American Association for Cancer Research—112th Annual Meeting. 2020.
Matsumura Y, et al.. "Pharmacodynamic biomarker strategies for CDK9 inhibition," American Association for Cancer Research—111th Annual Meeting; Poster 2020.
Mintz G.S., "In-stent restenosis: the Washington Hospital Center experience", Am. J. Cardiol., 81:7E-13E (1998).
Mintz G.S., "Arterial remodeling after coronary angioplasty: a serial intravascular ultrasound study", Circulation,; 94:35-43 (1996).
Morita, Y., et al., "Phase 1 Study of Alvocidib (DSP-2033) in Combination with Cytarabine/Mitoxantrone (ACM) or Cytarabine/Daunorubicin (A=7+3) in Japanese Patients (pts) with Acute Myeloid Leukemia (AML)", Blood, 136(Supplement 1):4 pages (2020).
Morita, Y. et al., "Phase 1 Study of Alvocidib (DSP-2033) in Combination with Cytarabine/Mitoxantrone (ACM) or Cytarabine/Daunorubicin (A+7+3) in Japanese Patients (Pts) with Acute Myeloid Leukemia (AML)," American Society of Hematology—62nd Annual Meeting. 2020.
Motwani, M., et al., "Docetaxel and Navelbine Induced Apoptosis is Enhanced by Flavopiridol (Flavo) in Breast Cancer Cells and is Sequence Dependent", Proceedings of the Annual Meeting of The American Association for Cancer Research, New York, NY, 41:143 (2000).
NCCN Clinical Practice Guidelines in Oncology (NCCN Guidelines®) Acute Myeloid Leukemia, Version Feb. 2014, NCCN.org, 6 pages.

(56) References Cited

OTHER PUBLICATIONS

Quinsay, et al. "Bnip3 Mediates Permeabilization of Mitochondria and Release of Cytochrome c Via a Novel Mechanism," J Mol Cell Cardiol, 48(6):1146-1156 (2010).

Riabov, V., et al., "Preclinical Assessment of Alvocidib in Combination with 5-Azacytidine in High-Risk Myelodysplastic Syndromes", Blood, 138(Supplement 1):4649 (2021).

Schwartz, G.K., et al., "Phase I Trial of Sequential Paclitaxel and Cisplatin in Combination with the Cyclin Dependent Kinase Inhibitor Flavopiridol (Flavo) In Patients with Advanced Solid Tumors", Clinical Cancer Research, 5, p. 3754s, abstract #122 (1999).

Schwartz, G.K., et al., "Phase I Study of the Cyclin-Dependent Kinase Inhibitor flavopiridol in combination with Paclitaxel in Patients with Advanced Solid Tumors", Journal of Clinical Oncology, 20(8) (Apr. 15, 2002): pp. 2157-2170.

Sommakia, S., et al., "Alvocidib Synergizes with BRD4 Inhibitors to Improve Cytotoxity in an AML Cell Line" Poster P255 presented at AACR-NCI-EORTC Virtual International Conference on Molecular Targets and Cancer Therapeutics, Oct. 7-10, 2021.

Tibes, R. and Bogenberger, J.M., "Transcriptional Silencing of MCL-1 Through Cyclin-Dependent Kinase Inhibition in Acute Myeloid Leukemia", Frontiers in Oncoogy, 9:Article 1205, 13 pages (2019).

Use of a novel small molecule cyclin inhibitor flavopiridol in tumor therapy, Natl Med J China, vol. 85, No. 12, pp. 862-864, (Zhonghua Yi Xue Za Zhi, Mar. 30, 2005).

Yancey, D., et al., "BAD Dephosphorylation and Decreased Expression of MCL-1 Induce Rapid Apoptosis in Prostate Cancer Cells", PLOS One, 8(9):e74561, 11 pages (2013).

Zeidner JF, et al., "Phase II study incorporating a novel BH3-profiling biomarker approach of alvocidib followed by cytarabine and mitoxantrone in relapsed/refractory acute myeloid leukemia (AML)," European Hematology Association—2018 Meeting on Hematologic Malignancies. 2018.

Zeidner, J.F., et al., "Zella-101: Phase 1 Study of Alvocidib Followed by 7+3 Induction in Newly Diagnosed AML Patients," Poster as presented at European Hematology Association, 25th Congress held virtually Jun. 11-21, 2020, 1 page.

Zeidner, J.F., et al., "Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm", Blood, 136(Supplement 1):48-50 (2020).

Zeidner J et al., Zella 201: A Biomarker-Guided Phase II Study of Alvocidib Followed by Cytarabine and Mitoxantrone in MCL-1 Dependent Acute Myeloid Leukemia (AML): Results of Newly Diagnosed High-Risk Exploratory Arm, Abstract 1045, American Society of Hematology—62nd Annual Meeting. 2020.

Zeidner, J.F., et al., "A Prospective Biomarker Analysis of Alvocidib Followed by Cytarabine and Mitoxantrone in MCL-1-dependent Relapsed/Refractory Acute Myeloid Leukemia", Blood Cancer Journal, 11(175):5 pages (2021).

Lee, D., et al., "Abstract PF285: Zella 101:Phase I Study of Alvocidib Followed by 7+3 Induction in Newly Diagnosed AML Patients" as present during the 24th Annual Congress of the European Hematology Association 2019, HemaSphere, 3:S1: 94 (2019).

Matsumura, Y., et al., "Abstract 5813: Pharmacodynamic Biomarker Strategies for CDK9 Inhibition" as presented Annual Meeting of the American Association for Cancer Research 2020; Apr. 27-28 and Jun. 22-24, 2020 in Philadelphia, PA, Cancer Res., 80(Supplement 16):4 pages.

Matsumura Y et al., "CDK9 Inhibition Combined with Hypomethylating Agents Target MCL-1 Dependency in MDS and AML," American Association for Cancer Research—112th Annual Meeting, Poster, 2021.

Tefferi, A. and Vardiman, J.W., "Mechanics of Disease: Myelodysplastic Syndromes," The New England Journal of Medicine, vol. 361; 1872-1885 (2009).

Vogelzang, N.J., et al., "Phase I, first-in-human, dose-expansion study of oral TP-1287, a cyclin-dependent kinase 9 (CDK9) inhibitor, in patients with advanced solid tumors (ASTs)", Poster presented at the annual meeting of the American Association for Cancer Research, New Orleans, Louisiana, Apr. 8-13, 2022.

Wagner, A.J., et al., "Phase 1, first-in-human, dose-expansion study of oral TP-l287, a cyclin-dependent kinase 9 (CDK9) inhibitor, in patients with sarcoma", Poster presented at the American Association for Cancer Research (AACR): Special Conference on Sarcomas | May 9-12, 2022; Montreal, Quebec, Canada \* cited by examiner

TREATMENT REGIMEN FOR CANCERS THAT ARE INSENSITIVE TO BCL-2 INHIBITORS USING THE MCL-1 INHIBITOR ALVOCIDIB

This application is the U.S. National Stage of International Application No. PCT/US2018/050767, filed Sep. 12, 2018, which designates the U.S., published in English, and claims the benefit of U.S. Provisional Application No. 62/557,635, filed Sep. 12, 2017.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 910208_431USPC_SEQUENCE_LISTING.txt. The text file is 1.18KB, (B, was created on Mar. 11, 2020, and is being submitted electronically via EFS-Web.

BACKGROUND

Technical Field

The present invention relates, in general, to methods for treating BCL-2 inhibitor insensitive subjects using MCL-1 inhibitors and compositions related thereto.

Description of the Related Art

The B-cell lymphoma 2 (BCL-2) inhibitor Venetoclax (ABT-199, Venclexta) was approved by the FDA in 2016 for the treatment of chronic lymphocytic leukemia (CLL) for patients with chromosome 17p deletion and at least one prior treatment. Venetoclax functions by disrupting the interaction between the pro-survival BCL-2 protein and anti-survival, pro-apoptotic proteins such as BCL-2 interacting mediator of cell death (BIM) and BCL-2 associated death promoter (BAD). Venetoclax has demonstrated a high overall response rate in Phase I and Phase II clinical trials as a monotherapy in CLL (70-79%; Zhu, H., Almasan, A. *Drug Des Devel Ther* 2017, 11, 685-94).

Despite the success of Venetoclax in CLL, approximately 20-30% of patients show no response, a low number of patients demonstrate complete remission (8-20%), and nearly 50% of patients show disease progression after 18 months (Huber, H., et al. *Oncotargets and Therapy*, 2017, 10, 645-56).

Additional pro-survival proteins B-cell lymphoma-extra-large (BCL-xL) and myeloid cell leukemia 1 (MCL-1) also inhibit cell death by suppressing BIM and BAD, and represent possible resistance mechanisms to Venetoclax (Choudhary, G. S. et al. *Cell Death and Disease* January 2015, 6 (1), e1593 and Oppermann, S. et al., *Blood* 2016 128 (7) 934-47). The first generation BCL-2 inhibitor, navitoclax (ABT-263), that inhibits BCL-2 and BCL-xL, was toxic due to thrombocytopenia and demonstrated a key role of BCL-xL in platelet survival along with other reports (Zhang, H. et al. *Cell Death and Differentiation*, 2007 14, 943-51; Debrincat, M. A. et al., *Cell Death & Disease* 2015, 6, 1721).

Accordingly, a current therapeutic need exists to provide treatment for patients resistant to treatment using BCL-2 inhibitors and those who do not show a complete response and/or disease progression after treatment. The present invention fulfills these needs and offers other related advantages.

BRIEF SUMMARY

Embodiments of the present invention are generally directed to methods for treating cancer, for example, a BCL-2 inhibitor-resistant cancer. Some embodiments provide a method for treating a cancer in a subject in need thereof, the method comprising administering an effective amount of a treatment regimen comprising alvocidib or a prodrug thereof, or a pharmaceutically acceptable salt thereof, the cancer being BCL-2 inhibitor resistant, the subject being non-responsive or resistant to a prior treatment with a BCL-2 inhibitor, thereby treating the cancer in the subject.

One embodiment provides a method for treating a cancer in a subject in need thereof, the method comprising, determining that the cancer is BCL-2 inhibitor resistant and administering an effective amount of a treatment regimen comprising alvocidib or a prodrug thereof, or a pharmaceutically acceptable salt thereof, to the subject, thereby treating the cancer.

One other embodiment provides a method for treating a cancer in a subject in need thereof, the method comprising identifying the subject as likely to respond to treatment with alvocidib or a prodrug thereof, if the cancer is BCL-2 inhibitor resistant and the subject is non-responsive or resistant to a prior treatment with a BCL-2 inhibitor and administering a treatment regimen comprising an effective amount of alvocidib or a prodrug thereof, or a pharmaceutically acceptable salt thereof, to the subject.

Still another embodiment affords a method for treating a cancer in a subject in need thereof, the method comprising:
  administering a treatment regimen comprising alvocidib or a prodrug thereof, or a pharmaceutically acceptable salt thereof, to the subject, the cancer being BCL-2 inhibitor resistant as determined by an in vitro method comprising:
  obtaining a cancer cell from the subject; and
  i) quantifying expression of BCL-2 and MCL-1 in the cancer cell, wherein an increase in MCL-1 expression relative to BCL-2 expression indicates the subject has a BCL-2 inhibitor resistant cancer;
  ii) determining dependency on BCL-2 in the cancer cell, wherein a low BCL-2 dependency indicates the subject has a BCL-2 inhibitor resistant cancer; or
  iii) determining dependency on MCL-1 in the cancer cell, wherein a high MCL-1 dependency indicates the subject has a BCL-2 inhibitor resistant cancer.

Accordingly, these and other embodiments provide utility for treating cancer (e.g., leukemia) patients resistant and/or non-responsive to BCL-2 inhibitors. These and other aspects will be apparent upon reference to the following detailed description and attached figures.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
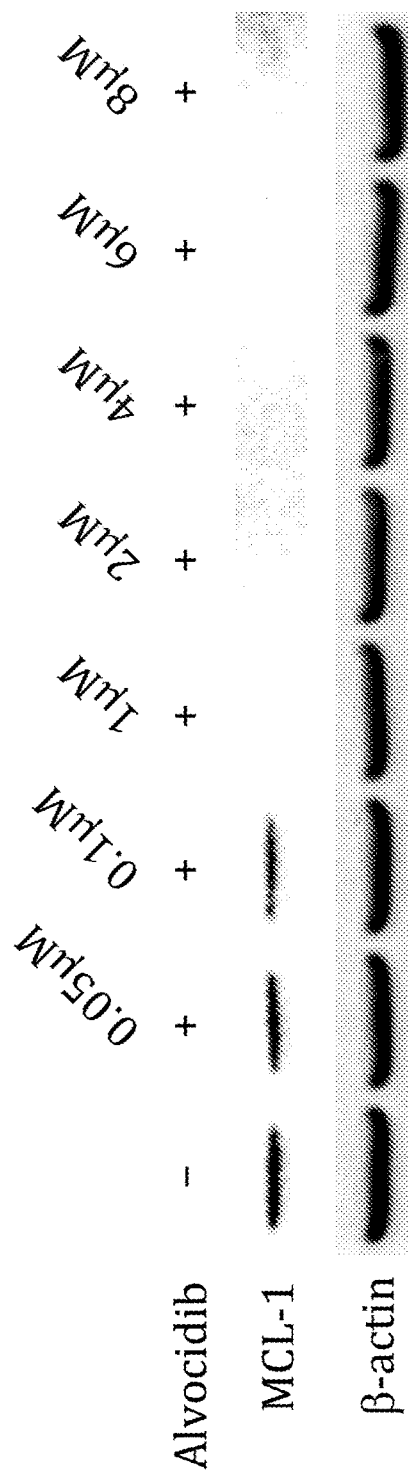
FIG. 1 shows a dose-dependent reduction in MCL-1 protein expression in MV-4-11 cells treated with alvocidib.

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless defined otherwise, all technical and scientific terms used herein have the same meaning as is commonly understood by one of skill in the art to which this invention belongs. As used in the specification and claims, the singular form "a", "an" and "the" include plural references unless the context clearly dictates otherwise.

Alvocidib (also known as Flavopiridol) refers to a compound having the following structure:

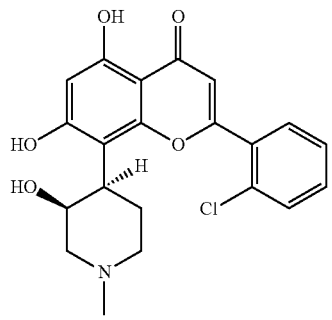 [SMILES: CN1CC[C@H](c2c(O)cc(O)c3c(=O)cc(-c4ccccc4Cl)oc23)[C@H](O)C1]

Pharmaceutically acceptable salts of alvocidib are included in within the definition of alvocidib in certain embodiments.

"Prodrug" is meant to indicate a compound that is converted under physiological conditions or by solvolysis to alvocidib. In some aspects, a prodrug is inactive when administered to a subject, but is converted in vivo to alvocidib, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. Prodrugs of alvocidib are typically prepared by modifying functional groups present in alvocidib in such a way that the modifications are cleaved in vivo to alvocidib. Exemplary prodrugs of alvocidib include compounds wherein a hydroxy group is masked with a functional group such that when the compound is administered to a mammalian subject, the functional group cleaves to form the free hydroxy compound (i.e., alvocidib). Specific examples of prodrugs include phosphate prodrugs of alvocidib as disclosed herein. Pharmaceutically acceptable salts of prodrugs are included within the scope of certain embodiments.

The term "effective amount" or "therapeutically effective amount" refers to that amount of a compound in a composition described herein that is sufficient to effect the intended application including but not limited to disease treatment, as defined below. The therapeutically effective amount may vary depending upon the intended treatment application (in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compound of the compositions chosen, the dosing regimen to be followed, whether it is administered in combination with other compounds, timing of administration, the tissue to which it is administered, and the physical delivery system in which it is carried.

As used herein, "treatment" or "treating" refers to an approach for obtaining beneficial or desired results with respect to a disease, disorder or medical condition including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "co-administration," "administered in combination with," and their grammatical equivalents, as used herein, encompass administration of two or more agents to an animal, including humans, so that both agents and/or their metabolites are present in the subject at the same time. Co-administration includes simultaneous administration in separate compositions, administration at different times in separate compositions, or administration in a composition in which both agents are present.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

In some embodiments, pharmaceutically acceptable salts include quaternary ammonium salts such as quaternary amine alkyl halide salts (e.g., methyl bromide).

The terms "antagonist" and "inhibitor" are used interchangeably, and they refer to a compound having the ability to inhibit a biological function of a target protein, whether by inhibiting the activity or expression of the protein, such as MCL-1. Accordingly, the terms "antagonist" and "inhibitors" are defined in the context of the biological role of the target protein. A preferred biological activity inhibited by an antagonist is associated with the development, growth, or spread of a tumor.

The term "agonist" as used herein refers to a compound having the ability to initiate or enhance a biological function of a target protein, whether by inhibiting the activity or expression of the target protein. Accordingly, the term "agonist" is defined in the context of the biological role of the target polypeptide. While preferred agonists herein specifically interact with (e.g., bind to) the target, compounds that initiate or enhance a biological activity of the target polypeptide by interacting with other members of the signal transduction pathway of which the target polypeptide is a member are also specifically included within this definition.

As used herein, "agent" or "biologically active agent" refers to a biological, pharmaceutical, or chemical compound or other moiety. Non-limiting examples include a simple or complex organic or inorganic molecule, a peptide, a protein, an oligonucleotide, an antibody, an antibody derivative, antibody fragment, a vitamin derivative, a carbohydrate, a toxin, or a chemotherapeutic compound. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "selective inhibition" or "selectively inhibit" refers to a biologically active agent refers to the agent's ability to preferentially reduce the target signaling activity as compared to off-target signaling activity, via direct or indirect interaction with the target.

"Subject" refers to an animal, such as a mammal, for example a human. The methods described herein can be useful in both human therapeutics and veterinary applications. In some embodiments, the subject is a mammal, and in some embodiments, the subject is human.

"Mammal" includes humans and both domestic animals such as laboratory animals and household pets (e.g., cats, dogs, swine, cattle, sheep, goats, horses, rabbits), and non-domestic animals such as wildlife and the like.

"Radiation therapy" means exposing a subject, using routine methods and compositions known to the practitioner, to radiation emitters such as alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

The term "in vivo" refers to an event that takes place in a subject's body.

A "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefor.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Methods for Treatment

The current approved therapeutic regimen for treating patients with CLL with chromosome 17p deletion (i.e., Venetoclax/ABT-199) shows a favorable overall response and initial disease free progression; however only a small subset of patients show a complete response and at least 50% of patients show disease progression after 18 months. Thus, the present disclosure is based, at least in part, on the fact that CDK9/MCL-1 inhibitors provide a useful treatment option for cancer patients (e.g., with CLL) that show resistance to BCL-2 inhibitors.

Accordingly, embodiments of the present invention are useful to treat leukemia patients resistant and/or non-responsive to BCL-2 inhibitors. In addition, certain embodiments may be used with or without a companion diagnostic assay, such as a BH3 profiling assay, that determines if patients will respond to CDK9/MCL-1 inhibitors.

One embodiment provides a method for treating a BCL-2 inhibitor-resistant cancer in a subject in need thereof, the method comprising administering an effective amount of a treatment regimen comprising alvocidib or a prodrug thereof, or a pharmaceutically acceptable salt thereof, to a subject being non-responsive or resistant to a prior treatment with a BCL-2 inhibitor, thereby treating the cancer in the subject.

In embodiments, the treatment regimen comprises a prodrug of alvocidib, such as those described in US2016/0340376, which is incorporated by reference herein in its entirety. In embodiments, the prodrug of alvocidib is a phosphate prodrug of alvocidib. In some embodiments the phosphate prodrug of alvocidib has the following structure (I):

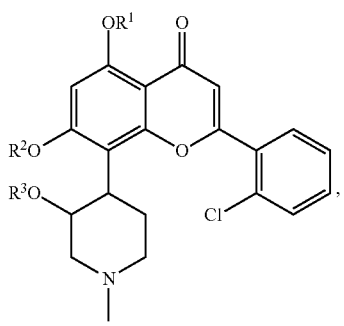

or a stereoisomer, tautomer or pharmaceutically acceptable salt thereof, wherein:
one of $R^1$, $R^2$ and $R^3$ is —P(=O)(OH)$_2$, and the other two of $R^1$, $R^2$ and $R^3$ are each H.

In certain embodiments, the phosphate prodrug of alvocidib has the following structure:

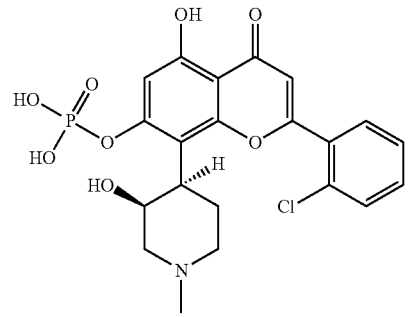 [SMILES: CN1CC[C@H](c2c(OP(=O)(O)O)cc(O)c3c(=O)cc(-c4ccccc4Cl)oc23)[C@H](O)C1]

Another embodiment provides a method for treating a cancer in a subject in need thereof, the method comprising, determining that the cancer is BCL-2 inhibitor resistant and administering an effective amount of a treatment regimen comprising alvocidib or a prodrug thereof, or a pharmaceutically acceptable salt thereof, to the subject, thereby treating the cancer. In specific embodiments, the cancer is resistant to a prior treatment with a BCL-2 inhibitor.

A related embodiment provides a method for treating a cancer in a subject in need thereof, the method comprising identifying the subject as likely to respond to treatment with alvocidib or a prodrug thereof if the cancer is BCL-2 inhibitor resistant and the subject is non-responsive or resistant to a prior treatment with a BCL-2 inhibitor and administering a treatment regimen comprising an effective amount of alvocidib or a prodrug thereof, or a pharmaceutically acceptable salt thereof, to the subject.

One embodiment affords a method for treating a cancer in a subject in need thereof, the method comprising, administering a treatment regimen comprising alvocidib or a prodrug thereof, or a pharmaceutically acceptable salt thereof, to the subject, the cancer being BCL-2 inhibitor resistant as determined by an in vitro method comprising
  obtaining a cancer cell from the subject; and
  i) quantifying expression of BCL-2 and MCL-1 in the cancer cell, wherein an increase in MCL-1 expression relative to BCL-2 expression indicates the subject has a BCL-2 inhibitor resistant cancer;
  ii) determining dependency on BCL-2 in the cancer cell, wherein a low BCL-2 dependency indicates the subject has a BCL-2 inhibitor resistant cancer; or
  iii) determining dependency on MCL-1 in the cancer cell, wherein a high MCL-1 dependency indicates the subject has a BCL-2 inhibitor resistant cancer.

In certain embodiments, the subject has received a prior treatment with a BCL-2 inhibitor, such as Venetoclax.

MCL-1 and BCL-2 dependency can be determined based on methods known in the art, such as BH3 profiling as described in U.S. Pat. Nos. 7,868,133; 8,221,966; and 8,168,755 and US Patent Publication Nos. 2011/0130309, 2016/0303101, and 2018/0172673, the contents of all of which are hereby incorporated by reference in their entireties.

In some embodiments, MCL-1 dependency is determined by contacting a subject's cancer cell with any one or more of the profiling peptides, such as those described in US Patent Publication No. 2018/0172673, which is incorporated by reference in its entirety. In some embodiments, the profiling peptide comprises the sequence of YGRKKRRQRRRGGGRPEIWMTQGLRRLGDEINAY-YAR (SEQ ID NO:1) or RPEIWMTQGLRRLGDEINAY-YARGGGYGRKKRRQRRR (SEQ ID NO:2). In some embodiments, the profiling peptide consists of the sequence of SEQ ID NO:1 or SEQ ID NO:2. In other embodiments, the profiling peptide is at least a portion of NOXA.

Such peptides may be used to produce a sensitivity profile for a cancer cell or a plurality of cancer cells. In some embodiments, the cancer cell or plurality of cancer cells is isolated from a tumor. In certain embodiments, the cancer cell or plurality of cancer cells is derived from the biopsy of a non-solid tumor. In embodiments, the cancer cell or plurality of cancer cells is obtained from peripheral blood from the subject. In other embodiments the cancer cell or plurality of cancer cells is obtained from bone marrow of the subject.

In embodiments, the cancer cells are from a solid cancer. In some embodiments, the cancer cell or plurality of cancer cells is derived from a solid tumor. In some embodiments, the cancer cell or plurality of cancer cells is a circulating tumor cell. In embodiments, the cancer cells are from a non-solid cancer. In various embodiments, the cancer cells are from a pre-metastatic cancer. In various embodiments, the cancer cells are from a metastatic cancer.

In a specific embodiment, the cancer cell or plurality of cancer cells is a multiple myeloma cell that is enriched by selection from a biopsy sample with an anti-CD138 antibody bound to a solid matrix or bead. In a specific embodiment, the cancer cell or plurality of cancer cells is an AML cell that is enriched by binding to a CD45-directed antibody. In a specific embodiment, the cancer cell or plurality of cancer cells is from a chronic lymphogenous leukemia or diffuse large B-cell lymphoma that is enriched by non-B cell depletion.

In various embodiments, the plurality of cancer cells is from a sample that has been frozen. In such embodiments, the sample may be warmed using a quick thaw process. The sample may then be added to culture medium and incubated.

In other embodiments, the plurality of cancer cells is from a sample that has not been frozen, i.e., that has been freshly collected. In such embodiments, the sample is added to culture medium and incubated after being isolated.

In embodiments, the cancer cell, the plurality of cancer cells, or a portion thereof, is contacted with one or more profiling peptides disclosed herein and a percent polarization is determined. In embodiments, the cancer cell, the plurality of cancer cells, or a portion thereof, is contacted with one or more profiling peptides disclosed herein and a change in mitochondrial integrity of the cell(s) is detected. In various embodiments, more than one profiling peptide may be used at once. In such embodiments, a panel of profiling peptides (e.g., 2, 3, 4, 5, 10, etc. profiling peptides) may be screened on a single subject specimen.

In some embodiments, the cancer cell, the plurality of cancer cells, or a portion thereof, is contacted with a composition comprising a profiling peptide. In such embodiments, the composition may comprise a profiling peptide in a concentration ranging from about 1.5 µM to about 2.5 µM. In embodiments, the composition comprises a profiling peptide in a concentration ranging from about 1.75 µM to about 2.25 µM. In embodiments, the composition comprises a profiling peptide in a concentration of about 2.0 µM.

In embodiments, the plurality of cancer cells, or a portion thereof, is contacted with one or more profiling peptides for about 15 minutes to about 45 minutes. In some embodiments, the plurality of cancer cells, or a portion thereof, is contacted with one or more profiling peptides for about 20 minutes to about 40 minutes. In some embodiments, the plurality of cancer cells, or a portion thereof, is contacted with one or more profiling peptides for about 30 minutes.

A percent polarization can be related to a change in mitochondrial integrity in the cell or plurality of cells. A change in mitochondrial integrity can be detected in any suitable manner, such as, for example, a change in mitochondrial membrane potential, chromatin condensation, loss of viability, Cytochrome C translocation from the mitochondrial intermembrane space to the cytosol, swelling of the mitochondria, mitochondrial fission, morphological changes (e.g., cell shrinkage, membrane blebbing, etc.), phosphatidyl serine externalization (e.g., as measured by annexin V staining) or the increase in reactive oxygen intermediates. As is understood by one of skill in the art, various methods of detection for each of the indications of a change in mitochondrial integrity may be employed.

In embodiments, the change in mitochondrial integrity will be a decrease in mitochondrial integrity. In some embodiments, the decrease in mitochondrial integrity is measured by a decrease in mitochondrial membrane potential. The decrease in mitochondrial potential may be determined using any suitable method known in the art. In some embodiments, the decrease in mitochondrial integrity is measured by Cytochrome C leakage. In some embodiments, the decrease will be a statistically significant, clinically significant, or biologically significant decrease. In some embodiments, the decrease is a 2%, 5%, 10%, 15%, 20%, 25%, 30%, 35%, 40%, 45%, 50%, 60%, 70%, 80%, or 90% difference in a measurement of mitochondrial integrity, as described herein, as compared to a control.

A change in mitochondrial membrane potential may be measured using any suitable detecting agent. The detecting agent can be any suitable agent, such as a fluorescent dye, a non-fluorescent dye that can be converted to a fluorescent dye, an antibody, and the like. Fluorescent dyes include, for example, 5,5',6,6'-Tetrachloro-1,1',3,3'-tetraethyl-imidacarbocyanine iodide (JC-1), propidium iodide (PI), 1,1',3,3,3', 3'-hexamethylindodicarbo-cyanine iodide (DilC1), and 3,3'-Dihexyloxacarbocyanine Iodide ($DiOC_6$). In various embodiments, the fluorescent dye is a potentiometric dye. Suitable potentiometric dyes include, for example, DilC1, JC-1, and rhodamine 123. In embodiments, the potentiometric dye included is JC-1 or rhodamine 123. In other embodiments, the dye is dihydrorhodamine 123, a non-fluorescent dye that can be converted via oxidation to rhodamine 123, a fluorescent dye.

In embodiments, the plurality of cancer cells, or a portion thereof, is contacted with a dye in a concentration ranging from about 0.5 nM to about 1.5 nM. In embodiments, the plurality of cancer cells, or a portion thereof, is contacted with a dye in a concentration ranging from about 0.75 nM to about 1.25 nM. In embodiments, the plurality of cancer cells, or a portion thereof, is contacted with a dye in a concentration of about 1.0 µM. In embodiments, the plurality of cancer cells, or a portion thereof, is contacted with a dye for about 60 minutes to about 120 minutes. In embodiments, the plurality of cancer cells, or a portion thereof, is contacted with a dye for about 75 minutes to about 105 minutes. In embodiments, the plurality of cancer cells, or a portion thereof, is contacted with a dye for about 80 minutes to about 100 minutes. In embodiments, the plurality of cancer cells, or a portion thereof, is contacted with a dye for about 90 minutes.

In another example, Cytochrome C translocation can be measured using immunofluorescence staining. In a further example, an increase in reactive oxygen intermediates can be measured using flow cytometric analysis after staining with carboxy-dichlorofluorescin diacetate.

In various embodiments, the plurality of cancer cells is divided into two or more portions (e.g., three portions) for the purposes of profiling. In embodiments, one portion is treated with a negative control and one portion is contacted with one or more profiling peptides or a composition comprising one or more profiling peptides disclosed herein. Any suitable negative control may be used. Examples of negative controls include water and water soluble organic solvents, such as DMSO, ethanol, and methanol. In some embodiments, the negative control is water.

Accordingly, methods of the present disclosure comprise contacting a first portion of a plurality of cancer cells with a profiling peptide; contacting a second portion of the plurality of cancer cells with a negative control; and determining a percent polarization of the first portion and the second portion of the plurality of cancer cells.

In some embodiments, one portion of the plurality of cancer cells is contacted with a positive control. In embodiments, one portion is treated with a negative control, one portion is contacted with a positive control, and one portion is contacted with one or more profiling peptides or a composition comprising one or more profiling peptides disclosed herein. In such embodiments, methods of the disclosure further comprise contacting a third portion of the plurality of cancer cells with a positive control. Any suitable positive control may be used. Examples of positive controls include Carbonyl cyanide-4-(trifluoromethoxy)phenylhydrazone (FCCP), Carbonyl cyanide m-chlorophenyl hydrazone (CCCP), N5,N6-bis(2-fluorophenyl)-[1,2,5]oxadiazolo[3,4-b]pyrazine-5,6-diamine (BAM-15), and the like. In particular embodiments, the positive control used is CCCP.

In embodiments, the plurality of cancer cells, or a portion thereof, is contacted with a positive control in a concentration ranging from about 25 μM to about 250 μM. In embodiments, the plurality of cancer cells, or a portion thereof, is contacted with a positive control in a concentration ranging from about 25 μM to about 200 μM.

In embodiments, the plurality of cancer cells, or a portion thereof, is contacted with a positive control in a concentration ranging from about 50 μM to about 150 μM. In embodiments, the plurality of cancer cells, or a portion thereof, is contacted with a positive control in a concentration of about 100 M.

In embodiments, at least a portion of the plurality of cancer cells is contacted with a blocking buffer that blocks receptors on the cells that bind to the Fragment crystallizable (FC) region of antibodies (i.e., FC receptors). In embodiments, the plurality of cancer cells is contacted with the blocking buffer before being separated into portions. In embodiments, the blocking buffer is incubated with the plurality of cancer cells at room temperature.

In some embodiments, a plurality of cancer cells is contacted with one or more labels. In embodiments, the plurality of cancer cells is contacted with a label before being separated into portions. In some embodiments that use flow cytometry, the labels are fluorophores attached to antibodies or a chemical entity with affinity for a cell membrane feature or other cellular structure. In other embodiments that use flow cytometry, the labels are quantum dots attached to antibodies or a chemical entity with affinity for a cell membrane feature or other cellular structure. In any of these embodiments, the antibodies or chemical entities may recognize any suitable cell surface marker, such as CD3, CD13, CD20, CD33, CD34, or CD45. In various embodiments, a combination of labels is used.

In embodiments, the label comprises at least one monoclonal antibody. In some embodiments, the at least one monoclonal antibody comprises an anti-CD45 antibody, an anti-CD3 antibody, an anti-CD20 antibody, an anti-CD13 antibody, an anti-CD33 antibody, an anti-CD34 antibody, an anti-CD117 antibody, anti-HLA-DR antibody, or a combination thereof. In specific embodiments, the at least one monoclonal antibody comprises an anti-CD45 antibody, an anti-CD3 antibody, an anti-CD20 antibody, an anti-CD13 antibody, an anti-CD33 antibody, an anti-CD34 antibody, or a combination thereof.

In some embodiments, an additive with a high affinity for calcium channels is added to the plurality of cancer cells, or a portion thereof. In some such embodiments, the additive is a diterpenoid. In particular embodiments, the additive is ryanodine. In embodiments, the additive is added in a concentration that is sufficient to significantly reduce or prevent nonspecific dye uptake. In some embodiments, the additive is added in a concentration of at least about 20 μM. In some embodiments, the additive is added in a concentration of at least about 30 μM. In embodiments, the diterpenoid is added in a concentration ranging from about 10 μM to about 50 μM. In embodiments, the diterpenoid is added in a concentration ranging from about 20 μM to about 40 μM. In embodiments, the diterpenoid is added in a concentration of about 30 μM.

In some embodiments, an ATP synthase inhibitor is added to the plurality of cancer cells, or a portion thereof. In some such embodiments, the ATP synthase inhibitor is an Oligomycin. In particular embodiments, the Oligomycin is Oligomycin A. In some embodiments, the ATP synthase inhibitor is added in a concentration of at least 0.25 um. In some embodiments, the ATP synthase inhibitor is added in a concentration of at least about 0.5 um. In some embodiments, the ATP synthase inhibitor is added in a concentration of no more than about 1.0 um. In embodiments, the ATP synthase inhibitor is added in a concentration ranging from about 0.25 μM to about 0.75 μM. In embodiments, the ATP synthase inhibitor is added in a concentration ranging from about 0.4 μM to about 0.6 μM. In embodiments, the ATP synthase inhibitor is added in a concentration of about 0.5 μM.

In embodiments, the plurality of cancer cells is then contacted with a detecting agent, as described above. In some embodiments, the detecting agent is a dye.

In some embodiments, the detecting agent is a fluorescent dye. In some embodiments, the detecting agent is a potentiometric dye. In certain embodiments, the dye is JC-1, $DiOC_6$, or rhodamine 123. In certain embodiments, the dye is JC-1 or rhodamine 123. In particular embodiments, the dye is $DiOC_6$.

In some embodiments, the plurality of cancer cells, or a portion thereof, is washed prior to being contacted with the detecting agent.

In such embodiments, the plurality of cancer cells may then be analyzed using flow cytometry. In embodiments, determining the percent polarization of the first portion and the second portion of the plurality of cancer cells comprises analyzing the first portion and the second portion of the plurality of cancer cells by flow cytometry. In some embodiments, the third portion of the plurality of cancer cells is also analyzed by flow cytometry.

Any suitable gating may be used in flow cytometry analysis. In embodiments, analyzing the first portion, second portion, and third portion of the plurality of cancer cells by flow cytometry comprises gating on the positive control. In some embodiments, such gating is on the CD45 dim, CD13, CD33, and CD34 high population of blast cells. In other embodiments, such gating is the CD34 dim, CD3 and CD20 high population.

Methods of the disclosure include isolating a plurality of cancer cells from a subject sample; the cells are then labeled; treated with a negative control, a positive control, or a profiling peptide of the disclosure; contacted with a dye; and analyzed with flow cytometry.

Some methods described herein further comprise determining an Mcl-1 dependency percentage for the first portion of the plurality of cancer cells based at least on the percent polarization of the first portion and the second portion of the plurality of cancer cells.

In embodiments, polarized and depolarized cells are counted. The percent polarization can then be calculated by dividing the number of polarized cells by the total number of cells and multiplying by 100. In such embodiments, blasts are gated as described above. The blast gate in then plotted on a histogram for detection agent signal. A gate is then created specifically on the polarized cells, and the percent of cells which respond to treatment with a profiling peptide can be found with the following equation:

$$\text{Percent Priming} = \left(\frac{NC - PP}{NC}\right) \times 100 \tag{1}$$

NC is the average percent polarization of the second portion of the plurality of cancer cells and PP is the percent polarization of the first portion of the plurality of cancer cells.

In embodiments, the Mcl-1 dependency percentage (MDP) is defined by the following equation:

$$MDP = C \times \text{Avg}[\text{Percent Priming}] \tag{2}$$

where C is a calibration factor and Avg[Percent Priming] is the average of the percent priming for one or more replicates.

In embodiments, the calibration factor ranges from about 0.1 to about 3.0. In some embodiments, the calibration factor ranges from about 0.5 to about 2.5. In some embodiments, the calibration factor ranges from about 1.0 to about 2.0. In some embodiments, the calibration factor ranges from about 1.4 to about 1.8. In some embodiments, the calibration factor is about 1.5.

Unless otherwise noted, the Mcl-1 dependency percentages calculated herein correspond to a profiling peptide concentration of 1 μM with CCCP as the positive control and water or DMSO as the negative control. In some embodiments, the time occurs over a window from between about 0 to about 300 min to about 0 to about 30 min.

In an illustrative method of the disclosure, a plurality of cancer cells prepared, and sample quality is confirmed. In the case of a frozen sample, samples are quickly thawed, for example, placing them in a 37° C. water bath for about 60-70 seconds. After thawing the sample, the cells are transferred to a flask containing warm culture medium. After incubation, the quality (e.g., viability, cell count, etc.) is confirmed. In the case of a fresh sample, mononuclear cells are isolated from bone marrow aspirates following standard laboratory protocol (e.g., Ficoll-Paque separation). The cells are counted and the viability of the isolated cells is determined. The cells are then transferred to a flask containing warm culture medium. The cells are then pelleted and resuspended in a buffer that blocks FC receptors. A mix of monoclonal antibodies is then added and incubated. After incubating with the label, the cells are again pelleted. The cells are again resuspended in a mix of an assay buffer that has a pH ranging from about 7.4 to about 7.6, a diterpenoid (e.g., ryanodine), and an ATP synthase inhibitor (e.g. Oligomycin A). The suspended cells are then aliquoted into three portions. The first portion is mixed with a negative control (e.g., nuclease free water), the second portion is mixed with a positive control (e.g., CCCP), and the third portion is mixed with the profiling peptide (e.g., having the sequence of SEQ ID NO:1). The three portions are then incubated. After the incubation, the cells are pelleted and resuspended in the assay buffer. A dye (e.g., $DiOC_6$) is then added to each portion of cells.

In the illustrative method, the cells are analyzed via flow cytometry. The control cell lines are analyzed using the live gate. The sample is analyzed by gating single, live cells by plotting forward vs. side scatter. Outliers containing high forward and side scatter values may be assumed to be doublets and dying cells, respectively, and may be excluded from the final analysis. Events that are very low in both forward and side scatter may also be excluded as cellular debris. Generate a dot plot of channel FL5 (PC7 labeled anti-CD45 antibody) against side scatter and identify the CD45 dim population. Using only the events within the "CD45 dim" gate, generate a dot plot of channel FL4 (PC5 labeled anti-CD13, anti-CD33 and anti-CD34 antibodies) against channel FL3 (ECD/PE-Texas Red labeled anti-CD3 and anti-CD20 antibodies). In order to gate exclusively on AML blasts, gate cells that are high in channel FL4 and low in channel FL3 (live cell population). Using only events within the "Blasts" population, generate a histogram of FL1. Determine the cells high in channel FL1. Apply the gates created to all aliquots of all treatments of the same sample.

Some methods described herein further comprise determining an MCL-1 dependency percentage for the first portion of the plurality of cancer cells based at least on the change in mitochondrial integrity.

In embodiments, the MDP is defined by the following equation:

$$MDP = \left[1 - \left(\frac{Pep - PC}{NC - PC}\right)\right] * 100 \tag{3}$$

Where PC is the AUC of the positive control, NC is the AUC of the negative control, and Pep is the AUC of the profiling peptide. Unless otherwise noted, the MCL-1 dependency percentage calculated using this equation correspond to a profiling peptide concentration of 1 μM with CCCP as the positive control and water or DMSO as the negative control. The AUC is either area under the curve or signal intensity. In embodiments, the AUC is the median fluorescent intensity (MFI). In some embodiments, the area under the curve is established by homogenous time-resolved fluorescence (HTRF). In some embodiments, the time occurs over a window from between about 0 to about 300 min to about 0 to about 30 min. In some embodiments, the area under the curve is established by fluorescence activated cell sorting (FACS) or microplate assay as known in the art or described herein. In some embodiments, the signal intensity is a single time point measurement that occurs between about 5 min and about 300 min.

In embodiments where more than one profiling peptide is used, the MCL-1 dependency percentage (PP) is defined by the following equation:

$$PP = \left[100 * \left(\frac{NC\,AUC - Pep_1 AUC}{NC\,AUC - PC_{avg} AUC}\right)\right] Pep_1 +$$
$$\left[100 * \left(\frac{NC\,AUC - Pep_2 AUC}{NC\,AUC - PC_{avg} AUC}\right)\right] Pep_2 + \ldots$$
$$\left[100 * \left(\frac{NC\,AUC - Pep_n AUC}{NC\,AUC - PC_{avg} AUC}\right)\right] Pep_n$$

In an illustrative method of the disclosure, a plurality of cancer cells are isolated from a subject sample, and sample quality is confirmed. The cells are then pelleted, blocked in BSA, and labeled. After staining, cells are pelleted and separated into three portions and treated with either water or dimethyl sulfoxide (DMSO) (negative control), CCCP (positive control) or a profiling peptide of the disclosure (subject dependency). DiOC$_6$, a cationic mitochondrial dye is added. Later, the cells are analyzed via flow cytometry.

In some embodiments, a plurality of cancer cells are isolated from primary bone marrow aspirates and sample quality is determined. Cells are then pelleted, blocked in BSA and labeled for markers specific to B and T cells, as well as monocyte differentiation markers and blast-specific markers. After staining, cells are pelleted and separated into three portions and treated with either water (negative control), CCCP (positive control) or SEQ ID NO:1 (subject dependency). DiOC$_6$, a cationic mitochondrial dye is added. The cells are analyzed via flow cytometry. Blast cells are isolated by gating on the CD45 dim, CD13, CD33, and CD34 high population of each sample.

In particular embodiments, a plurality of cancer cells are isolated from primary bone marrow aspirates using density-gradient centrifugation. Sample quality is determined using trypan blue exclusion. Cells are then pelleted, blocked in BSA and labeled for markers specific to B and T cells, as well as monocyte differentiation markers and blast-specific markers. After staining, cells are pelleted and separated into fluorescent-activated cell sorting (FACS) tubes and treated with either water (negative control), CCCP (positive control) or SEQ ID NO:1 (subject dependency). DiOC$_6$, a cationic mitochondrial dye is added. The cells are then analyzed via flow cytometry. Blast cells are isolated by gating on the CD45 dim, CD13, CD33 and CD34 high population of each sample.

In any of the above embodiments, the cancer cell, the plurality of cancer cells, or a portion thereof, is not permeabilized, for example with a cell permeabilization agent such as digitonin.

In embodiments, the subject has a MCL-1 dependency percentage of at least 5%. In embodiments, the subject has a MCL-1 dependency percentage of at least 10%. In embodiments, the subject has a MCL-1 dependency percentage of at least 20%. In embodiments, the subject has a MCL-1 dependency percentage of at least 30%. In embodiments, the subject has a MCL-1 dependency percentage of at least 40%. In embodiments, the subject has a MCL-1 dependency percentage of at least 50%. In embodiments, the subject has a MCL-1 dependency percentage of at least 60%. In embodiments, the subject has a MCL-1 dependency percentage of at least 70%. In some embodiments, the subject has a MCL-1 dependency percentage of no more than 70%. In some embodiments, the subject has a MCL-1 dependency percentage of no more than 60%. In some embodiments, the subject has a MCL-1 dependency percentage of no more than 50%. In some embodiments, the subject has a MCL-1 dependency percentage of no more than 40%. In some embodiments, the subject has a MCL-1 dependency percentage of no more than 30%. In some embodiments, the subject has a MCL-1 dependency percentage of no more than 20%.

In embodiments, the subject has a predetermined MCL-1 dependency percentage of at least 5%. In embodiments, the subject has a predetermined MCL-1 dependency percentage of at least 10%. In embodiments, the subject has a predetermined MCL-1 dependency percentage of at least 20%. In embodiments, the subject has a predetermined MCL-1 dependency percentage of at least 30%. In embodiments, the subject has a predetermined MCL-1 dependency percentage of at least 40%. In embodiments, the subject has a predetermined MCL-1 dependency percentage of at least 50%. In embodiments, the subject has a predetermined MCL-1 dependency percentage of at least 60%. In embodiments, the subject has a predetermined MCL-1 dependency percentage of at least 70%. In some embodiments, the subject has a predetermined MCL-1 dependency percentage of no more than 70%. In some embodiments, the subject has a predetermined MCL-1 dependency percentage of no more than 60%. In some embodiments, the subject has a predetermined MCL-1 dependency percentage of no more than 50%. In some embodiments, the subject has a predetermined MCL-1 dependency percentage of no more than 40%. In some embodiments, the subject has a predetermined MCL-1 dependency percentage of no more than 30%. In some embodiments, the subject has a predetermined MCL-1 dependency percentage of no more than 20%.

Accordingly, in particular embodiments, a subject treated using the methods disclosed herein has a predetermined MCL-1 dependency percentage of at least 15%, a predetermined MCL-1 dependency percentage having been obtained by an in vitro method comprising contacting a first portion of a plurality of cancer cells with a profiling peptide comprising a cellular uptake moiety and a predetermined MCL-1 binding domain, a predetermined MCL-1 binding domain having the sequence of SEQ ID NO:1 or 2. In embodiments, a subject treated using the methods disclosed herein has a predetermined MCL-1 dependency percentage of at least 20%. In embodiments, a subject treated using the methods disclosed herein has a predetermined MCL-1 dependency percentage of at least 30%. In embodiments, a subject treated using the methods disclosed herein has a predetermined MCL-1 dependency percentage of at least 40%. In embodiments, a subject treated using the methods disclosed herein has a predetermined MCL-1 dependency percentage of at least 50%. In embodiments, a subject treated using the methods disclosed herein has a predetermined MCL-1 dependency percentage of at least 60%.

In some embodiments, a subject treated using the methods disclosed herein has a predetermined MCL-1 dependency percentage of less than 75%. In some embodiments, a subject treated using the methods disclosed herein has a predetermined MCL-1 dependency percentage of less than 50%. In some embodiments, a subject treated using the methods disclosed herein has a predetermined MCL-1 dependency percentage of less than 30%. In some embodiments, a subject treated using the methods disclosed herein has a predetermined MCL-1 dependency percentage of less than 25%. In some embodiments, a subject treated using the methods disclosed herein has a predetermined MCL-1 dependency percentage of less than 20%. In further embodiments, methods of the present disclosure include administering the therapeutic agents described herein to the subject regardless of mitochondrial integrity and/or MCL-1 dependency data.

Additional profiling peptides and methods of use are disclosed in US 2016/0303101 and US 2018/0172673, which are incorporated by referenced herein for the teachings regarding the same In some of the foregoing embodiments, the subject has a chromosome 17p deletion.

In some other foregoing embodiments, the BCL-2 inhibitor is Venetoclax (i.e., ABT-199). In some other embodiments the BCL-inhibitor is an antisense oligonucleotide drug (e.g., oblimersen), a BH3 mimetic (e.g., ABT-737, ABT-737-d8 or navitoclax/ABT-263 or ABT-263-d8), a novel non-peptide inhibitor (e.g., TW-37), a pan-BCL-2 inhibitor (e.g., Sabutoclax, Obatoclax), a BCL-xl/BH3 domain interaction inhibitor (e.g., BH3I-1), a BCL-xl inhibitor (e.g., A-1331852 or A-1155463), a non-peptidic ligand of BCL-2 (e.g., HA14-1), a Bax activator (e.g., BAM7), a small molecule BCL-2/BH4 domain antagonist (e.g., BDA-366), a flavonoid (e.g., Licochalcone A). In certain specific embodiments the BCL-2 inhibitor is FX1, AT-101, A-1210477, gambogic acid, UMI-77, Gossypol, (-)-Epigallocatechin Gallate, EM20-25, Nilotinib or Nilotinib-d3, YC137, AG 1024, 3-bromopyruvic acid, Fluvastatin, Piperlongumine, 2,3-DCPE, 2-methoxy-antimycin A3 or Marinopyrrole A (i.e., Maritoclax).

In some of the foregoing embodiments, the method provides treating cancer in a subject in need thereof, provided that Venetoclax/ABT-199 is not co-administered with alvocidib or a prodrug thereof. Certain specific embodiments provide a treatment regimen wherein Venetoclax/ABT-199 is not administered in combination with an MCL-1 inhibitor (e.g., alvocidib or a prodrug thereof) during the course of the treatment regimen. For example, in some embodiments the patient first receives a BCL-2 inhibitor, such as Venetoclax, and after having been found resistant or non-responsive to the BCL-2 inhibitor, the patient is then treated with a regimen comprising an MCL-1 inhibitor, such as alvocidib or a prodrug thereof.

In certain specific embodiments, the treatment regimen comprises alvocidib or a prodrug thereof, or a pharmaceutically acceptable salt thereof, cytarabine, and mitoxantrone (ACM). In certain specific embodiments, the treatment regimen comprises alvocidib or a prodrug thereof, or a pharmaceutically acceptable salt thereof, cytarabine, and daunorubicin (ACD).

In embodiments, the cancer is a solid cancer. In some embodiments, the cancer comprises a solid tumor. In embodiments, the cancer comprises a colorectal, breast, prostate, lung, pancreatic, renal, or ovarian tumor. In embodiments, the cancer is a non-solid cancer. In various embodiments, the cancer is a pre-metastatic cancer. In various embodiments, the cancer is a metastatic cancer.

In some of the foregoing embodiments, the cancer is a hematologic cancer. In certain related embodiments, the hematologic cancer is selected from the group consisting of acute myelogenous leukemia (AML), multiple myeloma, follicular lymphoma, acute lymphoblastic leukemia (ALL), chronic lymphocytic leukemia, and non-Hodgkin's lymphoma. In specific embodiments, the hematologic cancer is acute myelogenous leukemia (AML). In particular embodiments, the AML is relapsed or refractory AML. In some embodiments, the AML is frontline AML. In another specific embodiment, the hematologic cancer is multiple myeloma. In some embodiments the hematologic cancer is myelodysplasic syndrome (MDS) or chronic lymphocytic leukemia (CLL). In specific embodiments, the hematologic cancer is MDS. In specific embodiments, the hematologic cancer is high risk MDS. In specific embodiments, the hematologic cancer is CLL.

In some other embodiments, the invention relates to one or more of the following cancers: acute lymphoblastic leukemia (ALL), acute myeloid leukemia (AML), adrenocortical carcinoma, AIDS-related cancers, anal cancer, appendix cancer, astrocytoma (e.g., childhood cerebellar or cerebral), basal-cell carcinoma, bile duct cancer, bladder cancer, bone tumor (e.g., osteosarcoma, malignant fibrous histiocytoma), brainstem glioma, brain cancer, brain tumors (e.g., cerebellar astrocytoma, cerebral astrocytoma/malignant glioma, ependymoma, medulloblastoma, supratentorial primitive neuroectodermal tumors, visual pathway and hypothalamic glioma), breast cancer, bronchial adenomas/carcinoids, Burkitt's lymphoma, carcinoid tumors, central nervous system lymphomas, cerebellar astrocytoma, cervical cancer, chronic lymphocytic leukemia (CLL), chronic myelogenous leukemia (CML), chronic myeloproliferative disorders, colon cancer, cutaneous t-cell lymphoma, desmoplastic small round cell tumor, endometrial cancer, ependymoma, esophageal cancer, Ewing's sarcoma, extracranial germ cell tumor, extragonadal germ cell tumor, extrahepatic bile duct cancer, eye cancer, gallbladder cancer, gastric (stomach) cancer, gastrointestinal stromal tumor (GIST), germ cell tumor (e.g., extracranial, extragonadal, ovarian), gestational trophoblastic tumor, gliomas (e.g., brain stem, cerebral astrocytoma, visual pathway and hypothalamic), gastric carcinoid, head and neck cancer, heart cancer, hepatocellular (liver) cancer, hypopharyngeal cancer, hypothalamic and visual pathway glioma, intraocular melanoma, islet cell carcinoma (endocrine pancreas), kidney cancer (renal cell cancer), laryngeal cancer, leukemias (e.g., acute lymphocytic leukemia, acute myelogenous leukemia, chronic lymphocytic leukemia, chronic myeloid leukemia, hairy cell), lip and oral cavity cancer, liposarcoma, liver cancer, lung cancer (e.g., non-small cell, small cell), lymphoma (e.g., AIDS-related, Burkitt, cutaneous T-cell Hodgkin, non-Hodgkin, primary central nervous system), medulloblastoma, melanoma, Merkel cell carcinoma, mesothelioma, metastatic squamous neck cancer, mouth cancer, multiple endocrine neoplasia syndrome, multiple myeloma, mycosis fungoides, myelodysplastic syndromes, myelodysplastic/myeloproliferative diseases, myelogenous leukemia, myeloid leukemia, myeloid leukemia, myeloproliferative disorders, chronic, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma, ovarian cancer, pancreatic cancer, pancreatic cancer, paranasal sinus and nasal cavity cancer, parathyroid cancer, penile cancer, pharyngeal cancer, pheochromocytoma, pineal astrocytoma and/or germinoma, pineoblastoma and supratentorial primitive neuroectodermal tumors, pituitary adenoma, plasma cell neoplasia/multiple myeloma, pleuropulmonary blastoma, primary central nervous system lymphoma, prostate cancer, rectal cancer, renal cell carcinoma (kidney cancer), renal pelvis and ureter, retinoblastoma, rhabdomyosarcoma, salivary gland cancer, sarcoma (e.g., Ewing family, Kaposi, soft tissue, uterine), Sezary syndrome, skin cancer (e.g., nonmelanoma, melanoma, merkel cell), small cell lung cancer, small intestine cancer, soft tissue sarcoma, squamous cell carcinoma, squamous neck cancer, stomach cancer, supratentorial primitive neuroectodermal tumor, t-cell lymphoma, testicular cancer, throat cancer, thymoma and thymic carcinoma, thyroid cancer, trophoblastic tumors, ureter and renal pelvis cancers, urethral cancer, uterine cancer, uterine sarcoma, vaginal cancer, visual pathway and hypothalamic glioma, vulvar cancer, Waldenstrom macroglobulinemia, and Wilms tumor. In some embodiments, the cancer is breast cancer. In some embodiments, the cancer is prostate cancer. In some embodiments, the cancer is lung cancer.

Exemplary Dosages

An effective amount means an amount effective to prevent, alleviate or ameliorate symptoms of disease or prolong the survival of the subject being treated. Determination of an effective amount is well within the capability of those skilled in the art, especially in light of the detailed disclosure provided herein.

For example, for any method for treating described herein, the effective amount or dose can be estimated initially from cell culture assays. Then, the dosage can be formulated for use in animal models so as to achieve a circulating concentration range that includes the $IC_{50}$ as determined in cell culture (i.e., the concentration of alvocidib which achieves a half-maximal inhibition of MCL-1 expression). Such information can then be used to more accurately determine useful doses in humans.

Toxicity and therapeutic efficacy of the methods described herein can be determined by standard pharmaceutical procedures in cell cultures or experimental animals, e.g., by determining the $IC_{50}$ and the $LD_{50}$. The data obtained from cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See, e.g., GOODMAN & GILMAN'S THE PHARMACOLOGICAL BASIS OF THERAPEUTICS, Ch. 3, $9^{th}$ ed., Ed. by Hardman, J., and Limbard, L., McGraw-Hill, New York City, 1996, p. 46.)

Dosage amount and interval may be adjusted individually to provide plasma levels of the active species which are sufficient to maintain the protein inhibiting effects. These plasma levels are referred to as minimal effective concentrations (MECs). The MEC will vary for each composition but can be estimated from in vitro data, e.g., the concentration necessary to achieve 50-90% inhibition of MCL-1. The amount of alvocidib or a prodrug thereof administered will, of course, be dependent on the subject being treated, the severity of the affliction, the manner of administration, the judgment of the prescribing physician, etc. HPLC assays or bioassays can be used to determine plasma concentrations.

Dosage intervals can also be determined using MEC value. In certain embodiments, methods of treatment should be performed such that plasma levels are maintained above the MEC for about 10 to 90% of the time, preferably between about 30 to 90% of the time and most preferably between about 50 to 90% of the time.

In some of the foregoing embodiments, the effective amounts may range from approximately 2.5 to 1500 mg/m$^2$ per day. Additional illustrative amounts range from 0.2 to 1000 mg/qid, 2 to 500 mg/qid, and 20 to 250 mg/qid.

In embodiments wherein local administration or selective uptake is of concern, the effective local concentration of alvocidib may not be related to plasma concentration, and other procedures known in the art may be employed to determine the correct dosage amount and interval.

In some specific embodiments, the compounds administered as part of the present methods may, if desired, be presented in a pack or dispenser device, such as an FDA approved kit, which may contain one or more unit dosage forms containing an active ingredient(s). The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compounds (e.g., alvocidib or a prodrug thereof) in certain embodiments are optionally formulated in a compatible pharmaceutical carrier may also be prepared, placed in an appropriate container, and labeled for treatment of an indicated condition. Suitable conditions indicated on the label may include treatment of a BCL-2 inhibitor resistant cancer, a BCL-2 resistant tumor, and the like.

In additional embodiments, the compounds and methods of treatment described herein can be used in combination with one or more other chemotherapeutic agents. Dosages may be adjusted for any drug-drug reaction. In one embodiment, the additional chemotherapeutic agent is selected from the group consisting of alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb); inhibitors of PKC-I, Raf, H-Ras, EGFR (e.g., erlotinib (Tarceva)) and VEGF-A that reduce cell proliferation, dacogen, velcade, and pharmaceutically acceptable salts, acids or derivatives of any of the above.

In addition, some embodiments of the methods described above can be carried out in combination with radiation therapy, wherein the radiation therapy is effective in treating the above diseases. Techniques for administering radiation therapy are known in the art, and these techniques can be used in the combination therapy described herein.

Embodiments of the method comprise administering compounds that are effective over a wide dosage range. For example, in the treatment of adult humans, dosages from 0.01 to 1000 mg, from 0.5 to 100 mg, from 1 to 50 mg per day, and from 5 to 40 mg per day are examples of dosages. An exemplary dosage is 10 to 30 mg per day. The exact dosage will depend upon the route of administration, the form in which the composition is administered, the subject to be treated, the body weight of the subject to be treated, and the preference and experience of the attending physician.

In embodiments, alvocidib or a prodrug thereof is administered in a dose ranging from about 10 mg/m$^2$ to about 150 mg/m$^2$ per day. In embodiments, alvocidib or a prodrug thereof is administered in a dose ranging from about 50 mg/m$^2$ to about 130 mg/m$^2$ per day. In some embodiments, alvocidib or a prodrug thereof is administered in a dose ranging from about 30 mg/m$^2$ to about 50 mg/m$^2$ per day. In some embodiments, alvocidib or a prodrug thereof is administered in a dose ranging from about 35 mg/m$^2$ to about 45 mg/m$^2$ per day. In some embodiments, alvocidib or a prodrug thereof is administered in a dose ranging from about 550 mg/m$^2$ to about 750 mg/m$^2$ per day. In some embodiments, alvocidib or a prodrug thereof is administered in a dose ranging from about 650 mg/m$^2$ to about 675 mg/m$^2$ per day.

In certain embodiments, the dose of alvocidib or a prodrug thereof ranges from about 30 mg/m$^2$ to about 120 mg/m$^2$ per day. In some such embodiments, the dose of alvocidib or a prodrug thereof is administered via two or more routes of administration. In some embodiments, the method comprises administering a single dose. Typically, such administration will be by injection, e.g., intravenous injection, in order to introduce an effective amount of a compound (e.g., alvocidib) quickly. However, other routes are used as appropriate. For example, in some embodiments, a prodrug of alvocidib is orally administered. In some embodiments, a single dose may also be used for treatment of an acute condition.

In embodiments, alvocidib or a prodrug thereof is administered via a bolus injection in a dose ranging from about 15 mg/m$^2$ to about 35 mg/m$^2$ per day. In some embodiments, alvocidib or a prodrug thereof is administered via a bolus injection in a dose ranging from about 20 mg/m$^2$ to about 30 mg/m$^2$ per day. In some embodiments, alvocidib or a prodrug thereof is administered via intravenous infusion in a dose ranging from about 30 mg/m$^2$ to about 60 mg/m$^2$ per day. In embodiments, alvocidib or a prodrug thereof is administered via bolus injection in a dose ranging from about 45 mg/m$^2$ to about 90 mg/m$^2$ per day. In embodiments, alvocidib or a prodrug thereof is administered via intravenous infusion in a dose ranging from about 90 mg/m$^2$ to about 110 mg/m$^2$ per day.

In some embodiments, alvocidib or a prodrug thereof is administered via a bolus injection in a dose ranging from about 20 mg/m$^2$ to about 40 mg/m$^2$ per day. In some embodiments, alvocidib or a prodrug thereof is administered via intravenous infusion in a dose ranging from about 40 mg/m$^2$ to about 80 mg/m$^2$ per day.

In certain embodiments, alvocidib or a prodrug thereof, is administered via a bolus injection in a dose ranging from about 20 mg/m$^2$ to about 40 mg/m$^2$ per day. In some embodiments, alvocidib or a prodrug thereof, is administered via intravenous infusion in a dose ranging from about 40 mg/m$^2$ to about 80 mg/m$^2$ per day.

In some embodiments, the method comprises dosing a compound or compounds in multiple doses. In some embodiments, dosing is about once, twice, three times, four times, five times, six times, or more than six times per day. In other embodiments, dosing is about once a month, once every two weeks, once a week, or once every other day. In yet another embodiment the dosing continues for more than about 6, 10, 14, 28 days, two months, six months, or one year. In some cases, continuous dosing is achieved and maintained as long as necessary.

Treatment may continue as long as necessary. In some embodiments, the method of treating is maintained for more than 1, 2, 3, 4, 5, 6, 7, 14, or 28 days. In some embodiments, the method of treating is continued for less than 28, 14, 7, 6, 5, 4, 3, 2, or 1 day. In some embodiments, the method of treating is chronically on an ongoing basis, e.g., for the treatment of chronic effects.

Compositions

In specific embodiments, therapeutic agents (e.g., alvocidib or a prodrug thereof) are formulated in a conventional manner with one or more physiologically acceptable carriers comprising excipients and auxiliaries which facilitate processing of the compounds into preparations which can be used pharmaceutically. Proper formulation is dependent upon the route of administration chosen.

Any additional pharmaceutically acceptable techniques, carriers, and excipients are used as suitable to formulate the pharmaceutical compositions described herein: Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Furthermore, compounds of the invention (e.g., alvocidib or a prodrug thereof) which exist in free base or acid form can be converted to their pharmaceutically acceptable salts by treatment with the appropriate inorganic or organic base or acid by methods known to one skilled in the art. Salts of the compounds used herein can be converted to their free base or acid form by standard techniques.

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, administering is local rather than systemic, for example, via injection directly into an organ, often in a depot preparation or sustained release formulation. In specific embodiments, long acting formulations are administered by implantation (for example subcutaneously or intramuscularly) or by intramuscular injection. Furthermore, in other embodiments, administering comprises delivering a compound in a targeted drug delivery system, for example, in a liposome coated with organ-specific antibody. In such embodiments, the liposomes are targeted to and taken up selectively by the organ. In yet other embodiments, the administering comprises delivering a rapid release formulation, in the form of an extended release formulation, or in the form of an intermediate release formulation. In yet other embodiments, administering comprises topical administration. In some embodiments, the method comprises administering a suspension, solution, and/or emulsion. In certain embodiments, the method of treating comprises administering a mixture of chemical components, such as carriers, stabilizers, diluents, dispersing agents, suspending agents, thickening agents, and/or excipients.

In one embodiment, the method comprises administering a composition formulated in aqueous solution. In specific embodiments, the aqueous solution is selected from, by way of example only, a physiologically compatible buffer, such as Hank's solution, Ringer's solution, or physiological saline buffer. In other embodiments, the composition is formulated for transmucosal administration. In specific embodiments, the composition formulated for transmucosal administration includes penetrants that are appropriate to the barrier to be permeated. In still other embodiments, compositions are formulated for other parenteral injection methods, wherein appropriate formulations include aqueous or non-aqueous solutions. In specific embodiments, such compositions include physiologically compatible buffers and/or excipients.

In some embodiments, compositions may be administered orally. Thus, in these embodiments, the compositions are formulated in oral dosage forms that include, by way of example only, tablets, powders, pills, dragees, capsules, liquids, gels, syrups, elixirs, slurries, suspensions and the like.

In related embodiments, dosage forms, such as dragee cores and tablets, are provided with one or more suitable coating. In specific embodiments, concentrated sugar solutions are used for coating the dosage form. The sugar solutions optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active composition doses.

Oral dosage forms include push-fit capsules made of gelatin, as well as soft, sealed capsules made of gelatin and a plasticizer, such as glycerol or sorbitol. In specific embodiments, push-fit capsules contain the active ingredients in ad-mixture with one or more filler. Fillers include, by way of example only, lactose, binders such as starches, and/or lubricants such as talc or magnesium stearate and, optionally, stabilizers. In other embodiments, soft capsules contain one or more composition that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of compounds described herein are formulated and delivered via buccal or sublingual administration. Formulations suitable for buccal or sublingual administration include, by way of example only, tablets, lozenges, or gels. In still other embodiments, compounds are formulated and administered via parental injection, including bolus injection or continuous infusion. In specific embodiments, formulations for injection are presented in unit dosage form (e.g., in ampoules) or in multi-dose containers. Preservatives are, optionally, added to the injection formulations. In still other embodiments, the compounds are formulated and administered in a form suitable for parenteral injection as sterile suspensions, solutions or emulsions in oily or aqueous vehicles. Parenteral injections optionally contain formulatory agents such as suspending, stabilizing and/or dispersing agents. In additional embodiments, suspensions are prepared and administered as appropriate oily injection suspensions. Suitable lipophilic solvents or vehicles for use in the methods described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension may contain suitable stabilizers or agents which increase solubility to allow for the preparation of highly concentrated solutions. Alternatively, in other embodiments, the method comprises administering a powder form for constitution with a suitable vehicle, e.g., sterile pyrogen-free water, before use.

In still other embodiments, the method comprises topical administration. Topical administration generally includes topically administrable compositions, such as solutions, suspensions, lotions, gels, pastes, medicated sticks, balms, creams or ointments. Such compositions optionally contain solubilizers, stabilizers, tonicity enhancing agents, buffers and preservatives.

In yet other embodiments, the method comprises transdermal administration. In specific embodiments, transdermal administration employs transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the composition is accomplished by means of iontophoretic patches and the like. In certain embodiments, transdermal patches provide controlled delivery of the composition. In specific embodiments, the rate of absorption is slowed by using rate-controlling membranes or by trapping the composition within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the composition optionally with carriers, optionally a rate controlling barrier to deliver the composition to the skin of the host at a controlled and predetermined rate over a prolonged period of time, and means to secure the device to the skin.

In still other embodiments, the method comprises rectal administration using a rectal composition such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In addition, the compositions used in embodiments of the methods described herein optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

In some of the foregoing embodiments, the effective amount is formulated in a composition, wherein the effective amount has a concentration less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some other embodiments of the foregoing, the effective amount is formulated in a composition, wherein the effective amount has a concentration greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25% 4%, 3.75%, 3.50%, 3.25% 3%, 2.75%, 2.50%, 2.25% 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some related embodiments, the effective amount has a concentration in the range from approximately 0.0001% to approximately 50%, from approximately 0.001% to approximately 40%, from approximately 0.01% to approximately 30%, from approximately 0.02% to approximately 29%, from approximately 0.03% to approximately 28%, from approximately 0.04% to approximately 27%, from approximately 0.05% to approximately 26%, from approximately 0.06% to approximately 25%, from approximately 0.07% to approximately 24%, from approximately 0.08% to approximately 23%, from approximately 0.09% to approximately 22%, from approximately 0.1% to approximately 21%, from approximately 0.2% to approximately 20%, from approximately 0.3% to approximately 19%, from approximately 0.4% to approximately 18%, from approximately 0.5% to approximately 17%, from approximately 0.6% to approximately 16%, from approximately 0.7% to approximately 15%, from approximately 0.8% to approximately 14%, from approximately 0.9% to approximately 12%, or from approximately 1% to approximately 10% w/w, w/v or v/v.

In some other related embodiments, the effective amount is in the range from approximately 0.001% to approximately 10%, from approximately 0.01% to approximately 5%, from approximately 0.02% to approximately 4.5%, from approximately 0.03% to approximately 4%, from approximately 0.04% to approximately 3.5%, from approximately 0.05% to approximately 3%, from approximately 0.06% to approximately 2.5%, from approximately 0.07% to approximately 2%, from approximately 0.08% to approximately 1.5%, from approximately 0.09% to approximately 1%, or from approximately 0.1% to approximately 0.9% w/w, w/v or v/v.

In some embodiments, the effective amount is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the effective amount is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the effective amount is in the range of 0.0001-10 g, 0.0005-9 g, 0.001-8 g, 0.005-7 g, 0.01-6 g, 0.05-5 g, 0.1-4 g, 0.5-4 g, or 1-3 g.

The following embodiments are included within the scope of this disclosure.

1. A method for treating a cancer in a subject in need thereof, the method comprising administering an effective amount of a treatment regimen comprising alvocidib or a prodrug thereof, or a pharmaceutically acceptable salt thereof, wherein the cancer is BCL-2 inhibitor resistant and wherein the subject is non-responsive or resistant to a prior treatment with a BCL-2 inhibitor, thereby treating the cancer in the subject.

2. A method for treating a cancer in a subject in need thereof, the method comprising:
determining that the cancer is BCL-2 inhibitor resistant; and
administering an effective amount of a treatment regimen comprising alvocidib or a prodrug thereof, or a pharmaceutically acceptable salt thereof, to the subject, thereby treating the cancer.

3. A method for treating a cancer in a subject in need thereof, the method comprising:
identifying the subject as likely to respond to treatment with alvocidib or a prodrug thereof if the cancer is BCL-2 inhibitor resistant and the subject is non-responsive or resistant to a prior treatment with a BCL-2 inhibitor; and
administering a treatment regimen comprising an effective amount of alvocidib or a prodrug thereof, or a pharmaceutically acceptable salt thereof, to the subject.

4. A method for treating a cancer in a subject in need thereof, the method comprising:
administering a treatment regimen comprising alvocidib or a prodrug thereof, or a pharmaceutically acceptable salt thereof, to the subject, the cancer being BCL-2 inhibitor resistant as determined by an in vitro method comprising:
obtaining a cancer cell from the subject; and
i) quantifying expression of BCL-2 and MCL-1 in the cancer cell, wherein an increase in MCL-1 expression relative to BCL-2 expression indicates the subject has a BCL-2 inhibitor resistant cancer;
ii) determining dependency on BCL-2 in the cancer cell, wherein a low BCL-2 dependency indicates the subject has a BCL-2 inhibitor resistant cancer; or
iii) determining dependency on MCL-1 in the cancer cell, wherein a high MCL-1 dependency indicates the subject has a BCL-2 inhibitor resistant cancer.

5. The method of any one of embodiments 1-4, wherein the subject has a chromosome 17p deletion.

6. The method of any one of embodiments 1-5, wherein the cancer is a hematologic cancer.

7. The method of embodiment 6, wherein the hematologic cancer is selected from the group consisting of acute myelogenous leukemia (AML), multiple myeloma, follicular lymphoma, acute lymphoblastic leukemia (ALL), chronic lymphocytic leukemia, and non-Hodgkin's lymphoma.

8. The method of embodiment 7, wherein the hematologic cancer is acute myelogenous leukemia (AML).

9. The method of embodiment 8, wherein the AML is relapsed or refractory AML.

10. The method of embodiment 8, wherein the AML is frontline AML.

11. The method of embodiment 7, wherein the hematologic cancer is multiple myeloma.

12. The method of embodiment 6, wherein the hematologic cancer is myelodysplasic syndrome (MDS).

13. The method of embodiment 10, wherein the MDS is high risk MDS.

14. The method of embodiment 6, wherein the hematologic cancer is chronic lymphocytic leukemia (CLL).

15. The method of any one of embodiments 1-5, wherein the cancer is a solid cancer.

16. The method of embodiment 15, wherein the solid cancer is prostate cancer.

17. The method of embodiment 15, wherein the solid cancer is breast cancer.

18. The method of embodiment 15, wherein the solid cancer is lung cancer.

19. The method of any one of embodiments 15-18, wherein the solid cancer comprises one or more solid tumors.

20. The method of any one of embodiments 1-19, wherein the treatment regimen further comprises cytarabine and mitoxantrone.

21. The method of any one of embodiments 1-19, wherein the treatment regimen further comprises cytarabine and daunorubicin.

22. The method of any one of embodiments 1-21, wherein the treatment regimen comprises the prodrug of alvocidib.

23. The method of any one of embodiments 1-22, wherein the prodrug of alvocidib is a phosphate prodrug.

24. The method of embodiment 23, wherein the phosphate prodrug of alvocidib has the following structure:

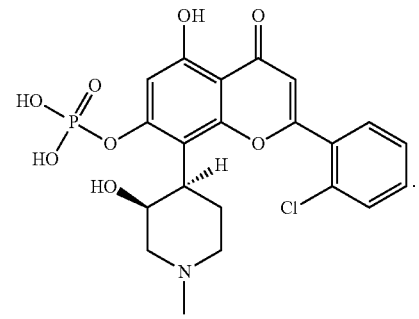 [SMILES: CN1CC[C@H](c2c(OP(=O)(O)O)cc(O)c3c(=O)cc(-c4ccccc4Cl)oc23)[C@H](O)C1]

25. The method of any one of embodiments 1-21, wherein the treatment regimen comprises alvocidib.

26. The method of any one of embodiments 2 or 4-25, wherein the subject has received a prior treatment with a BCL-2 inhibitor.

27. The method of embodiment 26, wherein the subject is non-responsive or resistant to the prior treatment with the BCL-2 inhibitor.

28. The method of any one of embodiments 1-27, wherein the BCL-2 inhibitor is Venetoclax.

29. The method of any one of embodiments 1-28, wherein the subject has an MCL-1 dependency percentage of at least 15%, the MCL-1 dependency percentage having been obtained by an in vitro method comprising contacting a first portion of a plurality of cancer cells with a profiling peptide comprising a cellular uptake moiety and an MCL-1 binding domain, the MCL-1 binding domain having the sequence of SEQ ID NO:1 or SEQ ID NO:2.

30. The profiling peptide of embodiment 29, wherein the profiling peptide consists of the sequence of SEQ ID NO: 1 or SEQ ID NO:2.

31. The profiling peptide of embodiment 29, wherein the profiling peptide comprises the sequence of SEQ ID NO: 1.

32. The profiling peptide of embodiment 29, wherein the profiling peptide comprises the sequence of SEQ ID NO:2.

33. The method of any one of embodiments 29-32, wherein the subject has an MCL-1 dependency percentage of at least 20%.

34. The method of any one of embodiments 29-33, wherein the subject has an MCL-1 dependency percentage of at least 30%.

35. The method of any one of embodiments 29-34, wherein the subject has an MCL-1 dependency percentage of at least 40%.

36. The method of any one of embodiments 29-35, wherein the in vitro method further comprises:

contacting a second portion of the plurality of cancer cells with a negative control; and determining a percent polarization of the first portion and of the second portion of the plurality of cancer cells.

37. The method of embodiment 36, wherein the in vitro method further comprise determining a Mcl-1 dependency percentage (MDP) based at least on the percent polarization of the first portion and of the second portion of the plurality of cancer cells.

38. The method of embodiment 36 or 37, wherein the negative control is water.

39. The method of any one of embodiments 36-38, wherein the in vitro method further comprises contacting a third portion of the plurality of cancer cells with a positive control.

40. The method of embodiment 39, wherein the positive control is Carbonyl cyanide-4-(trifluoromethoxy)phenylhydrazone (FCCP), Carbonyl cyanide m-chlorophenyl hydrazone (CCCP), or N5,N6-bis(2-fluorophenyl)-[1,2,5]oxadiazolo[3,4-b]pyrazine-5,6-diamine (BAM-15).

41. The method of embodiment 39 or 40, wherein the positive control is CCCP.

42. The method of any one of embodiments 39-41, wherein the in vitro method further comprises contacting the first portion, the second portion, and the third portion of the plurality of cells with a detecting agent.

43. The method of embodiment 42, wherein the detecting agent is a dye.

44. The method of embodiment 43, wherein the dye is a 3,3'-Dihexyloxacarbocyanine Iodide ($DiOC_6$).

Embodiments of this disclosure are further illustrated by the following non-limiting examples.

EXAMPLES

Example 1

Dose-Dependent Mcl-1 Protein Reduction in MV-4-11 Cells

An AML cell line, MV-4-11, expresses MCL-1. MCL-1 is a key anti-apoptotic protein in MV-4-11 cells. Alvocidib, a CDK9 inhibitor, lowers the expression of MCL-1 in mRNA, which is already well documented in the literature. As a result, alvocidib decreases MCL-1 expression in MV-4-11 in a dose dependent manner (FIG. 1). The dose dependence is observed by monitoring the relative expression of MCL-1 compared to controls when cells are dosed with alvocidib at concentrations ranging from 0-8 µM. MV-4-11 cells were treated with alvocidib in vitro, harvested and analyzed to probe for changes relative to controls.

Figure 2:
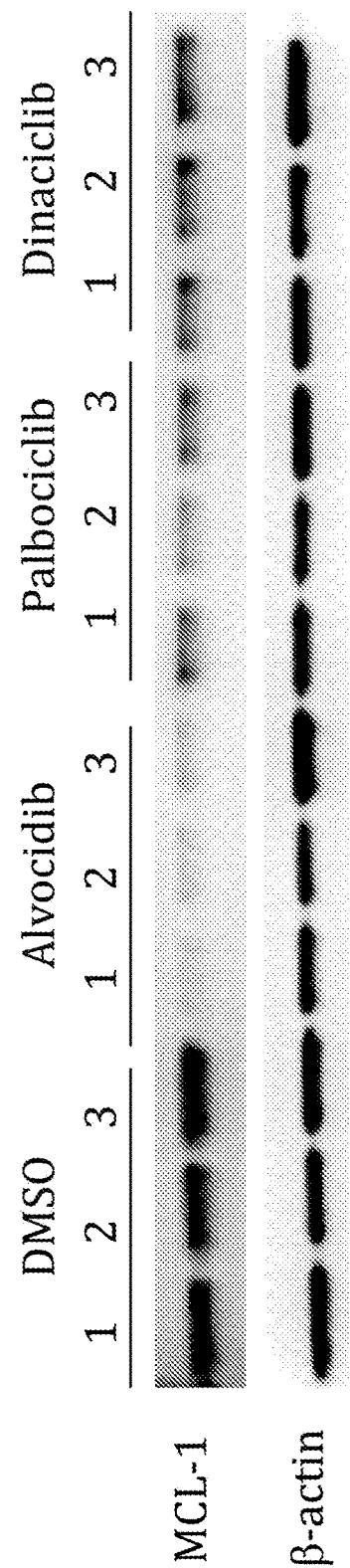
FIG. 2 illustrates a dose dependent decrease in MCL-1 expression in MV-4-11 cells treated with alvocidib, palbociclib and dinaciclib.

Additionally, other exemplary CDK9 inhibitors (i.e., palbociclib and dinaciclib) were evaluated, along with alvocidib. Each exemplary CDK9 inhibitor showed decreased MCL-1 expression in MV-4-11 cells after a 24 hour treatment. Alvocidib, the most potent CDK9 inhibitor of the group, demonstrated the strongest impact on MCL-1 protein levels (FIG. 2).

Example 2

In Vivo and In Vitro Activity of Alvocidib in AML Cells Resistant to Venetoclax

Figure 3:
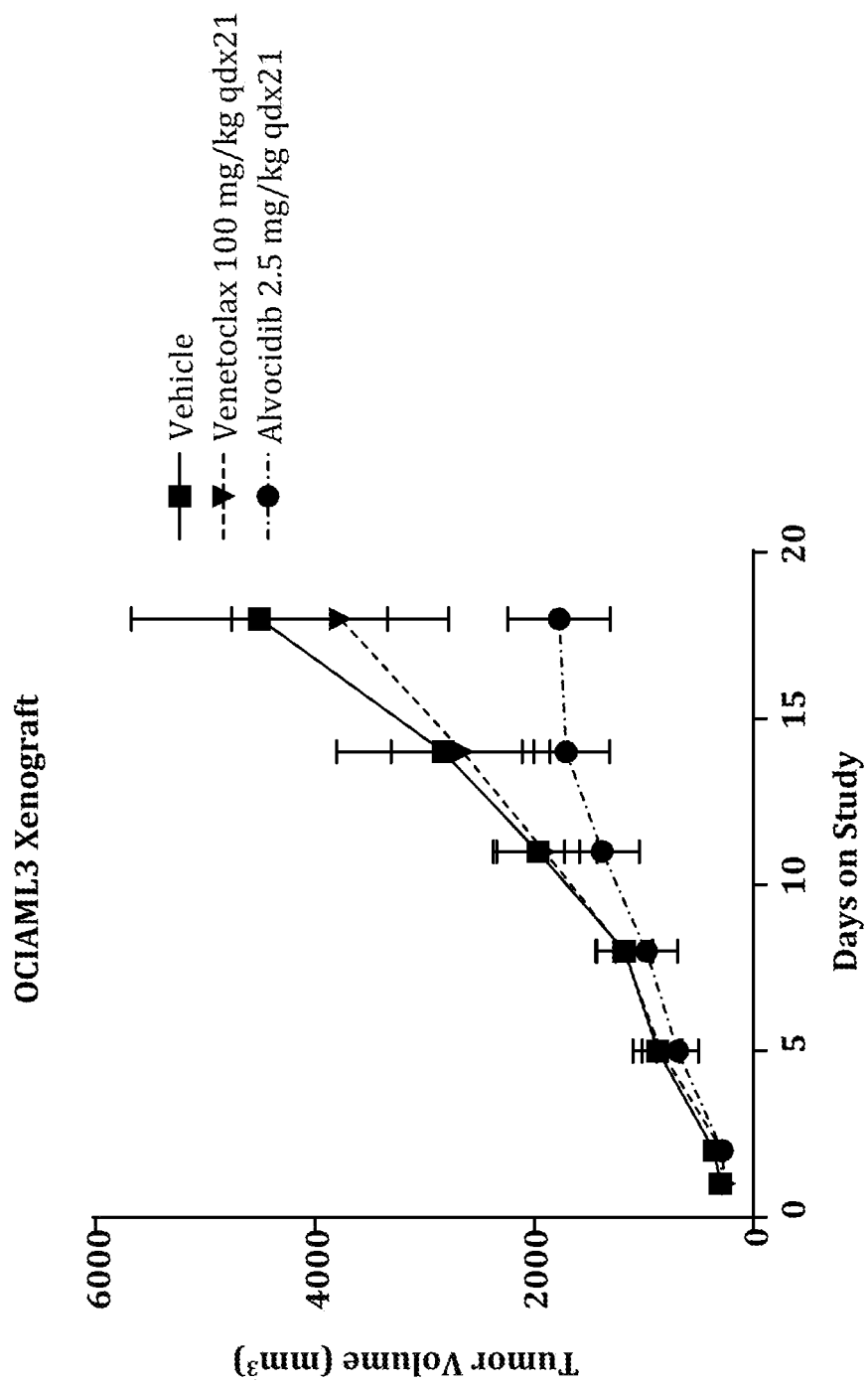
FIG. 3 illustrates in vivo tumor growth in alvocidib treated OCI-AML3 tumor cells compared to treatment with Venetoclax/ABT-199.

Alvocidib was used alone to test in vivo activity in OCI-AML3 cells. The OCI-AML3 cells are highly resistant to Venetoclax/ABT-199 ($EC_{50}$=2330 nM). To test the in vivo activity, immune deficient mice injected with OCI-AML3 cells were treated with 2.5 mg/kg of alvocidib via intraperitoneal injection or 100 mg/kg of Venetoclax/ABT-199 per os (i.e., oral administration). Each treatment (i.e., alvocidib and Venetoclax/ABT-199) was administered once a day for 21 days. Venetoclax/ABT-199 showed no decrease in tumor volume relative to vehicle alone treatment while treatment with alvocidib alone demonstrated a remarkable 50% reduction in tumor growth by day 21 of treatment (FIG. 3). The extraordinary reduction in tumor growth demonstrates that treatment of BCL-2 inhibitor-resistant patients with an MCL-1 inhibitor unexpectedly and advantageously provides treatment options beyond Venetoclax/ABT-199.

Figure 4:
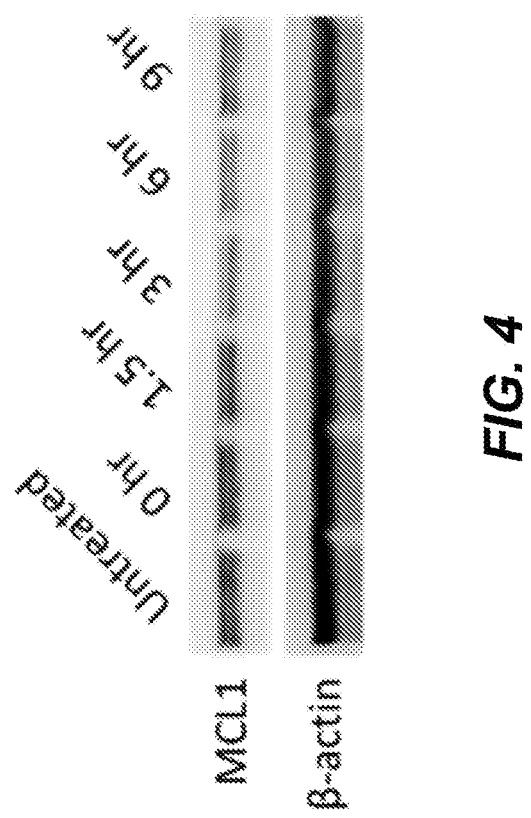
FIG. 4 demonstrates an in vitro decrease in MCL-1 protein expression for OCI-AML3 cells treated with alvocidib.
Figure 5:
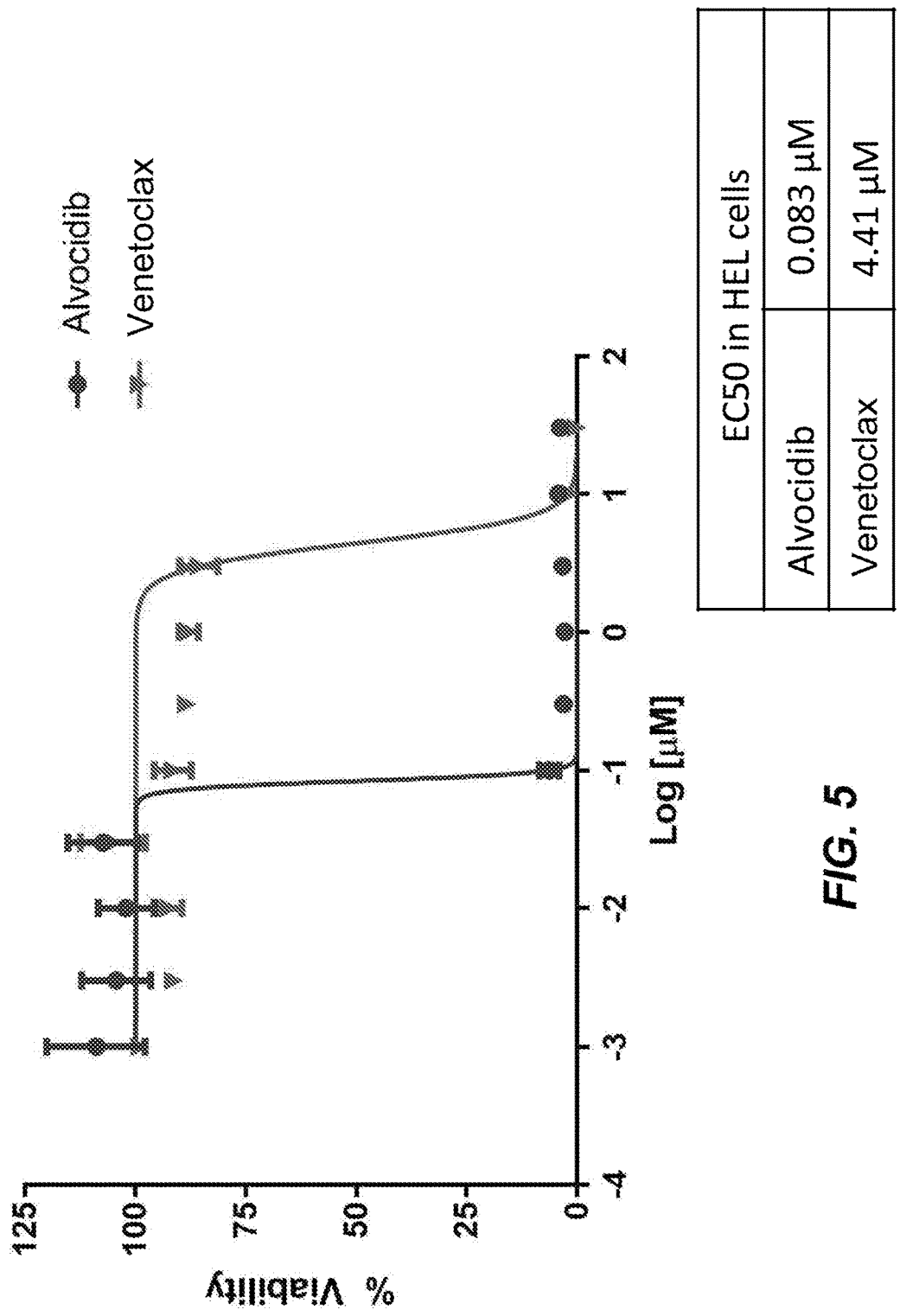
FIG. 5 shows in vitro inhibition of cell viability in alvocidib treated HEL cells compared to treatment with Venetoclax.
Figure 6:
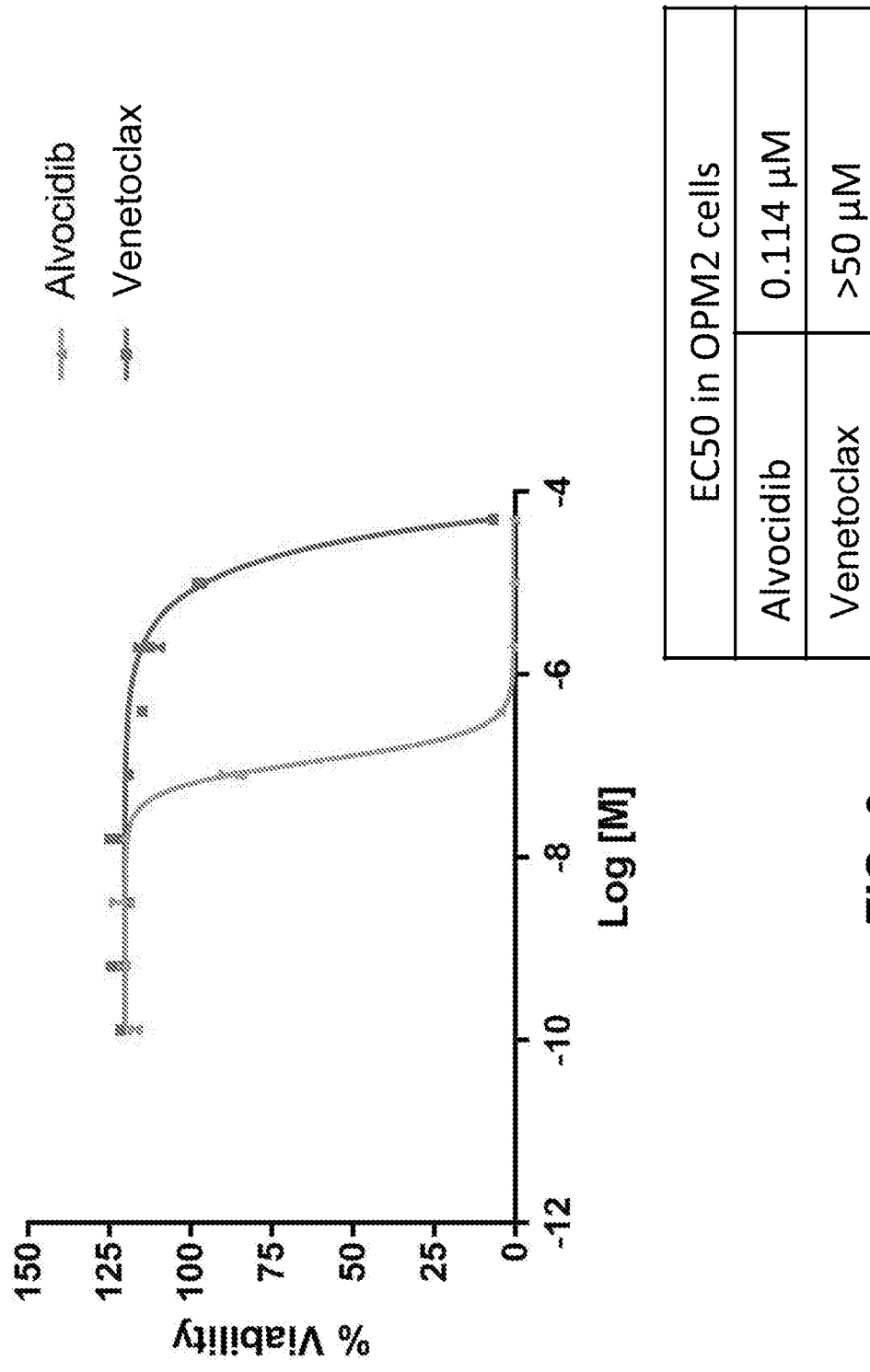
FIG. 6 shows in vitro inhibition of cell viability in alvocidib treated OPM2 cells compared to treatment with Venetoclax.

Alvocidib also shows in vitro activity in OCI-AML3 cells. MCL-1 expression was decreased in OCI-AML3 cells at multiple time points following treatment with alvocidib (FIG. 4).

Example 3

In Vitro Activity of Alvocidib in Erythroleukemia Cells Resistant to Venetoclax

To assess the effects of alvocidib or Venetoclax treatment on leukemic cells, the erythroleukima cell line, HEL, was cultured in RPMI media supplemented with 10% FBS and penicillin/streptomycin. Cell viability was assessed in treated cells using the CellTiter-Glo reagent (Promega), according to manufacturer protocol. Cells were treated in 96-well plates for 72 hours, before being analyzed in a luminescence compatible plate reader. Curve fitting and analysis was performed using Graphpad Prism software.

Example 4

In Vitro Activity of Alvocidib in Multiple Myeloma Cells Resistant to Venetoclax To assess the effects of alvocidib or Venetoclax treatment on multiple myeloma cells, OPM2 cells were cultured in RPMI media supplemented with 10% FBS and penicillin/streptomycin. Cell viability was assessed in treated cells using the CellTiter-Glo reagent (Promega), according to manufacturer protocol. Cells were treated in 96-well plates for 72 hours, before being analyzed in a luminescence compatible plate reader. Curve fitting and analysis was performed using Graphpad Prism software.

From the foregoing it will be appreciated that, although specific embodiments of the invention have been described herein for purposes of illustration, various modifications may be made without deviating from the spirit and scope of the invention. U.S. provisional patent application Ser. No. 62/557,635, filed Sep. 12, 2017 is incorporated herein by reference, in its entirety. Accordingly, the invention is not limited except as by the appended claims.

The invention claimed is:

1. A method for inhibiting a hematologic cancer which is BCL-2 inhibitor resistant in a subject in need thereof, the method comprising administering to the subject an effective amount of a therapy comprising alvocidib, a prodrug of alvocidib, or a pharmaceutically acceptable salt thereof for more than 21 days, wherein the subject is non-responsive or resistant to a prior therapy with a BCL-2 inhibitor, wherein venetoclax, or a pharmaceutically acceptable salt thereof, is not administered in combination with the alvocidib, or a prodrug thereof, or a pharmaceutically acceptable salt thereof, during the course of the therapy.

2. The method of claim 1, further comprising determining that the hematologic cancer is BCL-2 inhibitor resistant by obtaining a hematologic cancer cell from the subject and quantifying expression of BCL-2 and a myeloid cell leukemia 1 (MCL-1) protein in the hematologic cancer cell, wherein an increase in MCL-1 expression relative to BCL-2 expression indicates that the hematologic cancer is BCL-2 inhibitor resistant.

3. The method of claim 1, wherein the hematologic cancer is selected from the group consisting of acute myelogenous leukemia (AML), multiple myeloma, follicular lymphoma, acute lymphoblastic leukemia (ALL), chronic lymphocytic leukemia (CLL), and non-Hodgkin's lymphoma.

4. The method of claim 3, wherein the hematologic cancer is acute myelogenous leukemia (AML).

5. The method of claim 4, wherein the AML is relapsed or refractory AML.

6. The method of claim 3, wherein the hematologic cancer is multiple myeloma.

7. The method of claim 5, wherein the hematologic cancer is myelodysplastic syndrome (MDS).

8. The method of claim 7, wherein the MDS is high risk MDS.

9. The method of claim 3, wherein the hematologic cancer is chronic lymphocytic leukemia (CLL).

10. The method of claim 5, wherein the therapy further comprises cytarabine and mitoxantrone.

11. The method of claim 5, wherein the therapy comprises alvocidib, or a pharmaceutically acceptable salt thereof.

12. The method of claim 5, wherein the therapy comprises a phosphate prodrug of alvocidib, or a pharmaceutically acceptable salt thereof.

13. The method of claim 12, wherein the phosphate prodrug of alvocidib has the following structure:

14. The method of claim 5, wherein the subject has a myeloid cell leukemia 1 (MCL-1) protein dependency percentage of at least 15%, the MCL-1 dependency percentage having been obtained by an in vitro method comprising contacting a first portion of a plurality of cancer cells from the subject with a profiling peptide having the sequence of SEQ ID NO:1 or SEQ ID NO:2.

15. The method of claim 14, wherein the subject has an MCL-1 protein dependency percentage of at least 40%.

16. The method of claim 5, wherein the subject is non-responsive or resistant to a prior therapy with venetoclax, or a pharmaceutically acceptable salt thereof.

17. The method of claim 5, wherein the subject is human.

18. The method of claim 5, wherein the therapy further comprises cytarabine.

* * * * *

SEQUENCE LISTING

```
<160> NUMBER OF SEQ ID NOS: 2

<210> SEQ ID NO 1
<211> LENGTH: 37
<212> TYPE: PRT
<213> ORGANISM: Artificial Sequence
<220> FEATURE:
<223> OTHER INFORMATION: profiling peptide sequence

<400> SEQUENCE: 1

Tyr Gly Arg Lys Lys Arg Arg Gln Arg Arg Arg Gly Gly Gly Arg Pro
1               5                   10                  15

Glu Ile Trp Met Thr Gln Gly Leu Arg Arg Leu Gly Asp Glu Ile Asn
            20                  25                  30

Ala Tyr Tyr Ala Arg
        35

<210> SEQ ID NO 2
<211> LENGTH: 37
<212> TYPE: PRT
<213> ORGANISM: Artificial Sequence
<220> FEATURE:
<223> OTHER INFORMATION: profiling peptide sequence

<400> SEQUENCE: 2

Arg Pro Glu Ile Trp Met Thr Gln Gly Leu Arg Arg Leu Gly Asp Glu
1               5                   10                  15

Ile Asn Ala Tyr Tyr Ala Arg Gly Gly Gly Tyr Gly Arg Lys Lys Arg
            20                  25                  30

Arg Gln Arg Arg Arg
        35
```